United States Patent [19]

Rybak et al.

[11] Patent Number: 6,045,793
[45] Date of Patent: Apr. 4, 2000

[54] RECOMBINANT RIBONUCLEASE PROTEINS

[76] Inventors: Susanna M. Rybak, 7411B Round Hill Rd., Frederick, Md. 21702; Dianne L. Newton, 15904 New Bedford Dr., Rockville, Md. 20855; Lluis Boque, 187 Greenway Dr.; Alexander Wlodawer, 5512 Bootjack Dr., both of Frederick, Md. 21702

[21] Appl. No.: 08/875,811

[22] PCT Filed: Feb. 19, 1997

[86] PCT No.: PCT/US97/02588

§ 371 Date: Feb. 19, 1998

§ 102(e) Date: Feb. 19, 1998

[87] PCT Pub. No.: WO97/31116

PCT Pub. Date: Aug. 28, 1997

Related U.S. Application Data

[63] Continuation of application No. 06/011,800, filed as application No. PCT/US97/02588, Feb. 19, 1997.

[51] Int. Cl.[7] .............................. A61K 38/46; C12N 9/22; C12N 15/00; C07H 21/04
[52] U.S. Cl. ..................... 424/94.6; 435/199; 435/252.3; 435/254.11; 435/320.1; 435/325; 536/23.2
[58] Field of Search ................................. 435/199, 252.3, 435/254.11, 325, 320.1; 536/23.2; 424/94.6

[56] References Cited

PUBLICATIONS

Ardelt et al., *J. Biol. Chem.*, 266(1): 245–251, Jan. 5, 1991.
Newton et al. *J. Biol. Chem.*, 269(43): 26739–26745, Oct. 28, 1994.

*Primary Examiner*—Karen Cochrane Carlson
*Assistant Examiner*—Einar Stole
*Attorney, Agent, or Firm*—Townsend and Townsend and Crew LLP

[57] ABSTRACT

The invention relates to ribonucleases derived from a native ribonuclease found in the oocytes of *Rana pipiens*. Various humanized and recombinant forms of these molecules are described as well as uses for them.

31 Claims, 7 Drawing Sheets

| | | | | | | |
|---|---|---|---|---|---|---|
| ONCONASE | EDWLTFQKKH | ITNTRDVDCD | NIMSTNLFHC | KDKNTFIYSR | PKPVKAICKG | 50 |
| RANA CLONE 9 | .......... | ......DVDCD | NIMSTNLFHC | KDKNTFIYSR | PKPVKAICKG | 35 |
| ONCONASE | IIASKNVLTT | SKFYLSDCNV | TSRPCKYKLK | KSTNKFCVTC | KNQAPVHFVG | 100 |
| RANA CLONE 9 | IIASKNVLTT | SKFYLSDCNV | TSRPCKYKLK | KSTNKFCVTC | KNQAPVHF.. | 83 |
| ONCONASE | VGSC | | | | | 104 |
| RANA CLONE 9 | .... | | | | | 83 |

FIG. 1.

```
                 1                                                            *                                    50
FROG LECTIN      .....enwat  FqqkHi.int  piin....Cn  tiMdnniyiv  ggqCKrvNTF
ONCONASE         .....edwlt  FqkkHi.tnt  rdvd.....Cd  niMstnlf..  ..hCKdkNTF
EDN              kppqftwaqw  FetqHinxts  qq.......Ct  naMqvinnyq  rr.CKnqNTF
ECP              rppqftraqw  FaiqHislnp  pr.......Ct  iaMrainnyr  wr.CKnqNTF
ANG              .aqddyryih  FltqHyd.ak  pkgrndeyCf  hmMknrrltr  p..CKdrNTF
SIMINAL          ..kes.aaak  FerqHmdsgn  spsssnyCn   lmMccrkmtq  gk.CKpvNTF
RNASE A          ..ket.aaak  FerqHmdsst  saasssnyCn  qmMksrnltk  dr.CKpvNTF 51                                                                               100
FROG LECTIN      iissattvka  iCtgvi..nm  nvl.......  SttrfqlntC  trts...ftp
ONCONASE         iysrpepvka  iCkgii.ask  nvlt......t  Sefy..lsdC  .....nvts
EDN              llttfanvvn  vCgnpnmtcp  snktrknchh  SgsqvplihC  nlttpspqni
ECP              lrttfanvvn  vCgnqsircp  hnrtlnnchr  SrfrvplihC  dlinpgaqni
ANG              ihgnkndika  iCedrngqpy  rg...dlri   SksefqitiC  khkggs..sr
SIMINAL          vhesladvka  vCsqkkvtck  ngqt..ncyq  SkstmritdC  ret..gssky
RNASE A          vheslandvqa vCsqknvack  ngqt..ncyq  SystmsitdC  ret..gssky 101                                              *                               150
FROG LECTIN      rpCpYssrte  tnyicVkCen  q.........  ..yPVHfagi  grcp......
ONCONASE         rpCkYklkks  tnkfcVtCen  q.........  ..aPVHfvgv  gsc.......
EDN              snCrYaqtpa  nmfyiVaCdn  rdqrrdppqy  pvvPVHldri  f.........
ECP              snCrYadrpg  rrfyvVaCdn  rd.prdspry  pvvPVHldtt  f.........
ANG              ppCrYgated  srvivVgCen  g.........  ..lPVHfdes  fitprn....
SIMINAL          pnCaYkttqv  ekhiiVaCgg  k.........  psvPVHfdas  v.........
RNASE A          pnCaYkttqa  nkhiiVaCeg  n.........  pyvPVHfdas  v.........
```

FIG. 4.

RECOMBINANT RIBONUCLEASE PROTEINS

This is a National Stage Application of PCT/US97/02588, filed Feb. 19, 1997 and a continuation of Provisional Application No. 06/011,800 filed Feb. 21, 1996.

FIELD OF THE INVENTION

This invention relates to the production of ribonuclease molecules which are toxic to cells of interest.

BACKGROUND OF THE INVENTION

Ribonucleases such as ribonuclease A ("RNase A") and their cytotoxicity toward tumor cells are well documented from studies performed in the 1960s and 1970s and reviewed in Roth, J., 1963, Cancer Res. 23:657–666. Human serum was also discovered to contain several RNases (Reddi, E., 1975, Biochem. Biophys. Res. Commun. 67:110–118, Blank et al., Human body fluid ribonucleases: detection, interrelationships and significance 1-203–209 (IRL Press, London, 1981)) that are expressed in a tissue specific manner. The proteins involved in the host defense activity of the eosinophil are homologous to RNases and express RNase activity (Gleich et al., 1986, Proc. Natl. Acad. Sci., USA 83:3146–3150; Slifman et al., 1986, J. Immunol, 137:2913–2917). Thus, human serum RNases were believed to also have host defense activities.

Further to these early studies was the discovery that an anti-tumor protein from oocytes of Rana pipiens has homology to RNase A (Ardelt et al., 1991, J. Biol. Chem. 266:245–251). This protein has been termed ONCONASE®, Alfacell Corporation, N.J. See also e.g., Darzynkiewicz et al. (1988) Cell Tissue Kinet. 21, 169–182, Mikulski et al. (1990) Cell Tissue Kinet. 23, 237–246. This protein is also described in U.S. Pat. No. 4,888,172. Phase I and Phase I/II clinical trials of ONCONASE® as a single therapeutic agent in patients with a variety of solid tumors (Mikulski et al. (1993) Int. J. of Oncology 3, 57–64) or combined with tamoxifen in patients with advanced pancreatic carcinoma have recently been completed (Chun et al. (1995) Proc Amer Soc Clin Oncol 14 No. 157, 210). Conjugation of ONCONASE® to cell-type-specific ligands increased its potency towards tumor cells (Rybak et al. (1993) Drug Delivery 1, 3–10). Taken together, these results indicate that ONCONASE® has properties that are advantageous for the generation of a potent selective cell killing agent.

However, since this is not a human-derived protein, it is prone to stimulating undesirable immune responses when used in humans. Thus, it would be desirable to retain the potent cytotoxic properties of this molecule while reducing its immunogenicity in humans. Further, it would be desirable to produce derivations of this molecule recombinantly so that it may be better chemically conjugated or recombinantly joined to other molecules for targeting to specific cells. Until the invention described herein, it has proven difficult to recombinantly express an active cytotoxic molecule related to ONCONASE®. Though it was thought that the methionine-glutamic acid amino terminal end of the recombinant molecule prohibited the molecule from having significant enzymatic activity, a means to solve this problem has not been forthcoming until the invention herein.

Further, although advances in protein design techniques promise to alleviate some of the immunogenicity associated with the antibody portion of immunotoxins (Bird et al., 1988, Science 242:423; Huston et al., 1988, Proc Natl Acad Sci USA 85:5879; Ward et al., 1989, Nature 341:544), no solution has been forthcoming for the immunogenicity of the toxin portion other than immunosuppression of the patients (Khazaeli et al., 1988, Proceedings of AACR 29:418). Thus, there is a continuing need for methods and compositions that would reduce the immunogenicity of the Rana pipiens-derived toxic moiety.

Non-cytotoxic human members of the RNase A superfamily linked to tumor associated antigens by chemical (Rybak et al.(1991) J. Biol. Chem 266, 1202–21207, Newton et al. (1992) J. Biol. Chem. 267, 19572–19578) or recombinant means (Rybak et al. Proc. Natl. Acad. Sci. U.S.A. 89, 3165, Newton et al. (1994) J Biol Chem. 269, 26739–26745 have been shown to offer a strategy for selectively killing tumor cells with less immunogenicity than current strategies employing plant and bacterial toxins Rybak, S. M. & Youle, R. J. (1991) Immunol. and Allergy Clinics of North America 11:2, 359–380. Human-derived ribonucleases of interest include eosinophil-derived neurotoxin (EDN) and angiogenin.

SUMMARY OF THE INVENTION

We have discovered how to construct RNases which are highly cytotoxic and which are modifications of the native ONCONASE® (nOnc). When the nOnc was expressed recombinantly it was not found to have significant cytotoxicity. Our modified versions (rOnc), however, are highly cytotoxic and otherwise retain the advantages of the native ONCONASE® molecules, while in some cases they also have increased cytotoxic properties. The rOnc molecules may be used alone or conveniently used to form chemical conjugates, as well as to form targeted recombinant immunofusions. These rOnc molecules can be used to decrease tumor cell growth. An effective recombinant form of nOnc advantageously permits the recombinant molecule to be fused to other therapeutic or targeting molecules of interest recombinantly. Further, the rOnc molecule can be modified to enhance cytotoxicity as will be seen below. Our nOnc-derived molecules are also desirable because nOnc is a unique ribonuclease in that it can be administered alone directly to patients to decrease and inhibit tumor cell growth without the use of a targeting agent.

The present invention also includes methods of selectively killing cells using a rOnc joined to a ligand to create a selective cytotoxic reagent of the present invention. The method comprises contacting the cells to be killed with a cytotoxic reagent of the present invention having a ligand binding moiety that specifically delivers the reagent to the cells to be killed. This method of the present invention may be used for cell separation in vitro by selectively killing unwanted types of cells, for example, in bone marrow prior to transplantation into a patient undergoing marrow ablation by radiation, or for killing leukemia cells or T-cells that would cause graft-versus-host disease. The toxins can also be used to selectively kill unwanted cells in culture.

Humanized versions of our rOnc molecules are also described which graft portions of mammalian or human-derived RNases such as angiogenin or human eosinophil derived neurotoxin (EDN) to the rOnc-derived molecules. A preferred embodiment of the invention is a molecule where the amino terminal end of EDN is placed onto the amino terminal end of the rOnc molecules. The surprising properties of these hybrid proteins with regard to ribonuclease activity and in vitro anti-tumor effects are described.

BRIEF DESCRIPTION OF THE DRAWINGS

FIGURE LEGENDS

FIG. 1 shows the deduced amino acid sequence of the Rana clone 9 (SEQ ID NO:2), described below and sequence alignment with the amino acid sequence of nOnc (SEQ ID NO:1). The bold print indicates identical residues between nOnc and Rana clone 9. The dots indicate missing amino acids in the PCR clone.

Figure 2A:
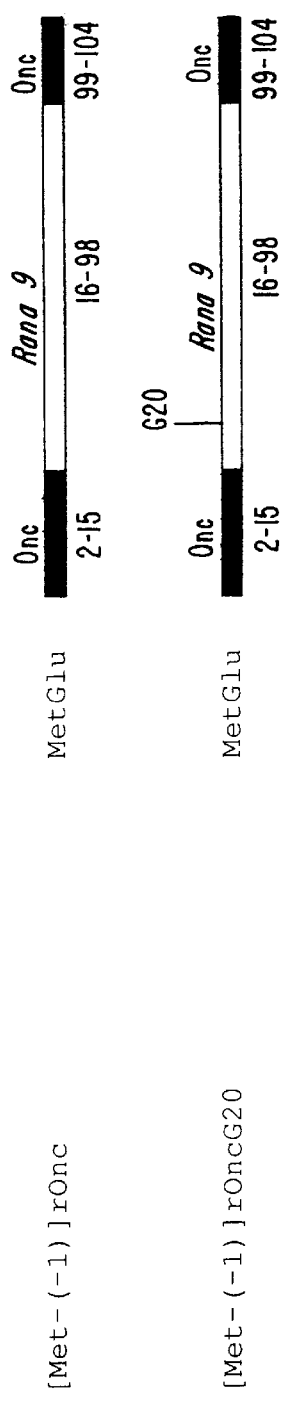
Figure 2B:
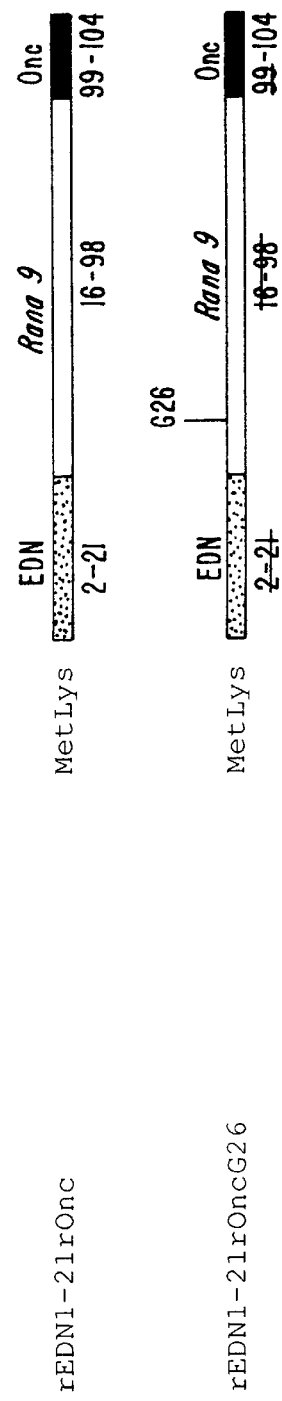

FIGS. 2A and 2B show the configuration of the DNA constructs exemplified in the examples. The PCR product obtained from Rana pipiens DNA is identified as Rana 9. The N-and C-termini are synthetically filled in and identified as Onc in the constructs encoding [Met-(-1)]rOnc or EDN for the N-terminal EDN/Onc hybrid. Corresponding amino acid residues are indicated below each construct. FIG. 2B shows the sequence alignment of the N-terminal sequences of nOnc (SEQ ID NO:3), rEDN (SEQ ID NO:4), [Met-(-1)]rOnc containing a Gly (G) instead of Asp in position 20 (SEQ ID NO:5), rEDN$_{(1-21)}$rOnc with an Asp in amino acid position 26 (SEQ ID NO:6) and rEDN$_{(1-21)}$rOncG26 with a Gly in position 26 (SEQ ID NO:7). Bold letters indicate conserved residues, capital letters show the sequence deduced from Rana clone 9.

Figure 3A:
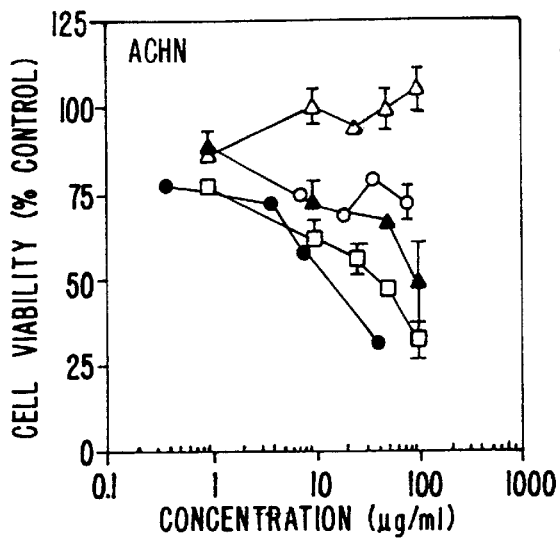
Figure 3B:
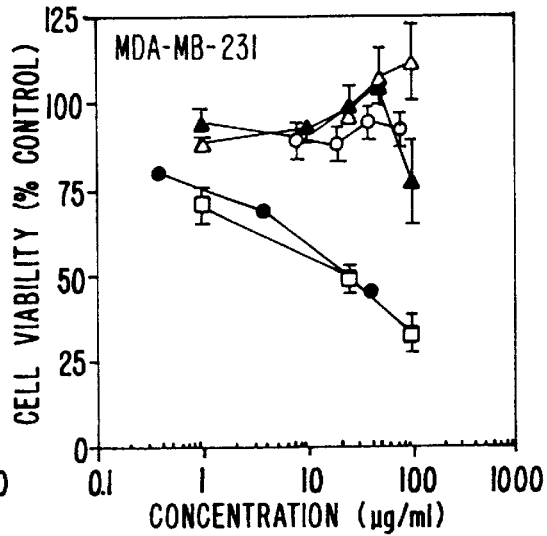
Figure 3C:
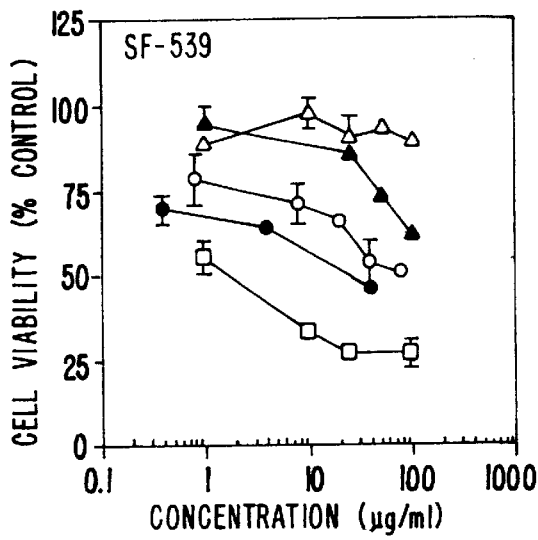
Figure 3D:
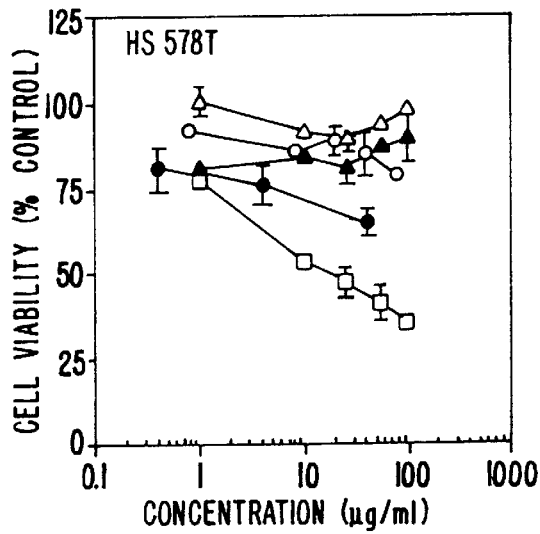

FIGS. 3A–3D show the inhibition of protein synthesis in human tumor cells by nOnc, rEDN, [Met-(-1)]rOnc or hybrid proteins. Cells ($10^4$) were plated in individual 96-well microtiter culture plates and treated with varying concentrations of each agent for 48 h. Cell viability was determined as described in the Example Section below. Results from more than one individual experiment were combined to yield the mean data points. Standard errors of the means, when they are greater than the symbol, are shown. Cell lines: ACHN, renal cancer (FIG. 3A); MDA-MB-231 (FIG. 3B) and HS 578T (FIG. 3D), breast cancer; SF-539 (FIG. 3C), CNS, cancer. EDN (open triangles); nOnc (open squares); [Met-(-1)]rOnc, (solid triangles); rEDN$_{(1-21)}$rOnc, (open circles); rEDN$_{(1-21)}$rOncG26 (solid circles).

FIG. 4 shows a sequence alignment of some members of the RNase A superfamily: Frog lectin is from Rana catesbeiana, ONCONASE®, EDN, ECP (human eosinophil cationic protein), Ang is bovine angiogenin, Seminal is bovine seminal RNase, and RNase A is bovine pancreatic RNase A (SEQ ID NOs:8, 1 and 9–13, respectively). Amino acids conserved in all members are capitalized, and active site residues H12, K41, and H119 (RNase A numbering) are marked with an asterisk.

Figure 5:
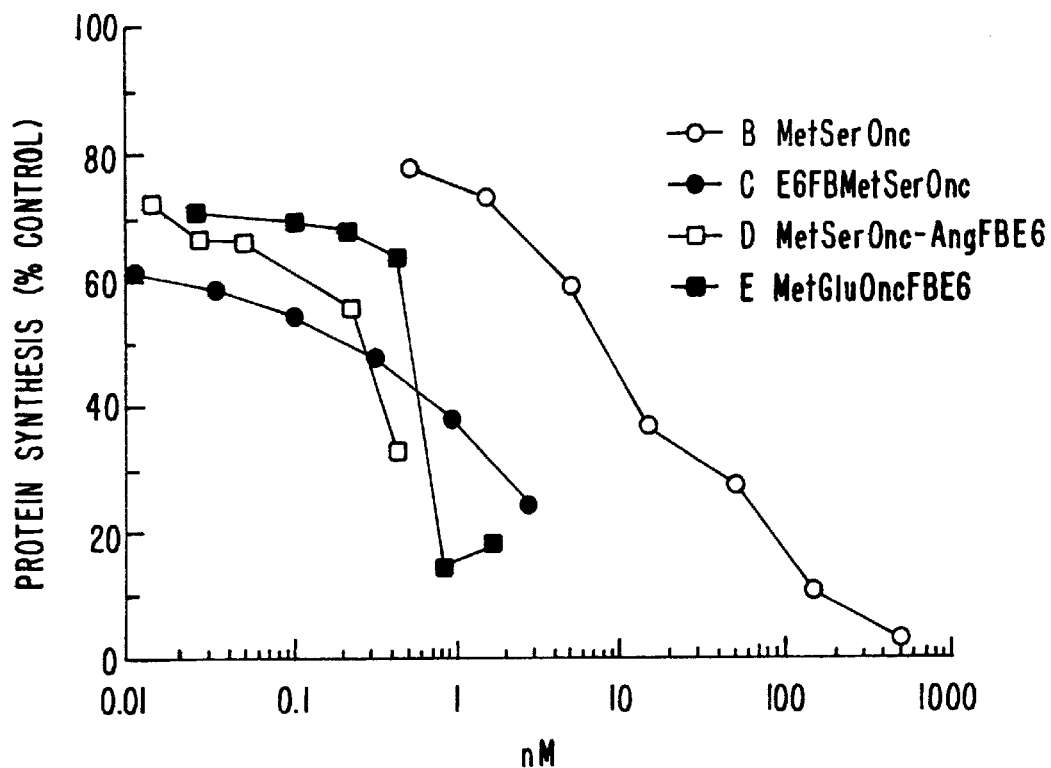

FIG. 5 shows the inhibition of protein synthesis by MetSerOnc and MetSer- or MetGlu-OncFvs. The cytotoxic effect of the single chain antibody rOnc fusion proteins; E6FB[Met-(-1)]SerrOnc (closed circles), [Met-(-1)]SerrOncAngFBE6 (open squares) and [Met-(-1)]GlurOncFBE6 (closed squares) were compared to the non-targeted recombinant protein, [Met-(-1)]SerrOnc (open circles), by determining inhibition of protein synthesis in SF 539 cells. Cells were plated into 96-well microtiter plates in Dulbecco's minimum essential medium supplemented with 10% heat-inactivated fetal bovine serum. Additions were made in a total volume of 10 μl and the plates were incubated at 37° for 3 days. Phosphate buffered saline containing 0.1 mCi of [$^{14}$C]leucine was added for 2–4 h and the cells were harvested onto glass fiber filters using a PHD cell harvester, washed with water, dried with ethanol and counted. The results were expressed as per cent of [$^{14}$C]leucine incorporation in the mock-treated wells.

Figure 6A:
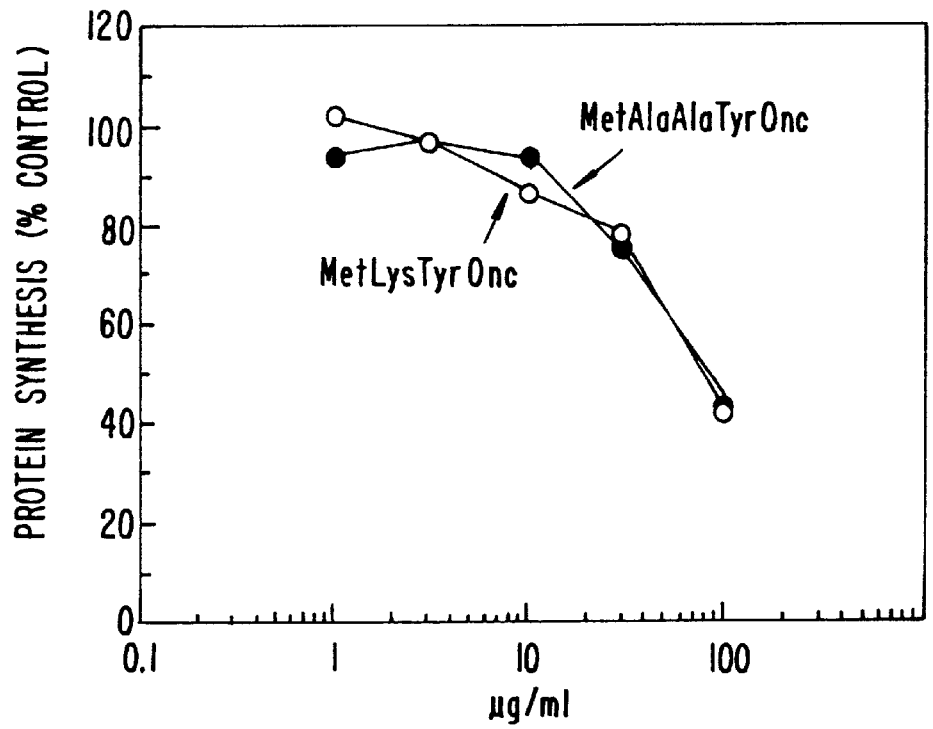
Figure 6B:
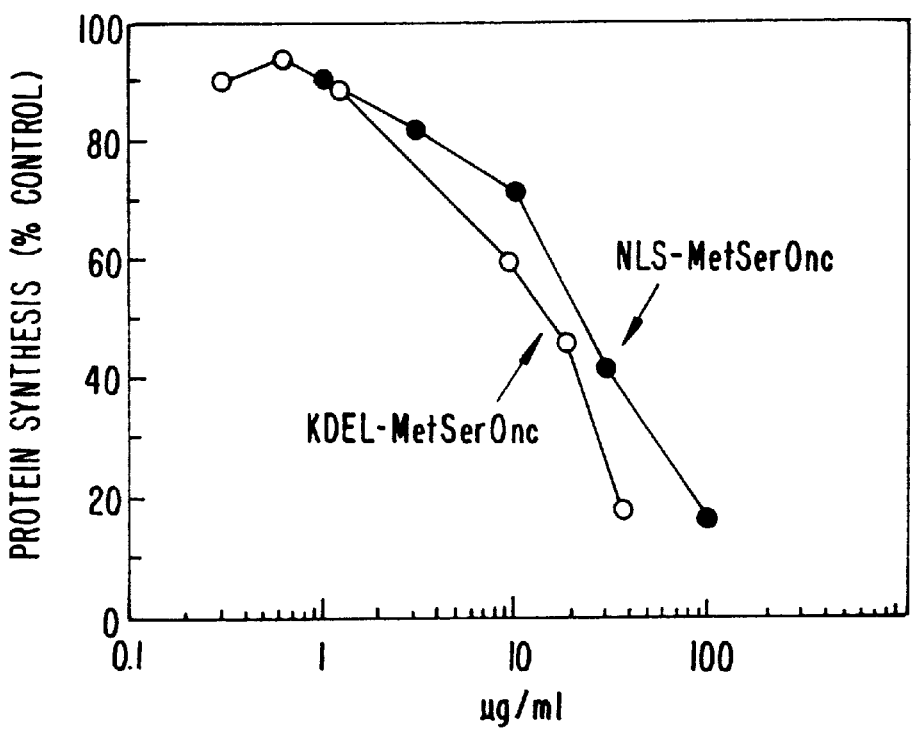

FIGS. 6A and 6B show inhibition of protein synthesis in an assay as described for FIGS. 3A–3D using cell line SF539, human glioma cells and rOnc fusion proteins designated MetLysTryrOnc (open circles, FIG. 6A); MetAlaAlaTyrOnc (closed circles, FIG. 6A); and rOnc fusion proteins with signal peptides, MetKDELSerrOnc (open circles, FIG. 6B) and MetNLSSerrOnc (closed circles FIG. 6B).

Figure 7:
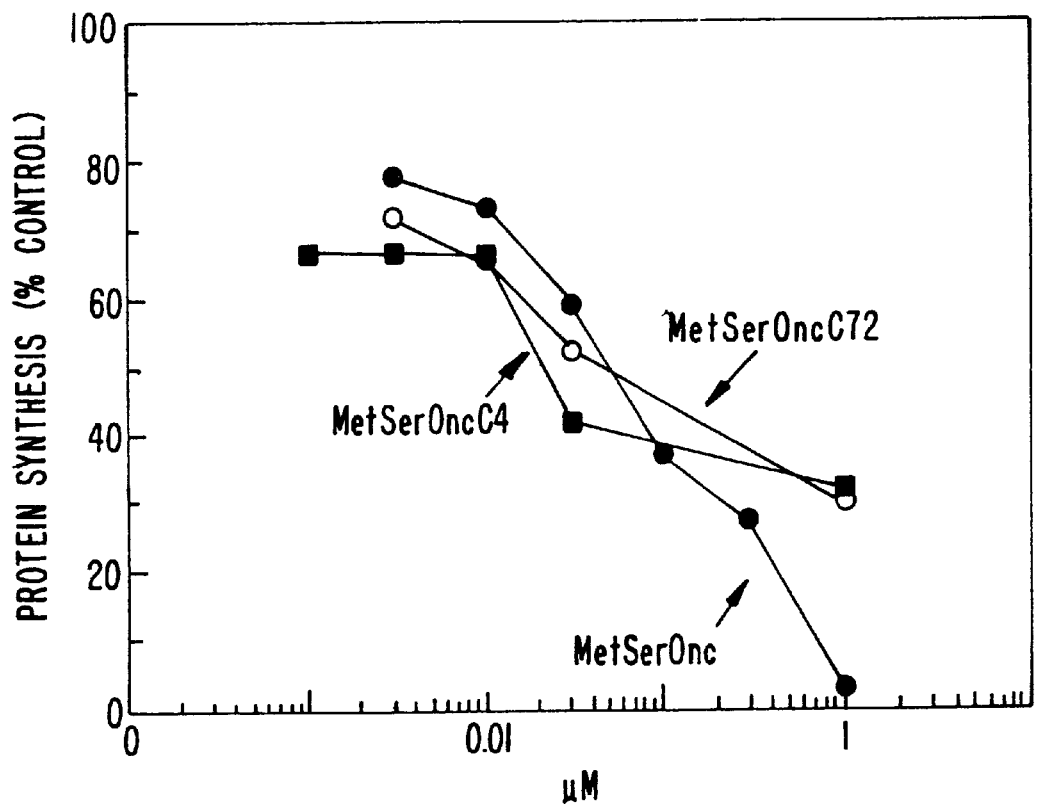

FIG. 7 shows inhibition of protein synthesis in an assay as described for FIGS. 3A–3D using cell line SF539, human glioma cells and comparing three fusion proteins corresponding to MetSerOnc (SEQ ID NO:39 with a Met-Ser amino terminal end): MetSerOnc (closed circles), MetSerOncC4 (MetSerOnc with a Cys at amino acid position 5 of SEQ ID NO:39, closed squares) and MetSerOncC72 (MetSerOnc with a Cys at amino acid position 73 of SEQ ID NO:39, open circles).

DETAILED DESCRIPTION

This invention provides highly active and cytotoxic ribonuclease molecules which can be used to selectively kill and target cells, particularly tumor cells. In some embodiments the molecules are designed to incorporate sequences from human derived ribonucleases which are also highly active and cytotoxic, but which have the further advantage in that they are less immunogenic in humans. The rOnc molecules of the present invention are those which are recombinant nOnc-derived sequences.

The nOnc molecule has an amino acid sequence set forth in SEQ ID NO:1. Bovine pancreatic RNase A has an amino acid sequence set forth in SEQ ID NO:13. Unless otherwise indicated, the amino acid sequence positions described herein use as a frame of reference the bovine pancreatic RNase A sequence in SEQ ID NO:13 as this is the reference sequence commonly used in the RNase field. It should be understood that such position designations do not indicate the number of amino acids in the claimed molecule per se, but indicate where in the claimed molecule the residue occurs when the claimed molecule sequence is aligned with bovine RNase.

The rOnc molecules described and claimed herein will preferably have cysteine residues at amino acid positions corresponding to amino acid positions 26, 40, 58, 84, 95 and 110; a lysine at position 41 and a histidine at position 119 with reference to the bovine RNase A, SEQ ID NO:13 (such positions correspond to amino acid position numbers 19, 30, 48, 68, 75 and 90 and 87 and 104 of the nOnc sequence respectively set out in SEQ ID NO:1).

The rOnc molecules of this invention are those that have measurable ribonuclease activity, as defined below. The ribonucleases will also have (a) an amino terminal end beginning with a methionine which is followed by any amino acid other than glutamic acid (Glu); (b) a cysteine at amino acid positions 26, 40, 58, 84, 95 and 110; a lysine at position 41 and a histidine at position 119, such positions being determined with reference to those in the amino acid sequence of bovine RNase A (SEQ ID NO:13), and (c) an nOnc-derived amino acid sequence.

Preferably, the rOnc molecules will have an amino terminal end selected from the group consisting of:
Met-Ala;
Met-Ala-Ala-Ser;
Met-Arg;
Met-(J);
Met-Lys-(J);
Met-Arg-(J);
Met-Lys;
Met-Lys-Pro;
Met-Lys-(J)-Pro (SEQ ID NO:14);
Met-Lys-Pro-(J) (SEQ ID NO:15);
Met-Asn;

Met-Gln;
Met-Asn-(J);
Met-Gln-(J);
Met-Asn-(J)-Pro (SEQ ID NO:16);
Met-(J)-Lys;
Met-(J)-Lys-Pro (SEQ ID NO:17); and
Met-(J)-Pro-Lys (SEQ ID NO:18);
where (J) is Ser, Tyr or Thr.

Further, it is preferred that the rOnc molecules be modified so that the aspartic acid of amino acid position 2 of nOnc (position 4 with reference to the sequence of bovine RNase A) is deleted or replaced by Ala or Asn.

In alternative forms of the rOnc molecules, the molecules will employ an amino terminal end encoded by a sequence derived from the amino terminal end of EDN followed by a sequence from rOnc. In such forms, it is preferred that the amino acid sequence is one selected from the group consisting of those sequences substantially identical to those of a formula:

$$Met(-1)EDN_{(1-m)}Onc_{(n-104)}$$

wherein Met(-1) refers to an amino terminal residue of Met; wherein $EDN_{(1-m)}$ refers to a contiguous sequence of amino acids of a length beginning at amino acid position 1 of EDN (SEQ ID NO:9) and continuing to and including amino acid position "m" of EDN; wherein $Onc_{(n-104)}$ refers to a sequence of contiguous amino acids beginning at amino acid position "n" and continuing to and including amino acid position 104 as set out in SEQ ID NO:1; such that:

when m is 21, n is 16 or 17;
when m is 22, n is 17;
when m is 20, n is 16;
when m is 19, n is 15;
when m is 18, n is 14;
when m is 17, n is 12 or 13;
when m is 16, n is 11, 12, 13 or 14;
when m is 15, n is 10;
when m is 14, n is 9;
when m is 13, n is 8; and
when m is 5, n is 1.

In other alternative embodiments, the rOnc molecule will be fused at the carboxyl end to a sequence from angiogenin, such as the sequence exemplified in SEQ ID NO:11 or that at amino acid positions 101 to 107 of SEQ ID NO:20. The nucleic acid sequence for human angiogenin is known and is set out in U.S. patent application Ser. No. 08/125,462.

Preferred rOnc nucleic acid sequences are those that encode preferred rOnc amino acid sequences which are substantially identical to those in SEQ ID NOs:20, 22, 24, 26, 28 and 30 (corresponding nucleic acid sequences are set out in SEQ ID NOs:19, 21, 23, 25, 27 and 29, respectively). Most preferred rOnc amino acid sequences are those that are substantially identical to those set forth in SEQ ID NOs:20, 22, 24 and 26. Their corresponding nucleic acid sequences are also preferred and are set out in SEQ ID NOs:19, 21, 23 and 25, including conservatively modified variants thereof. The most preferred sequence includes SEQ ID NO:22, one which employs an amino terminal end comprising 1 to 21 (typically 21) amino acids of the amino terminal end of EDN grafted on to 16 to 104 amino acids of the nOnc sequence, with amino acid residue 20 in nOnc (Asp) being replaced with Gly. Preferred rOnc sequences further will contain optionally a Cys at a position corresponding to amino acid position 5, or 73 or Ala at amino acid position 88 in place of Cys with reference to SEQ ID NO:39.

Comparisons of the rOnc sequences provided here can be made to described sequences in the pancreatic RNase A superfamily. Many of such members are known and include, but are not limited to, frog lectin from *Rana catesbeiana* (Titani et al., *Biochemistry* 26:2189 (1987)); ONCONASE® (Ardelt, W. et al., *J. Biol. Chem.* 266:245 (1991)); eosinophil derived neurotoxin (EDN) (Rosenberg et al., supra); human eosinophil cationic protein (ECP) (Rosenberg et al., *J. Exp. Med.* 170:163 (1989)); angiogenin (Ang) (Fett, J. W. et al., *Biochemistry* 24:5480 (1985)); bovine seminal RNase (Preuss et al., *Nuc. Acids. Res.* 18:1057 (1990)); and bovine pancreatic RNase (Beintama et al., *Prog. Biophys. Mol. Biol.* 51:165 (1988)), references for all such proteins are incorporated by reference herein. Amino acid sequence alignment for such RNases are also set out in FIG. 4 and in Youle et al., *Crit. Rev. Ther. Drug. Carrier Systems* 10:1–28 (1993) and in U.S. patent application Ser. No. 08/125,462, which is incorporated by reference herein.

DEFINITIONS

Unless defined otherwise herein, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York), and Hale and Marham (1991) *The Harper Collins Dictionary of Biology*, Harper Perennial, NY provide one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "measurable ribonuclease activity" or "significant ribonuclease activity" refer to a molecule which has an $IC_{50}$ (ng/ml) of less than 40 when added to a rabbit reticulocyte lysate assay wherein protein synthesis is inhibited as measured by the incorporation of [$^{35}$S]methionine into acid precipitable protein. $IC_{50}$ is the concentration of protein necessary to inhibit protein synthesis by 50% in the assay. The lysate assay may be done as described in the Promega lysate assay kit which is commercially available from Promega Corporation, Madison, Wis. Ribonuclease activity using high molecular weight RNA and tRNA is determined at 37° C. through the formation of perchloric acid soluble nucleotides following published protocols (Newton, D. L., et al. (1996) *Biochemistry* 35:545–553). With poly(A,C) UpG and poly U, ribonuclease activity is assayed according to DePrisco et al., and Libonati and Floridi (DePrisco, R., et al. (1984) *Biochimica et Biophysica Acta* 788:356–363; Libonati, M. et al. (1969) *European J. Biochem.* 8:81–87). Activity is assayed by measuring the increase with time in absorbance at 260 nm. Incubation mixtures (1 ml of 10 mM imidazole, 0.1 M NaCl, pH 6.5 or pH 7) contain substrate and appropriate amounts of enzyme solution at 25° C. The in vitro translation assay (St. Clair, D. K., et al. (1987) *Proc. Natl. Acad. Sci.* 84:8330–8334) and the cell viability assays using the (3-[4,5-Dimethylthiazol-2-yl]-2,5-diphenyltetrazolium bromide; Thiazolyl blue) (MMT) (Mossman, T. (1983) *J. Immunol. Methods* 65:55–63) are performed as previously described (Pearson, J. W., et al. (1991) *J. Natl. Cancer Inst.* 83:1386–1391).

An "nOnc-derived" amino acid sequence is one that contains at least one string of six contiguous amino acids which is identical to a contiguous sequence of six amino acids selected from the group of sequences beginning at amino acid positions 1 (with Glu replacing pyroGlu), 2, 3, 4, 5, 6, 7, 8, 11, 12, 13, 14, 15, 16, 18, 19, 20, 22, 23, 24, 25, 26, 27, 28, 29, 30, 31, 32, 33, 34, 35, 36, 37, 41, 42, 43, 44, 45, 46, 47, 50, 52, 54, 56, 59, 60, 61, 62, 63, 64, 65, 66, 67, 68, 69, 70, 71, 72, 73, 74, 76, 80, 81, 82, 84, 85, 86, 87, 91, 92, 93, 95, or 96 of the nOnc amino acid sequence (SEQ ID NO:1).

"Conservatively modified variations" of a particular nucleic acid sequence refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence. Furthermore, one of skill will recognize that individual substitutions, deletions or additions which alter, add or delete a single amino acid or a small percentage of amino acids in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

The terms "isolated" or "biologically pure" refer to material which is substantially or essentially free from components which normally accompany it as found in its naturally occurring environment. The isolated material optionally comprises material not found with the material in its natural environment. The rOncs described herein are isolated and biologically pure since they are recombinantly produced in the absence of unrelated *Rana pipiens* proteins. They may, however, include heterologous cell components, a ligand binding moiety, a label and the like.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof. A nucleic acid encodes another nucleic acid where it is the same as the specified nucleic acid, or complementary to the specified nucleic acid.

An "expression vector" includes a recombinant expression cassette which includes a nucleic acid which encodes a rOnc polypeptide which can be transcribed and translated by a cell. A recombinant expression cassette is a nucleic acid construct, generated recombinantly or synthetically, with a series of specified nucleic acid elements which permit transcription of a particular nucleic acid in a target cell. The expression vector can be part of a plasmid, virus, or nucleic acid fragment. Typically, the recombinant expression cassette portion of the expression vector includes a nucleic acid to be transcribed, and a promoter.

The term "recombinant" when used with reference to a protein indicates that a cell expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means, for example under the control of a heterologous promoter.

The term "subsequence" in the context of a particular nucleic acid or polypeptide sequence refers to a region of the nucleic acid or polypeptide equal to or smaller than the particular nucleic acid or polypeptide. "Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, New York. Generally, highly stringent wash conditions are selected to be about 5° C. lower than the thermal melting point ($T_m$) for the specific sequence at a defined ionic strength and ph. The $T_m$ is the temperature (under defined ionic strength and pH) at which 50% of the target sequence hybridizes to a perfectly matched probe. Very stringent conditions are selected to be equal to the $T_m$ point for a particular probe. Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "identical" in the context of two nucleic acid or polypeptide sequences refers to the residues in the two sequences which are the same when aligned for maximum correspondence over a specified comparison window. When percentage of sequence identity is used in reference to proteins or peptides it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4: 11–17 (1988) e.g., as implemented in the program PC/GENE (Intelligenetics, Mountain View, Calif., U.S.A.).

Methods of alignment of sequences for comparison are well-known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol.* 48: 443; by the search for similarity method of Pearson and Lipman (1988) *Proc. Natl. Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., U.S.A.); the CLUSTAL program is well described by Higgins and Sharp (1988) *Gene*, 73: 237–244 and Higgins and Sharp (1989) *Computer Applications in the Biosciences* 5: 151–153; Corpet, et al. (1988) *Nucleic Acids Research* 16, 10881–90; Huang, et al. (1992) *Computer Applications in the Biosciences* 8, 155–65, and Pearson, et al. (1994) *Methods in Molecular Biology* 24, 307–31. Alignment is also often performed by inspection and manual alignment.

The term "substantial identity" or "substantial similarity" in the context of a polypeptide indicates that a polypeptide comprises a sequence with at least 70% sequence identity to a reference sequence, or preferably 80%, or more preferably 85% sequence identity to the reference sequence, or most preferably 90% identity over a comparison window of about 10–20 amino acid residues. An indication that two polypeptide sequences are substantially identical is that one peptide is immunologically reactive with antibodies raised against the second peptide. Thus, a polypeptide is substantially identical to a second polypeptide, for example, where the two peptides differ only by a conservative substitution.

One indication that two nucleic acid sequences are substantially identical is that the polypeptide which the first nucleic acid encodes is immunologically cross reactive with the polypeptide encoded by the second nucleic acid.

Another indication that two nucleic acid sequences are substantially identical is that the two molecules hybridize to each other under stringent conditions. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. However, nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule. Specific delivery typically results in greater than 2 fold, preferably greater than 5 fold, more preferably greater than 10 fold and most preferably greater than 100 fold increase in amount of delivered molecule (per unit time) to a cell or tissue bearing the target molecule as compared to a cell or tissue lacking the target molecule or marker.

The term "residue" as used herein refers to an amino acid that is incorporated into a polypeptide. The amino acid may be a naturally occurring amino acid and, unless otherwise limited, may encompass known analogs of natural amino acids that can function in a similar manner as naturally occurring amino acids.

A "fusion protein" or when a molecule is "joined" to another refers to a chimeric molecule formed by the joining of two or more polypeptides through a peptide bond formed between the amino terminus of one polypeptide and the carboxyl terminus of another polypeptide. The fusion protein or the joined molecules may be formed by the chemical coupling of the constituent molecules or it may be expressed as a single polypeptide from a nucleic acid sequence encoding a single contiguous fusion protein. A single chain fusion protein is a fusion protein having a single contiguous polypeptide backbone.

A "ligand" or a "ligand binding moiety", as used herein, refers generally to all molecules capable of specifically delivering a molecule, reacting with or otherwise recognizing or binding to a receptor on a target cell. Specifically, examples of ligands include, but are not limited to, antibodies, lymphokines, cytokines, receptor proteins such as CD4 and CD8, solubilized receptor proteins such as soluble CD4, hormones, growth factors, and the like which specifically bind desired target cells.

Making rOnc-derived Nucleic Acids and Polypeptides

Several specific nucleic acids encoding rOnc-derived polypeptides are described herein. These nucleic acids can be made using standard recombinant or synthetic techniques. Given the nucleic acids of the present invention, one of skill can construct a variety of clones containing functionally equivalent nucleic acids, such as nucleic acids which encode the same polypeptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acid compositions of this invention, whether RNA, cDNA, genomic DNA, or a hybrid of the various combinations, are isolated from biological sources or synthesized in vitro. The nucleic acids of the invention are present in transformed or transfected cells, in transformed or transfected cell lysates, or in a partially purified or substantially pure form.

In vitro amplification techniques suitable for amplifying sequences for use as molecular probes or generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook et al. (1989) *Molecular Cloning—A Laboratory Manual* (2nd Ed) Vol. 1–3; and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039.

Oligonucleotides for use as probes, e.g., in in vitro rOnc nucleic acid amplification methods, or for use as nucleic acid probes to detect rOnc nucleic acids are typically synthesized chemically according to the solid phase phosphoramidite triester method described by Beaucage and Caruthers (1981), *Tetrahedron Letts.*, 22(20):1859–1862, e.g., using an automated synthesizer, e.g., as described in Needham-VanDevanter et al. (1984) *Nucleic Acids Res.*, 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

One of skill will recognize many ways of generating desired alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook et al. (1989) *Molecular Cloning—A Laboratory Manual* (2nd Ed) Vol. 1–3; Innis, Ausbel, Berger, Needham VanDevanter and Mullis (all supra).

Polypeptides of the invention can be synthetically prepared in a wide variety of well-known ways. Polypeptides of relatively short size are typically synthesized in solution or on a solid support in accordance with conventional techniques. See, e.g., Merrifield (1963) *J. Am. Chem. Soc.* 85:2149–2154. Various automatic synthesizers and sequencers are commercially available and can be used in accordance with known protocols. See, e.g., Stewart and Young (1984) *Solid Phase Peptide Synthesis*, 2d. ed., Pierce Chemical Co. Polypeptides are also produced by recombinant expression of a nucleic acid encoding the polypeptide followed by purification using standard techniques.

Making Conservative Modifications of the Nucleic Acids and Polypeptides of the Invention One of skill will appreciate that many conservative variations of the sequences disclosed yield a substantially identical rOnc. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. Similarly, conservative amino acid substitutions, in one or a few amino acids in an amino acid sequence are substituted with different amino acids with highly similar properties (see, the definitions section, supra), are also readily identified as being highly similar to a disclosed amino acid sequence, or to a disclosed nucleic acid sequence which encodes an amino acid. Such conservatively substituted (or modified) variations of each explicitly disclosed sequence are a feature of the present invention.

One of skill will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97, Roberts et al. (1987) *Nature* 328:731–734 and Sambrook, Innis, Ausbel, Berger, Needham VanDevanter and Mullis (all supra).

Most commonly, polypeptide sequences are altered by changing the corresponding nucleic acid sequence and expressing the polypeptide. However, polypeptide sequences are also optionally generated synthetically using commercially available peptide synthesizers to produce any desired polypeptide (see, Merrifield, and Stewart and Young, supra).

One of skill can select a desired nucleic acid or polypeptide of the invention based upon the sequences provided and upon knowledge in the art regarding ribonucleases generally. The physical characteristics and general properties of RNases are known to skilled practitioners. The specific effects of some mutations in RNases are known. Moreover, general knowledge regarding the nature of proteins and nucleic acids allows one of skill to select appropriate sequences with activity similar or equivalent to the nucleic acids and polypeptides disclosed in the sequence listings herein. The definitions section herein describes exemplary conservative amino acid substitutions.

Finally, most modifications to nucleic acids and polypeptides are evaluated by routine screening techniques in suitable assays for the desired characteristic. For instance, changes in the immunological character of a polypeptide can be detected by an appropriate immunological assay. Modifications of other properties such as nucleic acid hybridization to a target nucleic acid, redox or thermal stability of a protein, thermal histeresis, hydrophobicity, susceptibility to proteolysis, or the tendency to aggregate are all assayed according to standard techniques.

rOnc Fusion Proteins and Other Therapeutic Moieties

The rOnc molecules may also include pharmacological agents or encapsulation systems containing various pharmacological agents. They typically will include a ligand to act as a targeting molecule to direct the rOnc to desired cells. The rOnc may be attached directly to a ligand or an antisense molecule which will assist in delivering the rOnc. See, for example, SEQ ID NOS:40–61. The rOnc can also be engineered to contain a nuclear localization signal ("NLS") such as that described in amino acid positions 1 to 7 in SEQ ID NO:32 (and SEQ ID NO:31) to direct the rOnc within the cell. Alternatively, the Met at position 8 and the corresponding nucleic acids at positions 22–24 of SEQ ID NO:31 has been and can be omitted. The nucleic acid sequence for the NLS is nucleic acids 1–21 of SEQ ID NO:31. A signal peptide is also exemplified at amino acid positions 1–25 of SEQ ID NO:63.

The rOnc molecules are uniquely adapted for gene therapy applications. They can be fused to other therapeutic agents, for example, they could be fused to an anti-B cell lymphoma antibody. For example, as will be explained in more detail below, rOnc molecules recombinantly fused to an anti-transferrin receptor antibody or an anti-colon cancer antibody were active. As mentioned above, nOnc has anti-tumor effects in vivo and preferentially kills rapidly dividing cells stimulated by serum or growth promoting agents such as ras. The molecules are readily internalized in the cell. Their activity can be further facilitated by joining them to a nuclear localization signal and the like to redirect the molecules within the cell. Of particular use in tumor cells would be to target telomerase, an enzyme subject to degradation by RNase.

We have found that Onc synergizes with ras in microinjection studies. This means that Onc and ras have to be together in the cell. Onc does not synergize with ras when it enters the cell via its own routing. A CAAX (SEQ ID NO:33) motif is required to localize ras at the plasma membrane (C=Cys, A=an aliphatic amino acid, X=S,M,C,A, or Q, an example is Cys-Val-Ile-Met (SEQ ID NO:34)). Importantly this type of sequence has been shown to target heterologous proteins to the plasma membrane (Hancock, J., Cadwallader, K., Paterson, H. and C. Marshall (1991) EMBO J. 10:4033). It would be desirable to join the rOnc gene with DNA encoding a CAAX (SEQ ID NO:33) signal as given in the example, or KDEL as described below.

Telomerase is being investigated as a "universal cancer target" (G. B. Morin, JNCI. (1995) 87:859). It is an RNA protein that is located in the nucleus. It has been shown that antisense to telomerase RNA can inhibit the function of the enzyme and block the growth of cancer cells (J. Feng et al., Science (1995) 269:1236). RNase can also destroy the activity of the enzyme. Onc can also destroy the activity of the enzyme when incubated with a cell extract containing telomerase. An NLS/Onc molecule (such as that set out in SEQ ID NO: 32) can be made to route Onc to the nucleus so that it can degrade telomerase. The NLS we used has been shown to redirect proteins to the nucleus for the aim of interfering with the function of a nuclear antigen (S. Biocca, M. S. Neuberger and A. Cattaneo, (1990) 9:101). Our NLS/Onc molecule is effective in killing cells.

An amino terminal sequence to the recombinant molecule may be preferred where it is desirable to translocate the molecule into the cytosol of target cells. Such signal peptide is typically inserted at the amino end of the protein. For example, the first amino acids of the recombinant molecules described herein (after Met) could be KDEL (SEQ ID NO:64) and would accomplish signalling the molecule to the endoplasmic reticulum. Amino acid sequences which include KDEL, repeats of KDEL, or other sequences that function to maintain or recycle proteins into the endoplasmic reticulum, referred to here as "endoplasmic retention sequences" may be employed.

Optionally, the rOnc molecule attached to a ligand may include an encapsulation system, such as a liposome or micelle that contains an additional therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735, Connor et al., *Pharm. Ther.*, 28: 341–365 (1985).

One of skill will appreciate that the ligand molecule or other therapeutic component and the rOnc molecule may be joined together in any order. Thus, where the ligand is a polypeptide, the rOnc molecule may be joined to either the amino or carboxy termini of the ligand or may also be joined to an internal region of either molecule as long as the attachment does not interfere with the respective activities of the molecules.

The molecules may be attached by any of a number of means well-known to those of skill in the art. Typically the rOnc will be conjugated, either directly or through a linker (spacer), to the ligand. However, where both the rOnc and the ligand or other therapeutic are polypeptides it is preferable to recombinantly express the chimeric molecule as a single-chain fusion protein.

In one embodiment, the rOnc molecule is chemically conjugated to another molecule (e.g. a cytotoxin, a label, a ligand, or a drug or liposome). Means of chemically conjugating molecules are well-known to those of skill.

The procedure for attaching an agent to an antibody or other polypeptide targeting molecule will vary according to the chemical structure of the agent. Polypeptides typically contain a variety of functional groups; e.g., carboxylic acid (COOH) or free amine (—NH$_2$) groups, which are available for reaction with a suitable functional group on an rOnc molecule to bind the other molecule thereto.

Alternatively, the ligand and/or rOnc molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join two molecules. The linker is capable of forming covalent bonds to both molecules. Suitable linkers are well known to those of skill in the art and include, but are not limited to, straight or branched-chain carbon linkers, heterocyclic carbon linkers, or peptide linkers. Where both molecules are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form a desired immunoconjugate. Alternatively, derivatization may involve chemical treatment of the ligand, e.g., glycol cleavage of the sugar moiety of a glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptides, such as antibodies or antibody fragments, are also known (See U.S. Pat. No. 4,659,839).

Many procedure and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071–4075 (1987) which are incorporated herein by reference. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982), Waldmann, *Science,* 252: 1657 (1991), U.S. Pat. Nos. 4,545,985 and 4,894,443 which are incorporated herein by reference.

In some circumstances, it is desirable to free the rOnc from the ligand when the chimeric molecule has reached its target site. Therefore, chimeric conjugates comprising linkages which are cleavable in the vicinity of the target site may be used when the effector is to be released at the target site. Cleaving of the linkage to release the agent from the ligand may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Production of rOnc Molecules or Fusion Proteins

Where the molecules of interest are relatively short (i.e., less than about 50 amino acids) they may be synthesized using standard chemical peptide synthesis techniques. Where two molecules of interest are relatively short the chimeric molecule may be synthesized as a single contiguous polypeptide. Alternatively the molecules may be synthesized separately and then fused by condensation of the amino terminus of one molecule with the carboxyl terminus of the other molecule thereby forming a peptide bond. Alternatively, the molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis;* pp. 3–284 in *The Peptides: Analysis, Synthesis, Biology. Vol.* 2: *Special Methods in Peptide Synthesis, Part A.,* Merrifield, et al. *J. Am. Chem. Soc.,* 85: 2149–2156 (1963), and Stewart et al., *Solid Phase Peptide Synthesis, 2nd ed.* Pierce Chem. Co., Rockford, Ill. (1984) which are incorporated herein by reference.

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins of this invention, as well as the rOnc molecules themselves, may be prepared by any suitable method, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.,* 22: 1859–1862 (1981); and the solid support method of U.S. Pat. No. 4,458,066, all incorporated by reference herein.

Chemical synthesis produces a single-stranded oligonucleotide. This may be converted into double-stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding fusion proteins or rOnc molecules of the present invention may be cloned using DNA amplification methods such as polymerase chain reaction (PCR). If two molecules are joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the rOnc molecules or the fusion proteins may be expressed in a variety of host cells, including *E. coli,* other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The expression vectors or plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant rOnc or fusion proteins can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology Vol. 182: Guide to Protein Purification.,* Academic Press, Inc. N.Y. (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

Accordingly, this invention also provides for host cells and expression vectors comprising the nucleic acid sequences described above.

Further, the present invention includes a method of selectively killing cells using a rOnc joined to a ligand to create a selective cytotoxic reagent of the present invention. The method comprises contacting the cells to be killed with a cytotoxic reagent of the present invention having a ligand binding moiety that specifically delivers the reagent to the cells to be killed. This method of the present invention may be used for cell separation in vitro by selectively killing unwanted types of cells, for example, in bone marrow prior to transplantation into a patient undergoing marrow ablation by radiation, for killing leukemia cells or T-cells that would cause graft-versus-host disease.

For methods of use in vivo, preferably the mammalian protein of the reagent used in this method is endogenous to the species in which the reagent is intended for use. Preferably, for use in humans, the cytotoxic reagent is a fusion protein comprising a humanized chimeric antibody and a humanized rOnc. Specific in vivo methods of this invention include a method for the chemotherapeutic alleviation of cancer in mammals comprising administering a cytotoxic amount of a selective cytotoxic reagent according to the present invention. The methods are particularly useful for treating tumors sensitive to the cytotoxic reagents. Tumors of particular interest include pancreatic, colon, breast and kidney tumors.

Pharmaceutical Compositions

The rOnc molecules and fusion proteins employing them of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the subject molecules and fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of therapeutic molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the present rOnc molecules or the fusion proteins or a cocktail thereof (i.e., with other proteins) can be administered for therapeutic treatments. In therapeutic applications, compositions are administered to a patient suffering from a disease, in a cytotoxic amount, an amount sufficient to kill cells of interest. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

All patents, applications and publications cited herein are incorporated by reference herein. The following examples are provided for illustrative purposes only and are not to be construed as limiting the invention in any way.

EXAMPLES

Example I

Cloning and Expression of rOnc and Onc Conjugates with EDN

A. Materials. Native ONCONASE® ("nOnc") (SEQ ID NO:1) Ardelt et al. (1991) *J. Biol. Chem.* 256, 245–251 and recombinant human EDN ("rEDN") (SEQ ID NO:9) Newton et al. (1994) *J Biol Chem.* 269, 26739–26745 were purified from *Rana pipiens* oocytes, NASCO, Fort Atkinson, Wis. and *Escherichia coli,* respectively, as described. Antibodies to the denatured proteins were prepared by Assay Research, Inc., College Park, Md. Reagents for performing PCR, and direct cloning of PCR products, were obtained from Perkin-Elmer Corp., Norwalk, Conn. and from Invitrogen, San Diego, Calif. respectively. Substrates for the ribonuclease assays were purchased from Sigma, St. Louis, Mo. and Boehringer Mannheim, Indianapolis, Ind. The materials and their sources used in the construction and expression of the recombinant proteins as well as the rabbit reticulocyte lysate are described by Newton et al., *Biochemistry* 35:545 (1996).

B. PCR Cloning of Onconase. Rana pipiens genomic DNA was isolated according to standard procedures using proteinase K Maniatis, T., Fritsch, E. F. & Sambrook, *J. Molecular Cloning, a laboratory manual* (Cold Spring Harbor Laboratory, Cold Spring Harbor, N.Y., 1982). A series of degenerate primers were designed to correspond to amino acids in various regions of the published nOnc sequence Ardelt et al. (1991) *J. Biol. Chem.* 256, 245–251. The PCR reaction was performed according to the manufacturer's instructions using 15 μg of genomic DNA in 100 μl. All reagents except the DNA were combined and incubated at 95° C. for 8 min to inactivate any residual proteinase K before the addition of the Taq DNA polymerase. PCR was performed for 40 cycles of denaturation at 94° C. for 1 min, annealing for 2 min at 55° C. and primer extension for 2 min at 72° C. Several pairs of primers yielded products of the expected size. The largest product (252 bp) was obtained using the forward primer encoding amino acid residues 15–23 (AG(GA)GATGT(GT)GATTG(TC)GATAA(CT)ATCATG) (SEQ ID NO:35) and the reverse primer encoding amino acid residues 90–98 (TGTGA(AG)AA(CT)CAGGC(AC)CC(TA)GT(GT)CA(CT)TTT) (SEQ ID NO:36). This fragment was subcloned into pCR™II by TA cloning and a clone carrying an insert of the appropriate size was directly sequenced and found to encode amino acid residues 16–98 of nOnc ("Rana 9") (SEQ ID NO:2). The corresponding nucleic acid sequence is set out in SEQ ID NO:37.

C. Plasmid Construction, Expression, Protein Purification and in Vitro Assays. The N- and C-termini of nOnc were reconstructed using the PCR technique of splicing by overlap extension Horten et al. (1990) *BioTechniques* 8, 528–532 with amino acid residues 1–15 of nOnc or amino acid residues 1–21 of EDN at the N-terminal and amino acid residues 99–104 of nOnc at the C-terminal. The assembled genes were inserted between the XbaI and BamHI sites of the bacterial expression vector, pET-11d, Novagen, Madison, Wis. All procedures were accomplished essentially as described in Newton et al. (1994) *J Biol Chem.* 269, 26739–26745. The plasmids were expressed in BL21(DE3) *E. coli* cells as recommended by the supplier, Novagen, Madison Wis. The fusion proteins were isolated from inclusion bodies, denatured, renatured and dialyzed as described Newton et al. (1994) *J Biol Chem.* 269, 26739–26745 before being applied to a CM-Sephadex C-50 column, Pharmacia Biotech Inc., Piscataway, N.J. The proteins were eluted with a NaCl gradient (0–0.5M) in 20 mM Tris-HCl, pH 7.5, containing 10% glycerol. Final purification to >95% was achieved by size exclusion chromatography on Sephadex G-100 equilibrated and eluted with 5% formic acid. The proteins were pooled, concentrated by amicon ultrafiltration using a YM3 membrane (or lyophilized), Amicon, Beverly, Mass. and dialyzed against 20 mM Tris-HCl, pH 7.5, containing 10% glycerol before being assayed.

Ribonuclease activity using high molecular weight RNA and tRNA was determined following published protocols, Newton et al. (1994) *J Neurosci* 14, 538–544 at 37° C. through the formation of perchloric acid soluble nucleotides following published protocols (Newton et al. (1996) *Biochem.* 35:545–553). With poly (A,C), UpG and poly U, ribonuclease activity was assayed spectrophotometrically according to DePrisco et al., and Libonati and Floridia DePrisco et al. (1984) *Biochimica et Biophysica Acta* 788, 356–363, Libonati, M. & Floridi, A. (1969) *European J. Biochem.* 8, 81–87. Briefly, activity was assayed by measuring the increase in absorbance at 260 nm. Incubation mixtures (1 ml of 10 mM imidazole, 0.1 M NaCl, pH 6.5 or pH 7) contained substrate and appropriate amounts of enzyme solution at 25° C. The in vitro translation assay, St. Clair et al. (1987) *Proc Natl Acad Sci* 84, 8330–8334, and the cell viability assays, Pearson et al. (1991) *J Natl Cancer Inst* 83, 1386–1391, using the (3-[4,5-Dimethylthiazol-2-yl-2,5-diphenyltetrazolium bromide; Thiazolyl blue] (MTT) Mossman, T. (1983) *J. Immunol. Methods* 65, 55–63 were performed as previously described.

D. Cloning and Expression of [Met-(-1)] rOnc and rOnc chimeras. Eight different oligonucleotide primers were designed to correspond to specific regions in the primary amino acid structure of nOnc, Ardelt et al. (1991) *J. Biol. Chem.* 256, 245–251 and amplification of *Rana pipiens* genomic DNA was carried out in a thermal cycler, as described above. A primer pair corresponding to amino acid residues 15 to 23 and 90 to 98 of nOnc, respectively, generated a 252 bp fragment. That PCR product, here denoted Rana clone 9, was cloned into pCR™II and sequence analysis confirmed that the PCR product encoded Onc (104 amino acids, total) from amino acid residue 16 to 98 (FIG. 1).

The entire recombinant Onc ("rOnc") gene (SEQ ID NO:38) was constructed by PCR extension and cloned into an expression vector using methodology previously described Newton et al. (1994) *J Biol Chem.* 269, 26739–26745. The amino and carboxyl termini of rOnc were completed by inserting the first 15 and last 6 amino acid residues of nOnc, respectively. The configuration of the semi-synthetic rOnc gene is depicted at the top of FIG. 2A. The primers were designed to overlap with the DNA sequence of the Rana clone 9 PCR product. The plasmid was expressed in BL21(DE3) *E. coli* and the recombinant protein was isolated from inclusion bodies as described in Newton et al. (1994) *J Biol Chem.* 269, 26739–26745 before being applied to a CM Sephadex C-50 column. Final purification to >95% was achieved by size exclusion chromatography. The rOnc obtained from the bacteria in this expression system contains an extra methionine at the amino terminal [Met-(-1)] (SEQ ID NO:39) in contrast to the authentic pyroglutamyl amino acid residue (<Glu-1) of the native protein (SEQ ID NO:1).

To humanize [Met-(-1)] rOnc while maintaining the alignment of the active site residues (FIG. 2B), the N-terminal of Rana clone 9 was also reconstituted with oligonucleotides that coded for the first 21 amino acid residues of a human eosinophil RNase, EDN (FIG. 2B, rEDN$_{(1-21)}$Onc). PCR cloning can result in sequence errors. Indeed, the DNA sequence of the gene encoding EDN$_{(1-21)}$Onc contained an A to G substitution resulting in a change from Asp to Gly at position 26 in the chimera (residue 20 in nOnc) and is designated as rEDN$_{(1-21)}$rOncG$_{26}$ in FIG. 2B. Another plasmid containing encoding rEDN$_{(1-21)}$rOnc was sequenced and found to have the correct DNA sequence. Since the mutation resulted in the substitution of a charged amino acid with a small neutral residue the mutant chimera was also expressed and characterized for activity. In addition, [Met-(-1)]rOnc was mutated at position 20 from Asp to Gly (rOncGly$_{20}$, FIGS. 2A and 2B).

E. Ribonuclease activity of Onc, EDN, [Met-(-1)]rOnc and hybrid rOnc proteins. Both nOnc (Lin, J. J., et al. (1994) *Biochem Biophys Res Commun* 204, 156–162) and EDN (Saxena et al. (1992) *J. Biol. Chem.* 267, 21982–21986) are potent inhibitors of in vitro translation in the rabbit reticulocyte lysate by mechanisms that depend upon their respective nucleolytic activities. As depicted in Table 1, the addition of nOnc or EDN to a rabbit reticulocyte lysate caused the inhibition of protein synthesis as measured by the incorporation of [$^{35}$S]methionine into acid precipitable protein. Whereas both nOnc and EDN inhibited protein synthesis with $IC_{50s}$ of 0.2 and 1.3 ng/ml, respectively, [Met-(-1)]rOnc, [Met-(-1)]rOncG20, and $rEDN_{(1-21)}rOncG26$ were considerably less potent ($IC_{50s}$ 98, 28 and 28 ng/ml, respectively). The least active RNase in this assay was $rEDN_{(1-21)}rOnc$ with an $IC_{50}$ of 1600 ng/ml. Placental ribonuclease inhibitor (PRI) binds tightly to EDN and inhibits its enzymatic activity, Sorrentino et al. (1992) *J. Biol. Chem* 267, 14859–14865, yet nOnc activity is very little affected by PRI, Wu, Y. N., et al. (1993) *Journal of Biological Chemistry* 268, 10686–10693 and Table 1, despite its homology to EDN and other members of the pancreatic RNase superfamily. In this regard, it is interesting that the activity of $rEDN_{(1-21)}rOnc$ is, like nOnc, barely affected by PRI while the hybrid RNase with the Gly mutation now behaves more like EDN in that its activity is significantly inhibited (21 fold) by PRI.

The ribonuclease activity of these proteins was also assessed in assays using high and low molecular weight substrates. As shown in Table 2, EDN and nOnc have different substrate specificities consistent with previously published results (Ardelt et al. (1991) *J. Biol. Chem.* 256, 245–251, Sorrentino et al. (1992) *J. Biol. Chem* 267, 14859–14865, Ardelt et al. (1994) *Protein Sci* 3, Suppl. 1, 137). Consistent with the results presented in Table 1, [Met-(-1)]rOnc (SEQ ID NO:39) and $rEDN_{(1-21)}rOnc$ were much less active with all of the substrates (non detectable or very little activity under the assay conditions employed). Surprisingly, the Gly containing hybrid protein, manifested significant ribonuclease activity especially under conditions optimal for EDN enzymatic activity. EDN is more active at a neutral pH (Sorrentino et al. (1992) *J. Biol. Chem* 267, 14859–14865) and as seen in Table 2 there is a marked increase in EDN degradation of tRNA at pH 7.5 compared to pH 6 (42.3 fold). Also, behaving like EDN, the Gly-containing hybrid increases in activity with a pH shift from 6 to 7.5 (21.7 fold) while nOnc loses activity at pH 7.5 consistent with its pH optimum that ranges from 6–6.5 (Ardelt et al. (1991) *J. Biol. Chem.* 256, 245–251, Ardelt et al. (1994) *Protein Sci* 3, Suppl. 1, 137). The enhanced EDN-like activity of the Gly-containing hybrid protein is also evidenced by its behavior with poly(A,C) which is an excellent substrate for EDN. As seen in Table 2, only $rEDN_{(1-21)}rOncG26$ expresses almost 50% of the enzymatic activity of EDN with this substrate whereas the activity of the other RNases are negligible. Similar results were observed with poly(U). In contrast, there was no detectable activity of rEDN or $rEDN_{(1-21)}rOncG26$ with UpG, an optimal Onconase substrate (Ardelt et al. (1994) *Protein Sci* 3, Suppl. 1, 137). In summary, both [Met-(-1)]rOnc and $rEDN_{(1-21)}rOnc$ are less enzymatically active than nOnc or rEDN. Although, $rEDN_{(1-21)}rOncG26$ expresses significant EDN-like enzymatic activity when assayed using defined substrates and conditions optimal for EDN, it is not as active as EDN in any assay. This could result from an impaired enzyme substrate interaction or from the use of suboptimal assay conditions for this hybrid enzyme.

TABLE 1

Activity of [Met-(-1)]rOnc or Hybrid Proteins in Rabbit Reticulocyte Lysate compared to rEDN or nOnc in the Presence or Absence of PRI

|  | $IC_{50}{}^a$ (ng/ml) | | |
| --- | --- | --- | --- |
|  | (−)PRI | (+)PRI | Fold Difference |
| nOnc | 0.2 | 0.24 | 1.2 |
| rEDN | 1.3 | >40 | >30.7 |
| [Met-(-1)]rOnc | 96 | 140 | 1.4 |
| [Met-(-1)]rOncG20 | 28 | 24 | 0.9 |
| $rEDN_{(1-21)}rOnc$ | 1600 | 3200 | 2 |
| $rEDN_{(1-21)}rOncG26$ | 28 | 600 | 21 |

$^a IC_{50}$ is the concentration of protein necessary to inhibit protein synthesis by 50% in the rabbit reticulocyte lysate. Data points result from the average of at least three assays.

TABLE 2

Activity of RNases on Different Substrates

| | | RNase Activity (units/mg protein)$^a$ | | | | |
| --- | --- | --- | --- | --- | --- | --- |
| Substrate | Assay pH | rEDN | nOnc | [Met-(-1)]rOnc | $rEND_{1-21r}Onc$ | $rEDN_{1-21r}OncG_{26}$ |
| Yeast RNA$^a$ | 6.0 | 6000 | 560 | 0.01 | 8 | 120 |
| tRNA$^{a,c}$ | 6.0 | 1100 | 390 | 12 | 4 | 340 |
| tRNA$^{a,c}$ | 7.5 | 46000 | 60 | 50 | 130 | 7400 |
| poly (A,C)$^b$ | 7.0 | 8000 | 0.04 | 5 | 4.5 | 3900 |
| UpG$^b$ | 6.5 | 0.05 | 0.18 | <0.01 | <0.01 | <0.01 |
| poly U$^b$ | 7.0 | 16.5 | 0.15 | 0.20 | 0.35 | 4.5 |

$^a$RNase activity was quantitated through the formation of perchloric acid soluble nucleotides. Units are defined as the changes in $A_{260}$ per minute calculated from the slopes of the linear part of the assays. Each value is the average of 2–3 assays in separate experiments.
$^b$Spectrophotometric assays were performed according to Deprisco et al. (1984) and Libonati and Floridi (1969) as described in Materials and Methods. Units are defined as the changes in $A_{260}$ per minute calculated from the slopes of the linear part of the assays. Each value is the average of two or more determinatinos.
$^c$[Met-(-1)]rOncG20 had no detectable activity.

F. Inhibition of protein synthesis in four human tumor cell lines by RNases. The cytotoxic effect of [Met-(-1)]rOnc and the two hybrid RNases were compared to rEDN and nOnc by determining cell viability using the MTT assay. As depicted in FIG. 3, nOnc decreased tumor cell viability in all four human tumor cell lines. At the concentrations shown, rEDN had no effect on the viability of any of the cell lines. In contrast to nOnc, [Met-(-1)]rOnc as well as [Met-(-1)] rOncG20 was consistently less cytotoxic in all four cell lines. Yet, rEDN$_{(1-21)}$rOncG26 was more cytotoxic than nOnc in ACHN, human renal carcinoma cells and equally cytotoxic in the MDA-MB-231 human breast carcinoma cell line. Although rEDN$_{(1-21)}$rOncG26 was less active than nOnc in the SF-539 and HS 578T human glioma and breast cancer cell lines, respectively, it was still more active than [Met-(-1)]rOnc or rEDN$_{(1-21)}$rOnc protein containing Asn at position 26.

G. Structural Analysis of the hybrid RNases. Modeling the hybrid RNase was based on the alignment of the structures for Onc (Mosimann S. C., Ardelt W., James M. N. G., (1994), Refined 1.7 A X-ray crystallographic structure of P-30 protein, an amphibian ribonuclease with anti-tumor activity (*J Mol Biol* 236, 1141–1153) and EDN (Mosimann S. C., Newton D. L., Youle R. J., James M., X-ray crystallographic structure of recombinant eosinophil-derived neurotoxin at 1.83A resolution *J Mol Biol*). This and subsequent alignments were carried out using ALIGN (Satow Y., Cohen G. H., Padlan E. A., Davies D. R., (1986), *J. Mol Biol* 190, 593–604).

H. Modeling the structures of the hybrid RNases. The coordinates for Onc and EDN were superimposed on the basis of C$^\alpha$ trace alignment. Residues in conserved zones, particularly in the active site, showed very little displacement when comparing both structures (global r.m.s.d. of 1.44 A for 90 C$^\alpha$ atom pairs). The hybrid protein was modeled by manual rebuilding and geometry regularization using TOM (Cambillau C., Horjales E., (1987), *J. Mol Graph* 5, 174–177). Subsequently, the models for rEDN$_{(1-21)}$rOnc and rEDN$_{(1-21)}$rOncG26 were assigned an overall B-factor of 15 A$^2$ for all non-hydrogen atoms and independently subject to 300 cycles of positional energy minimization with the program XPLOR (Brunger A. (1992) XPLOR: a system for X-ray crystallography and NMR., New Haven: Yale University Press). The minimization yielded virtually identical structures in both cases, the highest distance based on C$^\alpha$ trace alignment being 0.44 for the C$^\alpha$ of the mutated residue 26. The geometry quality of the final models were assessed with PROCHECK (Laskowski R. A., MacArthur M. W., Moss D. S., Thornton J. M., (1993), *J Appl Crystallogr* 26, 283–291).

The structural basis for the marked differences in activity between the Gly and Asp containing hybrid RNases are not obvious from modeling these proteins especially since residue 26 is distant from the active site. When the highly homologous structure of RNase A complexed with a pentanucleotide (Fontecilla-Camps J. C., deLorens R., leDu M. H., Cuchillo C. M., (1994), *J. Biol Chem* 269, 21526–21531) was superimposed on the structure of the hybrid protein model, the nucleotide was observed also to be distant from the region of the mutation. However, the arrangement of the polynucleotide chain in the different RNases does not necessarily have to coincide. In the structure of EDN, a second sulfate ion was found in addition to the one in the active site (Mosimann S. C., Newton D. L., Youle R. J., James M., X-ray crystallographic structure of recombinant eosinophil-derived neurotoxin at 1.83A resolution *J Mol Biol*). This second sulfate is likely replacing a phosphate from the nucleotide to be cleaved, but no phosphate ion is located in the equivalent position in the RNase A-pentanucleotide complex. Moreover, one of the phosphates in this complex is forming a salt bridge with Lys-66, a residue which has no counterpart in Onc since it is located in a loop with a different topology in both molecules. Thus, whether the difference in enzymatic activity between the Asp and Gly mutants in the chimera is related to a change in the binding affinity for the substrate remains an open question.

Although the structural basis for the difference in the activities of the two EDN-Onc hybrids is not clear, the EDN-like behavior of the rEDN$_{(1-21)}$rOncG26 hybrid can likely be attributed to the configuration of the N-terminal region since both the pyroglutamic acid in nOnc and Lys-1 in EDN are located in the area of the active site (Mosimann S. C., Ardelt W., James M. N. G., (1994), Refined 1.7 A X-ray crystallographic structure of P-30 protein, an amphibian ribonuclease with anti-tumor activity *J Mol Biol* 236, 1141–1153; Mosimann S. C., Newton D. L., Youle R. J., James M., X-ray crystallographic structure of recombinant eosinophil-derived neurotoxin at 1.83A resolution *J Mol Biol*). In addition, the introduction of a Gly mutation in [Met-(-1)]rOnc did not significantly affect enzymatic activity. The preference of U over C in the B1 subsite of RNase A has been related to the presence of a particular residue (Asp-83) (DelCardayre S. B., Raines R. T., (1995), A residue to residue hydrogen bond mediates the nucleotide specificity of ribonuclease A *J Mol Biol* 252, 328–336). The corresponding residue in nOnc is also an aspartic acid (Asp-67), while in EDN this position is occupied by a histidine (His-82). EDN is more active toward poly (A,C), suggesting that it "prefers" C in the B1 subsite, possibly because it contains a histidine residue as opposed to the aspartic acid in nOnc and RNase A. Taken together, this could explain the decreased activity of the Gly containing hybrid relative to rEDN since, according to this hypothesis, the presence of the Asp residue contributed by the rOnc sequence would favor the binding of U over C. With regard to the difference in PRI inhibition, the superposition between the hybrid proteins and RNase A demonstrates that Asp-26 in the EDN-Onc chimeras is in the equivalent position to Asn-27 in RNase A that has been reported to be in contact with PRI (Kobe B., Deisenhofer J., (1995), *Nature* 374, 183–186). In addition, Asp-24 in both chimeras is very close to this region. Thus, the accumulation of negative charges in this area could prevent binding by the inhibitor. If so, the substitution of Gly for Asp would decrease the negative charge and restore the binding capacity.

Example II rOnc-Antibody Fusion Proteins

Additional rOnc-antibody and ligand proteins have been produced and are highly active. E6FB[Met-(-1)]SerrOnc is an rOnc molecule having the amino acid sequence set out in SEQ ID NO:64 and includes the Fv sequence from antibody E6, an anti-transferrin receptor antibody. See sequences for E6 at amino acid positions 1–237 in SEQ ID NO:41. "FB" refers to a linker used to link the antibody and the rOnc portion of the molecule and is found at nucleic acid positions 712 through 750 in SEQ ID NO:40. E6FB[Met-(-1)]SerrOnc (SEQ ID NO:64) includes a Ser at amino acid position 252 instead of a Glu. Similar hybrid molecules have been made. The nucleic acid and amino acid sequences for Met-NLS (signal peptide)-Gln-rOncFBE6 are set out on SEQ ID NOS:42 and 43. Another E6/rOnc molecule is designated Met-Ser-rOncA87FBE6 and is found on SEQ ID NOS:44 and 45. "A87" refers to the fact that an Ala occurs at amino acid position 87.

Met-Ser-rOnc-Ang-FBE6 is set out on SEQ ID NOS:46 and 47.

E6FBMet-Ser-rOnc is set out on SEQ ID NOS:48 and 49.

Met-Glu-rOncFBE6 is set out on SEQ ID NOS:50 and 51.

Met-Ser-rOncFBE6 is set out on SEQ ID NOS:50 and 51, with the exception that Ser replaces Glu at amino acid position 2.

MOC31 and MOC162 refer to anti-colon cancer antibodies directed against the 17-1-A pancarcinoma antigen which were obtained from Dr. Hennie Hoogenboom. The Fv region of these antibodies was fused to rOnc. The nucleic acid and amino acid sequences for MetSerrOnc A87 FBMOC31 are set out on SEQ ID NOS:52 and 53. The nucleic acid and amino acid sequences for MOC31FBMetSerrOnc are set out on SEQ ID NOS:54 and 55. The nucleic acid and amino acid sequences for MetSerrOncFBMOC161 are set out on SEQ ID NOS:56 and 57.

The ligand, IL2 (interleukin 2) was recombinantly fused to rOnc as well. See SEQ ID NOS:58 and 59 for IL2FBMetSerrOnc. See SEQ ID NOS:60 and 61 for Met-SerrOncFBIL2.

Inhibition of protein synthesis in SF539 cells (which bear the transferrin receptor) was measured, as described above, for [Met-(-1)Ser]rOnc, E6FB[Met-(-1)Ser]rOnc; [Met-(-1)Ser]rOnc-AngFBE6 and [Met-(-1)Glu]rOncFBE6 constructs and compared with nOnc. The results are shown on Table 3. The three E6 constructs, in particular, had a very high level of activity—up to 45 fold difference over the two non-E6 molecules. See also FIG. 5. MetSerOncAng molecule was made corresponding to amino acids 1–107 of SEQ ID NO:47.

TABLE 3

Activity of modified rOnc and modified rOncFvs on protein synthesis

| RNase | $IC_{50}$ (nM) | Fold Difference |
| --- | --- | --- |
| nOnc | 10 | 1 |
| [Met-(−1)Ser]rOnc | 8 | NSD |
| E6FB[Met-(−1)Ser]rOnc | 0.22 | 45 |
| [Met-(−1)Ser]rOnc-AngFBE6 | 0.27 | 37 |
| [Met-(−1)Glu]rOncFBE6 | 0.50 | 20 |

The concentrations necessary to inhibit protein synthesis by 50% in SF539 human glioma cells. NSD, no significant difference.

What is claimed is:

1. A ribonuclease molecule comprising: (a) an amino terminal end beginning with a methionine which is followed by any amino acid other than glutamic acid; (b) when aligned for maximum correspondence with SEQ ID NO:13, a cysteine at amino acid positions 26, 40, 58, 84, 95 and 110; a lysine at position 41 and a histidine at position 119, and (c) an nOnc-derived amino acid sequence; wherein said ribonuclease molecule has measurable ribonuclease activity.

2. The ribonuclease of claim 1 which has an amino terminal end selected from the group consisting of: Met-Lys; Met-Tyr; Met-Ser; Met-Ala; Met-Arg; and Met-Asn.

3. The ribonuclease of claim 1, which has an amino terminal end selected from the group consisting of:

Met-Ala;

Met-Ala-Ala;

Met-Ala-Ala-Ser;

Met-Arg;

Met-(J);

Met-Lys-(J);

Met-Arg-(J);

Met-Lys;

Met-Lys-Pro;

Met-Lys-(J)-Pro (SEQ ID NO:14);

Met-Lys-Pro-(J) (SEQ ID NO:15);

Met-Asn;

Met-Gln;

Met-Asn-(J);

Met-Gln-(J);

Met-Asn-(J)-Pro (SEQ ID NO:16);

Met-(J)-Lys;

Met-(J)-Lys-Pro (SEQ ID NO:17); and

Met-(J)-Pro-Lys (SEQ ID NO:18);

where (J) is Ser, Tyr or Thr.

4. The ribonuclease of claim 1, which has an amino terminal end of Met-Ala.

5. The ribonuclease of claim 1, which has an amino terminal end of Met-Arg.

6. The ribonuclease of claim 1, which has an amino terminal end of Met-Lys.

7. The ribonuclease of claim 1, which has an amino terminal end of Met-Asn.

8. The ribonuclease of claim 1, which has an amino terminal end of Met-Gln.

9. The ribonuclease of claim 1, which has an amino terminal end selected from the group consisting of Met-Ser; Met-Tyr or Met-Thr.

10. The ribonuclease of claim 3, wherein aspartic acid of amino acid position 2 of the amino acid sequence of (c) or position 4 with reference to the sequence of bovine RNase is deleted or replaced by Ala or Asn.

11. The ribonuclease of claim 1 wherein the amino acid sequence comprises a sequence having the formula:

Met(-1) eosinophil derived neurotoxin$_{(1-m)}$Onc$_{(n-104)}$ wherein Met(-1) refers to an amino terminal residue of Met; wherein eosinophil derived neurotoxin$_{(1-m)}$ refers to a contiguous sequence of amino acids of a length beginning at amino acid position 1 of eosinophil derived neurotoxin (SEQ ID NO:9) and continuing to and including amino acid position "m" of eosinophil derived neurotoxin; wherein Onc$_{(n-104)}$ refers to a sequence of contiguous amino acids beginning at no acid position "n" and continuing to and including amino acid position 104 as set out in SEQ ID NO:1; and wherein "m" is the amino acid position of eosinophil derived neurotoxin selected from the group consisting of 5, 13, 14, 15, 16, 17, 18, 19, 20, 21 and 22; such that:

when m is 21, n is 16 or 17;

when m is 22, n is 17;

when m is 20, n is 16;

when m is 19, n is 15;

when m is 18, n is 14;

when m is 17, n is 12 or 13;

when m is 16, n is 11, 12, 13 or 14;

when m is 15, n is 10;

when m is 14, n is 9;

when m is 13, n is 8; and when m is 5, n is 1.

12. The ribonuclease of claim 1, comprising an amino acid sequence substantially identical to that of SEQ ID NO:28.

13. The ribonuclease of claim 1, comprising an amino acid sequence substantially identical to that of SEQ ID NO:22.

14. The ribonuclease of claim 1, comprising an amino acid sequence substantially identical to that of SEQ ID NO:24.

15. The ribonuclease of claim 1, comprising an amino acid sequence substantially identical to that of SEQ ID NO:26.

16. The ribonuclease of claim 1, comprising an amino acid sequence substantially identical to that of SEQ ID NO:30.

17. The ribonuclease of claim 1, comprising an amino acid sequence substantially identical to that of SEQ ID NO:32.

18. The ribonuclease of claim 1, which includes an amino acid sequence substantially identical to that of SEQ ID NO:2.

19. The ribonuclease of claim 1, comprising a carboxyl terminal end derived from angiogenin corresponding to the amino acid sequence of positions 101 to 107 of SEQ ID NO:20.

20. The ribonuclease of claim 19, comprising an amino acid sequence substantially identical to that of SEQ ID NO:20.

21. An isolated amino acid sequence substantially identical to that set out in SEQ ID NO:2.

22. A fusion protein comprising the ribonuclease of claim 1 joined to a ligand binding moiety or label.

23. The fusion protein of claim 22, further comprising an antibody.

24. An isolated nucleic acid sequence encoding the amino acid sequence of claim 1.

25. A pharmaceutical composition comprising a cytotoxic amount of a ribonuclease of claim 1 and a pharmaceutically acceptable carrier.

26. The pharmaceutical composition of claim 25 wherein the ribonuclease is joined to a ligand binding moiety.

27. A method of selectively killing cells comprising contacting cells to be killed with a ribonuclease of claim 1 joined to a ligand binding moiety.

28. The ribonuclease molecule of claim 1 which further has a nuclear localization signal.

29. The ribonuclease molecule of claim 1 which further has an endoplasmic retention sequence.

30. A vector comprising a nucleic acid encoding a ribonuclease of claim 1.

31. A host cell comprising a nucleic acid encoding a ribonuclease of claim 1.

* * * * *

UNITED STATES PATENT AND TRADEMARK OFFICE
CERTIFICATE OF CORRECTION

PATENT NO. : 6,045,793
DATED : Apr. 4, 2000
INVENTOR(S) : Susanna M. Rybak, Dianne L. Newton, Lluis Boque, and Alexander It is certified that error appears in the above-identified patent and that said Letters Patent is hereby corrected as shown below:

On the cover page after the Inventors please insert --Assignee: THE UNITED STATES OF AMERICA as represented by the Secretary of the Department of Health and Human Services, Washington, D.C.--

At column 116, line 3, after "at" delete "no" and substitute therefor --amino--.

At column 116, line 19, after "is" delete "14,n is9;" and insert therefor --14, n is 9;--.

Signed and Sealed this

Twenty-ninth Day of August, 2000

Attest:

Attesting Officer

Q. TODD DICKINSON

Director of Patents and Trademarks

SEQUENCE LISTING (1) GENERAL INFORMATION:

(iii) NUMBER OF SEQUENCES: 64

(2) INFORMATION FOR SEQ ID NO:1:

(i) SEQUENCE CHARACTERISTICS:
      (A) LENGTH: 104 amino acids
      (B) TYPE: amino acid
      (C) STRANDEDNESS:
      (D) TOPOLOGY: linear (ii) MOLECULE TYPE: protein (ix) FEATURE:
      (A) NAME/KEY: Protein
      (B) LOCATION: 1..104
      (D) OTHER INFORMATION: /label= nOnc
         /note= "native ONCONASE (Registered Trademark) from Rana pipiens"

(ix) FEATURE:
      (A) NAME/KEY: Modified-site
      (B) LOCATION: 1
      (D) OTHER INFORMATION: /note= "Xaa = pyroglutamic acid"

(xi) SEQUENCE DESCRIPTION: SEQ ID NO:1:

```
Xaa Asp Trp Leu Thr Phe Gln Lys Lys His Ile Thr Asn Thr Arg Asp
 1               5                  10                  15

Val Asp Cys Asp Asn Ile Met Ser Thr Asn Leu Phe His Cys Lys Asp
                20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
        50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
```

```
                        85                  90                  95
His Phe Val Gly Val Gly Ser Cys
            100
```

(2) INFORMATION FOR SEQ ID NO:2:

(i) SEQUENCE CHARACTERISTICS:
        (A) LENGTH: 83 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Peptide
        (B) LOCATION: 1..83
        (D) OTHER INFORMATION: /note= "Rana clone 9 peptide from Rana
            pipiens genomic DNA"

(xi) SEQUENCE DESCRIPTION: SEQ ID NO:2:

```
Asp Val Asp Cys Asp Asn Ile Met Ser Thr Asn Leu Phe His Cys Lys
1               5                   10                  15

Asp Lys Asn Thr Phe Ile Tyr Ser Arg Pro Glu Pro Val Lys Ala Ile
            20                  25                  30

Cys Lys Gly Ile Ile Ala Ser Lys Asn Val Leu Thr Thr Ser Glu Phe
        35                  40                  45

Tyr Leu Ser Asp Cys Asn Val Thr Ser Arg Pro Cys Lys Tyr Lys Leu
    50                  55                  60

Lys Lys Ser Thr Asn Lys Phe Cys Val Thr Cys Glu Asn Gln Ala Pro
65                  70                  75                  80

Val His Phe
```

(2) INFORMATION FOR SEQ ID NO:3:

(i) SEQUENCE CHARACTERISTICS:
        (A) LENGTH: 28 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide
        (B) LOCATION: 1..28
        (D) OTHER INFORMATION: /note= "N-terminal sequence of nOnc
            with Glu in place of pyroglutamic acid in position 1"

(xi) SEQUENCE DESCRIPTION: SEQ ID NO:3:

```
Glu Asp Trp Leu Thr Phe Gln Lys Lys His Ile Thr Asn Thr Arg Asp
1               5                   10                  15

Val Asp Cys Asp Asn Ile Met Ser Thr Asn Leu Phe
            20                  25
```

(2) INFORMATION FOR SEQ ID NO:4:

(i) SEQUENCE CHARACTERISTICS:
        (A) LENGTH: 34 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Peptide (B) LOCATION: 1..34
        (D) OTHER INFORMATION: /note= "N-terminal sequence of
            recombinant eosinophil-derived
            neurotoxin (rEDN)"

(xi) SEQUENCE DESCRIPTION: SEQ ID NO:4:

Lys Pro Pro Gln Phe Thr Trp Ala Gln Trp Phe Glu Thr Gln His (C) STRANDEDNESS:
        (D) TOPOLOGY: linear (ii) MOLECULE TYPE: peptide (ix) FEATURE:
        (A) NAME/KEY: Peptide
        (B) LOCATION: 1..34
        (D) OTHER INFORMATION: /note= "N-terminal sequence of
            rEDN1-21rOncG26, containing a Gly to Asp
            substitution at position 26 of
            rEDN1-21rOnc, and without the extra
            N-terminal Met from the E. coli
            bacterial expression system"

(xi) SEQUENCE DESCRIPTION: SEQ ID NO:7:

Lys Pro Pro Gln Phe Thr Trp Ala Gln Trp Phe Glu Thr Gln His Ile
1               5                   10                  15

Asn Met Thr Ser Gln Asp Val Asp Cys Gly Asn Ile Met Ser Thr Asn
            20                  25                  30

Leu Phe (2) INFORMATION FOR SEQ ID NO:8:

(i) SEQUENCE CHARACTERISTICS:
        (A) LENGTH: 111 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..111
        (D) OTHER INFORMATION: /note= "Frog Lectin from Rana
            catesbeiana"

(xi) SEQUENCE DESCRIPTION: SEQ ID NO:8:

Glu Asn Trp Ala Thr Phe Gln Gln Lys His Ile Ile Asn Thr Pro Ile
1               5                   10                  15

Ile Asn Cys Asn Thr Ile Met Asp Asn Asn Ile Tyr Ile Val Gly Gly
            20                  25                  30

Gln Cys Lys Arg Val Asn Thr Phe Ile Ile Ser Ser Ala Thr Thr Val
        35                  40                  45

Lys Ala Ile Cys Thr Gly Val Ile Asn Met Asn Val Leu Ser Thr Thr
    50                  55                  60

Arg Phe Gln Leu Asn Thr Cys Thr Arg Thr Ser Ile Thr Pro Arg Pro
65                  70                  75                  80

Cys Pro Tyr Ser Ser Arg Thr Glu Thr Asn Tyr Ile Cys Val Lys Cys
                85                  90                  95

Glu Asn Gln Tyr Pro Val His Phe Ala Gly Ile Gly Arg Cys Pro
            100                 105                 110

(2) INFORMATION FOR SEQ ID NO:9:

(i) SEQUENCE CHARACTERISTICS:
        (A) LENGTH: 134 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..134

(D) OTHER INFORMATION: /note= "Human eosinophil-derived
    neurotoxin (EDN)"

(xi) SEQUENCE DESCRIPTION: SEQ ID NO:9:

Lys Pro Pro Gln Phe Thr Trp Ala Gln Trp Phe Glu Thr Gln His Ile
1               5                   10                  15

Asn Met Thr Ser Gln Gln Cys Thr Asn Ala Met Gln Val Ile Asn Asn
            20                  25                  30

Tyr Gln Arg Arg Cys Lys Asn Gln Asn Thr Phe Leu Leu Thr Thr Phe
            35                  40                  45

Ala Asn Val Val Asn Val Cys Gly Asn Pro Asn Met Thr Cys Pro Ser
    50                  55                  60

Asn Lys Thr Arg Lys Asn Cys His His Ser Gly Ser Gln Val Pro Leu
65                  70                  75                  80

Ile His Cys Asn Leu Thr Thr Pro Ser Pro Gln Asn Ile Ser Asn Cys
                85                  90                  95

Arg Tyr Ala Gln Thr Pro Ala Asn Met Phe Tyr Ile Val Ala Cys Asp
                100                 105                 110

Asn Arg Asp Gln Arg Arg Asp Pro Pro Gln Tyr Pro Val Val Pro Val
            115                 120                 125

His Leu Asp Arg Ile Ile
        130

(2) INFORMATION FOR SEQ ID NO:10:

(i) SEQUENCE CHARACTERISTICS:
        (A) LENGTH: 133 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..133
        (D) OTHER INFORMATION: /note= "Human eosinophil cationic
            protein (ECP)"

(xi) SEQUENCE DESCRIPTION: SEQ ID NO:10:

Arg Pro Pro Gln Phe Thr Arg Ala Gln Trp Phe Ala Ile Gln His Ile
1               5                   10                  15

Ser Leu Asn Pro Pro Arg Cys Thr Ile Ala Met Arg Ala Ile Asn Asn
            20                  25                  30

Tyr Arg Trp Arg Cys Lys Asn Gln Asn Thr Phe Leu Arg Thr Thr Phe
            35                  40                  45

Ala Asn Val Val Asn Val Cys Gly Asn Gln Ser Ile Arg Cys Pro His
    50                  55                  60

Asn Arg Thr Leu Asn Asn Cys His Arg Ser Arg Phe Arg Val Pro Leu
65                  70                  75                  80

Leu His Cys Asp Leu Ile Asn Pro Gly Ala Gln Asn Ile Ser Asn Cys
                85                  90                  95

Arg Tyr Ala Asp Arg Pro Gly Arg Arg Phe Tyr Val Val Ala Cys Asp
                100                 105                 110

Asn Arg Asp Pro Arg Asp Ser Pro Arg Tyr Pro Val Val Pro Val His
            115                 120                 125

Leu Asp Thr Thr Ile
        130

(2) INFORMATION FOR SEQ ID NO:11:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..125
        (D) OTHER INFORMATION: /note= "Bovine angiogenin (Ang)"

(xi) SEQUENCE DESCRIPTION: SEQ ID NO:11:

```
Ala Gln Asp Asp Tyr Arg Tyr Ile His Phe Leu Thr Gln His Tyr Asp
1               5                   10                  15

Ala Lys Pro Lys Gly Arg Asn Asp Glu Tyr Cys Phe His Met Met Lys
            20                  25                  30

Asn Arg Arg Leu Thr Arg Pro Cys Lys Asp Arg Asn Thr Phe Ile His
        35                  40                  45

Gly Asn Lys Asn Asp Ile Lys Ala Ile Cys Glu Asp Arg Asn Gly Gln
    50                  55                  60

Pro Tyr Arg Gly Asp Leu Arg Ile Ser Lys Ser Glu Phe Gln Ile Thr
65                  70                  75                  80

Ile Cys Lys His Lys Gly Gly Ser Ser Arg Pro Pro Cys Arg Tyr Gly
                85                  90                  95

Ala Thr Glu Asp Ser Arg Val Ile Val Val Gly Cys Glu Asn Gly Leu
            100                 105                 110

Pro Val His Phe Asp Glu Ser Phe Ile Thr Pro Arg His
        115                 120                 125
```

(2) INFORMATION FOR SEQ ID NO:12:

(i) SEQUENCE CHARACTERISTICS:
        (A) LENGTH: 124 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..124
        (D) OTHER INFORMATION: /note= "Bovine seminal RNase"

(xi) SEQUENCE DESCRIPTION: SEQ ID NO:12:

```
Lys Glu Ser Ala Ala Ala Lys Phe Glu Arg Gln His Met Asp Ser Gly
1               5                   10                  15

Asn Ser Pro Ser Ser Ser Asn Tyr Cys Asn Leu Met Met Cys Cys
            20                  25                  30

Arg Lys Met Thr Gln Gly Lys Cys Lys Pro Val Asn Thr Phe Val His
        35                  40                  45

Glu Ser Leu Ala Asp Val Lys Ala Val Cys Ser Gln Lys Lys Val Thr
    50                  55                  60

Cys Lys Asn Gly Gln Thr Asn Cys Tyr Gln Ser Lys Ser Thr Met Arg
65                  70                  75                  80

Ile Thr Asp Cys Arg Glu Thr Gly Ser Ser Lys Tyr Pro Asn Cys Ala
                85                  90                  95

Tyr Lys Thr Thr Gln Val Glu Lys His Ile Ile Val Ala Cys Gly Gly
            100                 105                 110
```

```
Lys Pro Ser Val Pro Val His Phe Asp Ala Ser Val
        115                 120
```

(2) INFORMATION FOR SEQ ID NO:13:

(i) SEQUENCE CHARACTERISTICS:
        (A) LENGTH: 124 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..124
        (D) OTHER INFORMATION: /note= "Bovine pancreatic RNase A"

(xi) SEQUENCE DESCRIPTION: SEQ ID NO:13:

```
Lys Glu Thr Ala Ala Ala Lys Phe Glu Arg Gln His Met Asp Ser Ser
1               5                   10                  15
Thr Ser Ala Ala Ser Ser Ser Asn Tyr Cys Asn Gln Met Met Lys Ser
            20                  25                  30
Arg Asn Leu Thr Lys Asp Arg Cys Lys Pro Val Asn Thr Phe Val His
        35                  40                  45
Glu Ser Leu Ala Asp Val Gln Ala Val Cys Ser Gln Lys Asn Val Ala
    50                  55                  60
Cys Lys Asn Gly Gln Thr Asn Cys Tyr Gln Ser Tyr Ser Thr Met Ser
65                  70                  75                  80
Ile Thr Asp Cys Arg Glu Thr Gly Ser Ser Lys Tyr Pro Asn Cys Ala
                85                  90                  95
Tyr Lys Thr Thr Gln Ala Asn Lys His Ile Ile Val Ala Cys Glu Gly
            100                 105                 110
Asn Pro Val Val Pro Val His Phe Asp Ala Ser Val
        115                 120
```

(2) INFORMATION FOR SEQ ID NO:14:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /note= "Xaa = Ser, Tyr or Thr"

(xi) SEQUENCE DESCRIPTION: SEQ ID NO:14:

```
Met Lys Xaa Pro
1
```

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:

(A) NAME/KEY: Modified-site
            (B) LOCATION: 4
            (D) OTHER INFORMATION: /note= "Xaa = Ser, Tyr or Thr"

(xi) SEQUENCE DESCRIPTION: SEQ ID NO:15:

Met Lys Pro Xaa
1

(2) INFORMATION FOR SEQ ID NO:16:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 3
            (D) OTHER INFORMATION: /note= "Xaa = Ser, Tyr or Thr"

(xi) SEQUENCE DESCRIPTION: SEQ ID NO:16:

Met Asn Xaa Pro
1

(2) INFORMATION FOR SEQ ID NO:17:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /note= "Xaa = Ser, Tyr or Thr"

(xi) SEQUENCE DESCRIPTION: SEQ ID NO:17:

Met Xaa Lys Pro
1

(2) INFORMATION FOR SEQ ID NO:18:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (ix) FEATURE:
            (A) NAME/KEY: Modified-site
            (B) LOCATION: 2
            (D) OTHER INFORMATION: /note= "Xaa = Ser, Tyr or Thr"

(xi) SEQUENCE DESCRIPTION: SEQ ID NO:18:

Met Xaa Pro Lys
1

(2) INFORMATION FOR SEQ ID NO:19:

(i) SEQUENCE CHARACTERISTICS:
            (A) LENGTH: 321 base pairs
            (B) TYPE: nucleic acid
            (C) STRANDEDNESS: single (D) TOPOLOGY: linear (ii) MOLECULE TYPE: DNA (ix) FEATURE:
    (A) NAME/KEY: CDS
    (B) LOCATION: 1..321
    (D) OTHER INFORMATION: /note= "MetSerOnc99Ang117"

(xi) SEQUENCE DESCRIPTION: SEQ ID NO:19:

```
ATC TCA GAT TGG CTT ACA TTT CAG AAA AAA CAC ATC ACA AAC ACA AGG        48
Ile Ser Asp Trp Leu Thr Phe Gln Lys Lys His Ile Thr Asn Thr Arg
 1               5                  10                  15

GAT GTT GAT TGT GAT AAT ATC ATG TCA ACA AAC TTG TTC CAC TGC AAG        96
Asp Val Asp Cys Asp Asn Ile Met Ser Thr Asn Leu Phe His Cys Lys
                20                  25                  30

GAC AAG AAC ACT TTT ATC TAT TCA CGT CCT GAG CCA GTG AAG GCC ATC       144
Asp Lys Asn Thr Phe Ile Tyr Ser Arg Pro Glu Pro Val Lys Ala Ile
        35                  40                  45

TGT AAA GGA ATT ATA GCC TCC AAA AAT GTG TTA ACT ACC TCT GAG TTT       192
Cys Lys Gly Ile Ile Ala Ser Lys Asn Val Leu Thr Thr Ser Glu Phe
 50                  55                  60

TAT CTC TCT GAT TGC AAT GTA ACA AGC AGG CCT TGC AAG TAT AAA TTA       240
Tyr Leu Ser Asp Cys Asn Val Thr Ser Arg Pro Cys Lys Tyr Lys Leu
 65                  70                  75                  80

AAG AAA TCA ACT AAT AAA TTT TGT GTA ACT TGT GAA AAT CAG GCA CCA       288
Lys Lys Ser Thr Asn Lys Phe Cys Val Thr Cys Glu Asn Gln Ala Pro
                85                  90                  95

GTT CAT TTT GTT CAG TCA ATT TTC CGT CGT CCG                           321
Val His Phe Val Gln Ser Ile Phe Arg Arg Pro
            100                 105
```

(2) INFORMATION FOR SEQ ID NO:20:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:20:

```
Ile Ser Asp Trp Leu Thr Phe Gln Lys Lys His Ile Thr Asn Thr Arg
 1               5                  10                  15

Asp Val Asp Cys Asp Asn Ile Met Ser Thr Asn Leu Phe His Cys Lys
                20                  25                  30

Asp Lys Asn Thr Phe Ile Tyr Ser Arg Pro Glu Pro Val Lys Ala Ile
        35                  40                  45

Cys Lys Gly Ile Ile Ala Ser Lys Asn Val Leu Thr Thr Ser Glu Phe
 50                  55                  60

Tyr Leu Ser Asp Cys Asn Val Thr Ser Arg Pro Cys Lys Tyr Lys Leu
 65                  70                  75                  80

Lys Lys Ser Thr Asn Lys Phe Cys Val Thr Cys Glu Asn Gln Ala Pro
                85                  90                  95

Val His Phe Val Gln Ser Ile Phe Arg Arg Pro
            100                 105
```

(2) INFORMATION FOR SEQ ID NO:21:

(i) SEQUENCE CHARACTERISTICS:
        (A) LENGTH: 333 base pairs
        (B) TYPE: nucleic acid
        (C) STRANDEDNESS: single -continued

```
            (D) TOPOLOGY: linear (ii) MOLECULE TYPE: DNA (ix) FEATURE:
            (A) NAME/KEY: CDS
            (B) LOCATION: 1..333
            (D) OTHER INFORMATION: /note= "EDNGlyOnc"

(xi) SEQUENCE DESCRIPTION: SEQ ID NO:21:

ATG AAA CCG CCG CAG TTC ACT TGG GCT CAG TGG TTC GAA ACT CAG CAT        48
Met Lys Pro Pro Gln Phe Thr Trp Ala Gln Trp Phe Glu Thr Gln His
 1               5                  10                  15

ATC AAC ATG ACT TCT CAG GAT GTT GAT TGT GGT AAT ATC ATG TCA ACA        96
Ile Asn Met Thr Ser Gln Asp Val Asp Cys Gly Asn Ile Met Ser Thr
                 20                  25                  30

AAC TTG TTC CAC TGC AAG GAC AAG AAC ACT TTT ATC TAT TCA CGT CCT       144
Asn Leu Phe His Cys Lys Asp Lys Asn Thr Phe Ile Tyr Ser Arg Pro
         35                  40                  45

GAG CCA GTG AAG GCC ATC TGT AAA GGA ATT ATA GCC TCC AAA AAT GTG       192
Glu Pro Val Lys Ala Ile Cys Lys Gly Ile Ile Ala Ser Lys Asn Val
 50                  55                  60

TTA ACT ACC TCT GAG TTT TAT CTC TCT GAT TGC AAT GTA ACA AGC AGG       240
Leu Thr Thr Ser Glu Phe Tyr Leu Ser Asp Cys Asn Val Thr Ser Arg
 65                  70                  75                  80

CCT TGC AAG TAT AAA TTA AAG AAA TCA ACT AAT AAA TTT TGT GTA ACT       288
Pro Cys Lys Tyr Lys Leu Lys Lys Ser Thr Asn Lys Phe Cys Val Thr
                 85                  90                  95

TGT GAA AAT CAG GCA CCA GTT CAT TTT GTT GGA GTT GGA TCT TGT           333
Cys Glu Asn Gln Ala Pro Val His Phe Val Gly Val Gly Ser Cys
                100                 105                 110

(2) INFORMATION FOR SEQ ID NO:22:

(i) SEQUENCE CHARACTERISTICS:
            (A) LENGTH: 111 amino acids
            (B) TYPE: amino acid
            (D) TOPOLOGY: linear (ii) MOLECULE TYPE: protein (xi) SEQUENCE DESCRIPTION: SEQ ID NO:22:

Met Lys Pro Pro Gln Phe Thr Trp Ala Gln Trp Phe Glu Thr Gln His
 1               5                  10                  15

Ile Asn Met Thr Ser Gln Asp Val Asp Cys Gly Asn Ile Met Ser Thr
                 20                  25                  30

Asn Leu Phe His Cys Lys Asp Lys Asn Thr Phe Ile Tyr Ser Arg Pro
         35                  40                  45

Glu Pro Val Lys Ala Ile Cys Lys Gly Ile Ile Ala Ser Lys Asn Val
 50                  55                  60

Leu Thr Thr Ser Glu Phe Tyr Leu Ser Asp Cys Asn Val Thr Ser Arg
 65                  70                  75                  80

Pro Cys Lys Tyr Lys Leu Lys Lys Ser Thr Asn Lys Phe Cys Val Thr
                 85                  90                  95

Cys Glu Asn Gln Ala Pro Val His Phe Val Gly Val Gly Ser Cys
                100                 105                 110

(2) INFORMATION FOR SEQ ID NO:23:

(i) SEQUENCE CHARACTERISTICS:
            (A) LENGTH: 315 base pairs
            (B) TYPE: nucleic acid
            (C) STRANDEDNESS: single
```

-continued

```
        (D) TOPOLOGY: linear (ii) MOLECULE TYPE: DNA (ix) FEATURE:
          (A) NAME/KEY: CDS
          (B) LOCATION: 1..315
          (D) OTHER INFORMATION: /note= "MetTyrrOnc"

(xi) SEQUENCE DESCRIPTION: SEQ ID NO:23:

ATG TAT GAT TGG CTT ACA TTT CAG AAA AAA CAC ATC ACA AAC ACA AGG        48
Met Tyr Asp Trp Leu Thr Phe Gln Lys Lys His Ile Thr Asn Thr Arg
 1               5                  10                  15

GAT GTT GAT TGT GAT AAT ATC ATG TCA ACA AAC TTG TTC CAC TGC AAG        96
Asp Val Asp Cys Asp Asn Ile Met Ser Thr Asn Leu Phe His Cys Lys
             20                  25                  30

GAC AAG AAC ACT TTT ACT TAT TCA CGT CCT GAG CCA GTG AAG GCC ATC       144
Asp Lys Asn Thr Phe Thr Tyr Ser Arg Pro Glu Pro Val Lys Ala Ile
         35                  40                  45

TGT AAA GGA ATT ATA GCC TCC AAA AAT GTG TTA ACT ACC TCT GAG TTT       192
Cys Lys Gly Ile Ile Ala Ser Lys Asn Val Leu Thr Thr Ser Glu Phe
     50                  55                  60

TAT CTC TCT GAT TGC AAT GTA ACA AGC AGG CCT TGC AAG TAT AAA TTA       240
Tyr Leu Ser Asp Cys Asn Val Thr Ser Arg Pro Cys Lys Tyr Lys Leu
 65                  70                  75                  80

AAG AAA TCA ACT AAT AAA TTT TGT GTA ACT TGT GAA AAT CAG GCA CCA       288
Lys Lys Ser Thr Asn Lys Phe Cys Val Thr Cys Glu Asn Gln Ala Pro
                 85                  90                  95

GTT CAT TTT GTT GGA GTT GGA TCT TGT                                    315
Val His Phe Val Gly Val Gly Ser Cys
            100                 105

(2) INFORMATION FOR SEQ ID NO:24:

(i) SEQUENCE CHARACTERISTICS:
          (A) LENGTH: 105 amino acids
          (B) TYPE: amino acid
          (D) TOPOLOGY: linear (ii) MOLECULE TYPE: protein (xi) SEQUENCE DESCRIPTION: SEQ ID NO:24:

Met Tyr Asp Trp Leu Thr Phe Gln Lys Lys His Ile Thr Asn Thr Arg
 1               5                  10                  15

Asp Val Asp Cys Asp Asn Ile Met Ser Thr Asn Leu Phe His Cys Lys
             20                  25                  30

Asp Lys Asn Thr Phe Thr Tyr Ser Arg Pro Glu Pro Val Lys Ala Ile
         35                  40                  45

Cys Lys Gly Ile Ile Ala Ser Lys Asn Val Leu Thr Thr Ser Glu Phe
     50                  55                  60

Tyr Leu Ser Asp Cys Asn Val Thr Ser Arg Pro Cys Lys Tyr Lys Leu
 65                  70                  75                  80

Lys Lys Ser Thr Asn Lys Phe Cys Val Thr Cys Glu Asn Gln Ala Pro
                 85                  90                  95

Val His Phe Val Gly Val Gly Ser Cys
            100                 105

(2) INFORMATION FOR SEQ ID NO:25:

(i) SEQUENCE CHARACTERISTICS:
          (A) LENGTH: 315 base pairs
          (B) TYPE: nucleic acid
          (C) STRANDEDNESS: single
```

(D) TOPOLOGY: linear (ii) MOLECULE TYPE: DNA (ix) FEATURE:
        (A) NAME/KEY: CDS
        (B) LOCATION: 1..315
        (D) OTHER INFORMATION: /note= "MetSerrOnc"

(xi) SEQUENCE DESCRIPTION: SEQ ID NO:25:

```
ATG TCA GAT TGG CTT ACA TTT CAG AAA AAA CAC ATC ACA AAC ACA AGG        48
Met Ser Asp Trp Leu Thr Phe Gln Lys Lys His Ile Thr Asn Thr Arg
 1               5                  10                  15

GAT GTT GAT TGT GAT AAT ATC ATG TCA ACA AAC TTG TTC CAC TGC AAG        96
Asp Val Asp Cys Asp Asn Ile Met Ser Thr Asn Leu Phe His Cys Lys
                20                  25                  30

GAC AAG AAC ACT TTT ACT TAT TCA CGT CCT GAG CCA GTG AAG GCC ATC       144
Asp Lys Asn Thr Phe Thr Tyr Ser Arg Pro Glu Pro Val Lys Ala Ile
         35                  40                  45

TGT AAA GGA ATT ATA GCC TCC AAA AAT GTG TTA ACT ACC TCT GAG TTT       192
Cys Lys Gly Ile Ile Ala Ser Lys Asn Val Leu Thr Thr Ser Glu Phe
 50                  55                  60

TAT CTC TCT GAT TGC AAT GTA ACA AGC AGG CCT TGC AAG TAT AAA TTA       240
Tyr Leu Ser Asp Cys Asn Val Thr Ser Arg Pro Cys Lys Tyr Lys Leu
 65                  70                  75                  80

AAG AAA TCA ACT AAT AAA TTT TGT GTA ACT TGT GAA AAT CAG GCA CCA       288
Lys Lys Ser Thr Asn Lys Phe Cys Val Thr Cys Glu Asn Gln Ala Pro
                 85                  90                  95

GTT CAT TTT GTT GGA GTT GGA TCT TGT                                   315
Val His Phe Val Gly Val Gly Ser Cys
                100                 105
```

(2) INFORMATION FOR SEQ ID NO:26:

(i) SEQUENCE CHARACTERISTICS:
        (A) LENGTH: 105 amino acids
        (B) TYPE: amino acid
        (D) TOPOLOGY: linear (ii) MOLECULE TYPE: protein (xi) SEQUENCE DESCRIPTION: SEQ ID NO:26:

```
Met Ser Asp Trp Leu Thr Phe Gln Lys Lys His Ile Thr Asn Thr Arg
 1               5                  10                  15

Asp Val Asp Cys Asp Asn Ile Met Ser Thr Asn Leu Phe His Cys Lys
                20                  25                  30

Asp Lys Asn Thr Phe Thr Tyr Ser Arg Pro Glu Pro Val Lys Ala Ile
         35                  40                  45

Cys Lys Gly Ile Ile Ala Ser Lys Asn Val Leu Thr Thr Ser Glu Phe
 50                  55                  60

Tyr Leu Ser Asp Cys Asn Val Thr Ser Arg Pro Cys Lys Tyr Lys Leu
 65                  70                  75                  80

Lys Lys Ser Thr Asn Lys Phe Cys Val Thr Cys Glu Asn Gln Ala Pro
                 85                  90                  95

Val His Phe Val Gly Val Gly Ser Cys
                100                 105
```

(2) INFORMATION FOR SEQ ID NO:27:

(i) SEQUENCE CHARACTERISTICS:
        (A) LENGTH: 318 base pairs
        (B) TYPE: nucleic acid
        (C) STRANDEDNESS: single (D) TOPOLOGY: linear (ii) MOLECULE TYPE: DNA (ix) FEATURE:
            (A) NAME/KEY: CDS
            (B) LOCATION: 1..318
            (D) OTHER INFORMATION: /note= "MetLysTyrrOnc"

(xi) SEQUENCE DESCRIPTION: SEQ ID NO:27:

```
ATG AAA TAT GAT TGG CTT ACA TTT CAG AAA AAA CAC ATC ACA AAC ACA       48
Met Lys Tyr Asp Trp Leu Thr Phe Gln Lys Lys His Ile Thr Asn Thr
 1               5                  10                  15

AGG GAT GTT GAT TGT GAT AAT ATC ATG TCA ACA AAC TTG TTC CAC TGC       96
Arg Asp Val Asp Cys Asp Asn Ile Met Ser Thr Asn Leu Phe His Cys
                20                  25                  30

AAG GAC AAG AAC ACT TTT ATC TAT TCA CGT CCT GAG CCA GTG AAG GCC      144
Lys Asp Lys Asn Thr Phe Ile Tyr Ser Arg Pro Glu Pro Val Lys Ala
        35                  40                  45

ATC TGT AAA GGA ATT ATA GCC TCC AAA AAT GTG TTA ACT ACC TCT GAG      192
Ile Cys Lys Gly Ile Ile Ala Ser Lys Asn Val Leu Thr Thr Ser Glu
 50                  55                  60

TTT TAT CTC TCT GAT TGC AAT GTA ACA AGC AGG CCT TGC AAG TAT AAA      240
Phe Tyr Leu Ser Asp Cys Asn Val Thr Ser Arg Pro Cys Lys Tyr Lys
 65                  70                  75                  80

TTA AAG AAA TCA ACT AAT AAA TTT TGT GTA ACT TGT GAA AAT CAG GCA      288
Leu Lys Lys Ser Thr Asn Lys Phe Cys Val Thr Cys Glu Asn Gln Ala
                85                  90                  95

CCA GTT CAT TTT GTT GGA GTT GGA TCT TGT                              318
Pro Val His Phe Val Gly Val Gly Ser Cys
                100                 105
```

(2) INFORMATION FOR SEQ ID NO:28:

(i) SEQUENCE CHARACTERISTICS:
            (A) LENGTH: 106 amino acids
            (B) TYPE: amino acid
            (D) TOPOLOGY: linear (ii) MOLECULE TYPE: protein (xi) SEQUENCE DESCRIPTION: SEQ ID NO:28:

```
Met Lys Tyr Asp Trp Leu Thr Phe Gln Lys Lys His Ile Thr Asn Thr
 1               5                  10                  15

Arg Asp Val Asp Cys Asp Asn Ile Met Ser Thr Asn Leu Phe His Cys
                20                  25                  30

Lys Asp Lys Asn Thr Phe Ile Tyr Ser Arg Pro Glu Pro Val Lys Ala
        35                  40                  45

Ile Cys Lys Gly Ile Ile Ala Ser Lys Asn Val Leu Thr Thr Ser Glu
 50                  55                  60

Phe Tyr Leu Ser Asp Cys Asn Val Thr Ser Arg Pro Cys Lys Tyr Lys
 65                  70                  75                  80

Leu Lys Lys Ser Thr Asn Lys Phe Cys Val Thr Cys Glu Asn Gln Ala
                85                  90                  95

Pro Val His Phe Val Gly Val Gly Ser Cys
                100                 105
```

(2) INFORMATION FOR SEQ ID NO:29:

(i) SEQUENCE CHARACTERISTICS:
            (A) LENGTH: 321 base pairs
            (B) TYPE: nucleic acid
            (C) STRANDEDNESS: single (D) TOPOLOGY: linear (ii) MOLECULE TYPE: DNA (ix) FEATURE:
    (A) NAME/KEY: CDS
    (B) LOCATION: 1..321
    (D) OTHER INFORMATION: /note= "MetAlaAlaTyrrOnc"

(xi) SEQUENCE DESCRIPTION: SEQ ID NO:29:

```
ATG GCT GCT TAT GAT TGG CTT ACA TTT CAG AAA AAA CAC ATC ACA AAC        48
Met Ala Ala Tyr Asp Trp Leu Thr Phe Gln Lys Lys His Ile Thr Asn
 1               5                  10                  15

ACA AGG GAT GTT GAT TGT GAT AAT ATC ATG TCA ACA AAC TTG TTC CAC        96
Thr Arg Asp Val Asp Cys Asp Asn Ile Met Ser Thr Asn Leu Phe His
                20                  25                  30

TGC AAG GAC AAG AAC ACT TTT ATC TAT TCA CGT CCT GAG CCA GTG AAG       144
Cys Lys Asp Lys Asn Thr Phe Ile Tyr Ser Arg Pro Glu Pro Val Lys
        35                  40                  45

GCC ATC TGT AAA GGA ATT ATA GCC TCC AAA AAT GTG TTA ACT ACC TCT       192
Ala Ile Cys Lys Gly Ile Ile Ala Ser Lys Asn Val Leu Thr Thr Ser
50                  55                  60

GAG TTT TAT CTC TCT GAT TGC AAT GTA ACA AGC AGG CCT TGC AAG TAT       240
Glu Phe Tyr Leu Ser Asp Cys Asn Val Thr Ser Arg Pro Cys Lys Tyr
65                  70                  75                  80

AAA TTA AAG AAA TCA ACT AAT AAA TTT TGT GTA ACT TGT GAA AAT CAG       288
Lys Leu Lys Lys Ser Thr Asn Lys Phe Cys Val Thr Cys Glu Asn Gln
                85                  90                  95

GCA CCA GTT CAT TTT GTT GGA GTT GGA TCT TGT                           321
Ala Pro Val His Phe Val Gly Val Gly Ser Cys
                100                 105
```

(2) INFORMATION FOR SEQ ID NO:30:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:30:

```
Met Ala Ala Tyr Asp Trp Leu Thr Phe Gln Lys Lys His Ile Thr Asn
 1               5                  10                  15

Thr Arg Asp Val Asp Cys Asp Asn Ile Met Ser Thr Asn Leu Phe His
                20                  25                  30

Cys Lys Asp Lys Asn Thr Phe Ile Tyr Ser Arg Pro Glu Pro Val Lys
        35                  40                  45

Ala Ile Cys Lys Gly Ile Ile Ala Ser Lys Asn Val Leu Thr Thr Ser
50                  55                  60

Glu Phe Tyr Leu Ser Asp Cys Asn Val Thr Ser Arg Pro Cys Lys Tyr
65                  70                  75                  80

Lys Leu Lys Lys Ser Thr Asn Lys Phe Cys Val Thr Cys Glu Asn Gln
                85                  90                  95

Ala Pro Val His Phe Val Gly Val Gly Ser Cys
                100                 105
```

(2) INFORMATION FOR SEQ ID NO:31:

(i) SEQUENCE CHARACTERISTICS:
        (A) LENGTH: 336 base pairs
        (B) TYPE: nucleic acid
        (C) STRANDEDNESS: single (D) TOPOLOGY: linear (ii) MOLECULE TYPE: DNA (ix) FEATURE:
        (A) NAME/KEY: CDS
        (B) LOCATION: 1..336
        (D) OTHER INFORMATION: /note= "NLSMetSerrOnc"

(xi) SEQUENCE DESCRIPTION: SEQ ID NO:31:

```
CCC AAG AAG AAG CGG AAG GTG ATG TCA GAT TGG CTT ACA TTT CAG AAA        48
Pro Lys Lys Lys Arg Lys Val Met Ser Asp Trp Leu Thr Phe Gln Lys
 1               5                  10                  15

AAA CAC ATC ACA AAC ACA AGG GAT GTT GAT TGT GAT AAT ATC ATG TCA        96
Lys His Ile Thr Asn Thr Arg Asp Val Asp Cys Asp Asn Ile Met Ser
                20                  25                  30

ACA AAC TTG TTC CAC TGC AAG GAC AAG AAC ACT TTT ATC TAT TCA CGT       144
Thr Asn Leu Phe His Cys Lys Asp Lys Asn Thr Phe Ile Tyr Ser Arg
         35                  40                  45

CCT GAG CCA GTG AAG GCC ATC TGT AAA GGA ATT ATA GCC TCC AAA AAT       192
Pro Glu Pro Val Lys Ala Ile Cys Lys Gly Ile Ile Ala Ser Lys Asn
 50                  55                  60

GTG TTA ACT ACC TCT GAG TTT TAT CTC TCT GAT TGC AAT GTA ACA AGC       240
Val Leu Thr Thr Ser Glu Phe Tyr Leu Ser Asp Cys Asn Val Thr Ser
 65                  70                  75                  80

AGG CCT TGC AAG TAT AAA TTA AAG AAA TCA ACT AAT AAA TTT TGT GTA       288
Arg Pro Cys Lys Tyr Lys Leu Lys Lys Ser Thr Asn Lys Phe Cys Val
                 85                  90                  95

ACT TGT GAA AAT CAG GCA CCA GTT CAT TTT GTT GGA GTT GGA TCT TGT       336
Thr Cys Glu Asn Gln Ala Pro Val His Phe Val Gly Val Gly Ser Cys
                100                 105                 110
```

(2) INFORMATION FOR SEQ ID NO:32:

(i) SEQUENCE CHARACTERISTICS:
        (A) LENGTH: 112 amino acids
        (B) TYPE: amino acid
        (D) TOPOLOGY: linear (ii) MOLECULE TYPE: protein (xi) SEQUENCE DESCRIPTION: SEQ ID NO:32:

```
Pro Lys Lys Lys Arg Lys Val Met Ser Asp Trp Leu Thr Phe Gln Lys
 1               5                  10                  15

Lys His Ile Thr Asn Thr Arg Asp Val Asp Cys Asp Asn Ile Met Ser
                20                  25                  30

Thr Asn Leu Phe His Cys Lys Asp Lys Asn Thr Phe Ile Tyr Ser Arg
         35                  40                  45

Pro Glu Pro Val Lys Ala Ile Cys Lys Gly Ile Ile Ala Ser Lys Asn
 50                  55                  60

Val Leu Thr Thr Ser Glu Phe Tyr Leu Ser Asp Cys Asn Val Thr Ser
 65                  70                  75                  80

Arg Pro Cys Lys Tyr Lys Leu Lys Lys Ser Thr Asn Lys Phe Cys Val
                 85                  90                  95

Thr Cys Glu Asn Gln Ala Pro Val His Phe Val Gly Val Gly Ser Cys
                100                 105                 110
```

(2) INFORMATION FOR SEQ ID NO:33:

(i) SEQUENCE CHARACTERISTICS:
        (A) LENGTH: 4 amino acids
        (B) TYPE: amino acid
        (C) STRANDEDNESS:

(D) TOPOLOGY: linear (ii) MOLECULE TYPE: peptide (ix) FEATURE:
            (A) NAME/KEY: Modified-site
            (B) LOCATION: 2
            (D) OTHER INFORMATION: /note= "Xaa = an aliphatic amino acid,
                Ala, Leu, Ile, Val, or Pro"

(ix) FEATURE:
            (A) NAME/KEY: Modified-site
            (B) LOCATION: 3
            (D) OTHER INFORMATION: /note= "Xaa = an aliphatic amino acid,
                Ala, Leu, Ile, Val or Pro"

(ix) FEATURE:
            (A) NAME/KEY: Modified-site
            (B) LOCATION: 4
            (D) OTHER INFORMATION: /note= "Xaa = Ser, Met, Cys, Ala or
                Gln"

(xi) SEQUENCE DESCRIPTION: SEQ ID NO:33:

Cys Xaa Xaa Xaa
1

(2) INFORMATION FOR SEQ ID NO:34:

(i) SEQUENCE CHARACTERISTICS:
            (A) LENGTH: 4 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:34:

Cys Val Ile Met
1

(2) INFORMATION FOR SEQ ID NO:35:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:35:

AGRGATGTKG ATTGYGATAA YATCATG                27

(2) INFORMATION FOR SEQ ID NO:36:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:36:

TGTGARAAYC AGGCMCCWGT KCAYTTT                27

(2) INFORMATION FOR SEQ ID NO:37:

(i) SEQUENCE CHARACTERISTICS:
            (A) LENGTH: 249 base pairs
            (B) TYPE: nucleic acid (C) STRANDEDNESS: single
        (D) TOPOLOGY: linear (ii) MOLECULE TYPE: DNA (ix) FEATURE:
        (A) NAME/KEY: -
        (B) LOCATION: 1..249
        (D) OTHER INFORMATION: /note= "Rana 9"

(xi) SEQUENCE DESCRIPTION: SEQ ID NO:37:

GATGTTGATT GTGATAATAT CATGTCAACA AACTTGTTCC ACTGCAAGGA CAAGAACACT      60

TTTATCTATT CACGTCCTGA GCCAGTGAAG GCCATCTGTA AAGGAATTAT AGCCTCCAAA     120

AATGTGTTAA CTACCTCTGA GTTTTATCTC TCTGATTGCA ATGTAACAAG CAGGCCTTGC     180

AAGTATAAAT TAAAGAAATC AACTAATAAA TTTTGTGTAA CTTGTGAAAA TCAGGCACCA     240

GTTCATTTT                                                             249

(2) INFORMATION FOR SEQ ID NO:38:

(i) SEQUENCE CHARACTERISTICS:
        (A) LENGTH: 315 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..315
        (D) OTHER INFORMATION: /note= "[Met-(-1)]rOnc"

(xi) SEQUENCE DESCRIPTION: SEQ ID NO:38:

```
ATG GAG GAT TGG CTT ACA TTT CAG AAA AAA CAC ATC ACA AAC ACA AGG       48
Met Glu Asp Trp Leu Thr Phe Gln Lys Lys His Ile Thr Asn Thr Arg
 1               5                  10                  15

GAT GTT GAT TGT GAT AAT ATC ATG TCA ACA AAC TTG TTC CAC TGC AAG       96
Asp Val Asp Cys Asp Asn Ile Met Ser Thr Asn Leu Phe His Cys Lys
                20                  25                  30

GAC AAG AAC ACT TTT ATC TAT TCA CGT CCT GAG CCA GTG AAG GCC ATC      144
Asp Lys Asn Thr Phe Ile Tyr Ser Arg Pro Glu Pro Val Lys Ala Ile
            35                  40                  45

TGT AAA GGA ATT ATA GCC TCC AAA AAT GTG TTA ACT ACC TCT GAG TTT      192
Cys Lys Gly Ile Ile Ala Ser Lys Asn Val Leu Thr Thr Ser Glu Phe
        50                  55                  60

TAT CTC TCT GAT TGC AAT GTA ACA AGC AGG CCT TGC AAG TAT AAA TTA      240
Tyr Leu Ser Asp Cys Asn Val Thr Ser Arg Pro Cys Lys Tyr Lys Leu
 65                 70                  75                  80

AAG AAA TCA ACT AAT AAA TTT TGT GTA ACT TGT GAA AAT CAG GCA CCA      288
Lys Lys Ser Thr Asn Lys Phe Cys Val Thr Cys Glu Asn Gln Ala Pro
                85                  90                  95

GTT CAT TTT GTT GGA GTT GGA TCT TGT                                  315
Val His Phe Val Gly Val Gly Ser Cys
                100                 105
```

(2) INFORMATION FOR SEQ ID NO:39:

(i) SEQUENCE CHARACTERISTICS:
        (A) LENGTH: 105 amino acids
        (B) TYPE: amino acid
        (D) TOPOLOGY: linear (ii) MOLECULE TYPE: protein (xi) SEQUENCE DESCRIPTION: SEQ ID NO:39:

```
Met Glu Asp Trp Leu Thr Phe Gln Lys Lys His Ile Thr Asn Thr Arg
  1               5                  10                 15

Asp Val Asp Cys Asp Asn Ile Met Ser Thr Asn Leu Phe His Cys Lys
             20                  25                  30

Asp Lys Asn Thr Phe Ile Tyr Ser Arg Pro Glu Pro Val Lys Ala Ile
         35                  40                  45

Cys Lys Gly Ile Ile Ala Ser Lys Asn Val Leu Thr Thr Ser Glu Phe
         50                  55                  60

Tyr Leu Ser Asp Cys Asn Val Thr Ser Arg Pro Cys Lys Tyr Lys Leu
 65                  70                  75                  80

Lys Lys Ser Thr Asn Lys Phe Cys Val Thr Cys Glu Asn Gln Ala Pro
                 85                  90                  95

Val His Phe Val Gly Val Gly Ser Cys
                100             105

(2) INFORMATION FOR SEQ ID NO:40:

(i) SEQUENCE CHARACTERISTICS:
         (A) LENGTH: 1065 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: CDS
         (B) LOCATION: 1..1065
         (D) OTHER INFORMATION: /note= "sFvFBMetGluOnc"

(xi) SEQUENCE DESCRIPTION: SEQ ID NO:40:
```

| | |
|---|---:|
| GAC ATC AAG ATG ACC CAG TCT CCA TCT TCC ATG TAT GCA TCT CTA GGA<br>Asp Ile Lys Met Thr Gln Ser Pro Ser Ser Met Tyr Ala Ser Leu Gly<br>  1               5                  10                  15 | 48 |
| GAG AGA GTC ACT TTC ACT TGC AAG GCG AGT CAG GAC ATT AAT AAC TAT<br>Glu Arg Val Thr Phe Thr Cys Lys Ala Ser Gln Asp Ile Asn Asn Tyr<br>             20                  25                  30 | 96 |
| TTA TGC TGG TTC CAG CAG AAA CCA GGG AAA TCT CCT AAG ACC CTG ATC<br>Leu Cys Trp Phe Gln Gln Lys Pro Gly Lys Ser Pro Lys Thr Leu Ile<br>         35                  40                  45 | 144 |
| TAT CGT GCA AAC AGA CTG GTA GAT GGG GTC CCA TCA AGG TTC AGT GGC<br>Tyr Arg Ala Asn Arg Leu Val Asp Gly Val Pro Ser Arg Phe Ser Gly<br>     50                  55                  60 | 192 |
| AGT GGA TCT GGA CAA GAT TAT TCT CTC ACC ATT AGC AGC CTG GAG TAT<br>Ser Gly Ser Gly Gln Asp Tyr Ser Leu Thr Ile Ser Ser Leu Glu Tyr<br> 65                  70                  75                  80 | 240 |
| GAA GAT ATG GGA ATT TAT TAT TGT CTA CAG TAT GAT GAG TTT CCG TAC<br>Glu Asp Met Gly Ile Tyr Tyr Cys Leu Gln Tyr Asp Glu Phe Pro Tyr<br>                 85                  90                  95 | 288 |
| ACG TTC GGA GGG GGG ACC AAG CTG GAA ATA AAA GGA GGC GGT GGC TCG<br>Thr Phe Gly Gly Gly Thr Lys Leu Glu Ile Lys Gly Gly Gly Gly Ser<br>            100                 105                 110 | 336 |
| GGC GGT GGC GGA TCG GGT GGC GGC GGC TCT GAG GTT CAG CTC CAG CAG<br>Gly Gly Gly Gly Ser Gly Gly Gly Gly Ser Glu Val Gln Leu Gln Gln<br>        115                 120                 125 | 384 |
| TCT GGG ACT GTA CTG GCA AGG CCT GGG GCT TCA GTG AAG ATG TCC TGC<br>Ser Gly Thr Val Leu Ala Arg Pro Gly Ala Ser Val Lys Met Ser Cys<br>    130                 135                 140 | 432 |
| AAG GCT TCT GGC TAC ACC TTT TCC AGC TAC TGG ATG CAC TGG ATA AAA<br>Lys Ala Ser Gly Tyr Thr Phe Ser Ser Tyr Trp Met His Trp Ile Lys<br>145                 150                 155                 160 | 480 |

```
CAG AGG CCT GGA CAG GGT CTG GAC TGG ATT GTC GCT ATT GAT CCT CGA    528
Gln Arg Pro Gly Gln Gly Leu Asp Trp Ile Val Ala Ile Asp Pro Arg
            165                 170                 175

AAT AGT GAT ACT ATT TAC AAC CCG CAA TTC AAA CAC AAG GCC AAA CTG    576
Asn Ser Asp Thr Ile Tyr Asn Pro Gln Phe Lys His Lys Ala Lys Leu
        180                 185                 190

ACT GCA GTC ACC TCC ACC AGC ACT GCC TAC ATG GAA CTC AAC AGC CTG    624
Thr Ala Val Thr Ser Thr Ser Thr Ala Tyr Met Glu Leu Asn Ser Leu
            195                 200                 205

ACA AAT GAG GAC TCT GCG GTC TAT TAC TGT ACC CCT CTT TAT TAC TTT    672
Thr Asn Glu Asp Ser Ala Val Tyr Tyr Cys Thr Pro Leu Tyr Tyr Phe
        210                 215                 220

GAC TCC TGG GGC CAA GGC ACC ACT CTC ACA GTC TCC TCA GCC AAG AAA    720
Asp Ser Trp Gly Gln Gly Thr Thr Leu Thr Val Ser Ser Ala Lys Lys
225                 230                 235                 240

CTG AAC GAC GCT CAG GCG CCG AAG AGT GAT ATG GAG GAT TGG CTT ACA    768
Leu Asn Asp Ala Gln Ala Pro Lys Ser Asp Met Glu Asp Trp Leu Thr
                245                 250                 255

TTT CAG AAA AAA CAC ATC ACA AAC ACA AGG GAT GTT GAT TGT GAT AAT    816
Phe Gln Lys Lys His Ile Thr Asn Thr Arg Asp Val Asp Cys Asp Asn
            260                 265                 270

ATC ATG TCA ACA AAC TTG TTC CAC TGC AAG GAC AAG AAC ACT TTT ATC    864
Ile Met Ser Thr Asn Leu Phe His Cys Lys Asp Lys Asn Thr Phe Ile
        275                 280                 285

TAT TCA CGT CCT GAG CCA GTG AAG GCC ATC TGT AAA GGA ATT ATA GCC    912
Tyr Ser Arg Pro Glu Pro Val Lys Ala Ile Cys Lys Gly Ile Ile Ala
    290                 295                 300

TCC AAA AAT GTG TTA ACT ACC TCT GAG TTT TAT CTC TCT GAT TGC AAT    960
Ser Lys Asn Val Leu Thr Thr Ser Glu Phe Tyr Leu Ser Asp Cys Asn
305                 310                 315                 320

GTA ACA AGC AGG CCT TGC AAG TAT AAA TTA AAG AAA TCA ACT AAT AAA    1008
Val Thr Ser Arg Pro Cys Lys Tyr Lys Leu Lys Lys Ser Thr Asn Lys
                325                 330                 335

TTT TGT GTA ACT TGT GAA AAT CAG GCA CCA GTT CAT TTT GTT GGA GTT    1056
Phe Cys Val Thr Cys Glu Asn Gln Ala Pro Val His Phe Val Gly Val
            340                 345                 350

GGA TCT TGT                                                        1065
Gly Ser Cys
        355
```

(2) INFORMATION FOR SEQ ID NO:41:

(i) SEQUENCE CHARACTERISTICS:
        (A) LENGTH: 355 amino acids
        (B) TYPE: amino acid
        (D) TOPOLOGY: linear (ii) MOLECULE TYPE: protein (xi) SEQUENCE DESCRIPTION: SEQ ID NO:41:

```
Asp Ile Lys Met Thr Gln Ser Pro Ser Ser Met Tyr Ala Ser Leu Gly
 1               5                  10                  15

Glu Arg Val Thr Phe Thr Cys Lys Ala Ser Gln Asp Ile Asn Asn Tyr
                20                  25                  30

Leu Cys Trp Phe Gln Gln Lys Pro Gly Lys Ser Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
65                  70                  75                  80
```

```
Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Glu Val Gln Leu Gln Gln
        115                 120                 125

Ser Gly Thr Val Leu Ala Arg Pro Gly Ala Ser Val Lys Met Ser Cys
    130                 135                 140

Lys Ala Ser Gly Tyr Thr Phe Ser Ser Tyr Trp Met His Trp Ile Lys
145                 150                 155                 160

Gln Arg Pro Gly Gln Gly Leu Asp Trp Ile Val Ala Ile Asp Pro Arg
                165                 170                 175

Asn Ser Asp Thr Ile Tyr Asn Pro Gln Phe Lys His Lys Ala Lys Leu
                180                 185                 190

Thr Ala Val Thr Ser Thr Ser Thr Ala Tyr Met Glu Leu Asn Ser Leu
            195                 200                 205

Thr Asn Glu Asp Ser Ala Val Tyr Tyr Cys Thr Pro Leu Tyr Tyr Phe
210                 215                 220

Asp Ser Trp Gly Gln Gly Thr Thr Leu Thr Val Ser Ser Ala Lys Lys
225                 230                 235                 240

Leu Asn Asp Ala Gln Ala Pro Lys Ser Asp Met Glu Asp Trp Leu Thr
                245                 250                 255

Phe Gln Lys Lys His Ile Thr Asn Thr Arg Asp Val Asp Cys Asp Asn
                260                 265                 270

Ile Met Ser Thr Asn Leu Phe His Cys Lys Asp Lys Asn Thr Phe Ile
            275                 280                 285

Tyr Ser Arg Pro Glu Pro Val Lys Ala Ile Cys Lys Gly Ile Ile Ala
            290                 295                 300

Ser Lys Asn Val Leu Thr Ser Glu Phe Tyr Leu Ser Asp Cys Asn
305                 310                 315                 320

Val Thr Ser Arg Pro Cys Lys Tyr Lys Leu Lys Lys Ser Thr Asn Lys
                325                 330                 335

Phe Cys Val Thr Cys Glu Asn Gln Ala Pro Val His Phe Val Gly Val
                340                 345                 350

Gly Ser Cys
        355

(2) INFORMATION FOR SEQ ID NO:42:

(i) SEQUENCE CHARACTERISTICS:
        (A) LENGTH: 1137 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..1137
        (D) OTHER INFORMATION: /note= "SigPepGlnOncFBE6"

(xi) SEQUENCE DESCRIPTION: SEQ ID NO:42:

ATG GGT CTG GAA AAA TCT CTG ATC CTG TTC CCG CTG TTC TTC CTG CTG      48
Met Gly Leu Glu Lys Ser Leu Ile Leu Phe Pro Leu Phe Phe Leu Leu
 1               5                  10                  15

CTG GGT TGG GTT CAG CCG TCT CTG GGT CAG GAT TGG CTT ACA TTT CAG      96
Leu Gly Trp Val Gln Pro Ser Leu Gly Gln Asp Trp Leu Thr Phe Gln
```

```
      20                  25                  30
AAA AAA CAC ATC ACA AAC ACA AGG GAT GTT GAT TGT GAT AAT ATC ATG     144
Lys Lys His Ile Thr Asn Thr Arg Asp Val Asp Cys Asp Asn Ile Met
             35                  40                  45

TCA ACA AAC TTG TTC CAC TGC AAG GAC AAG AAC ACT TTT ATC TAT TCA     192
Ser Thr Asn Leu Phe His Cys Lys Asp Lys Asn Thr Phe Ile Tyr Ser
         50                  55                  60

CGT CCT GAG CCA GTG AAG GCC ATC TGT AAA GGA ATT ATA GCC TCC AAA     240
Arg Pro Glu Pro Val Lys Ala Ile Cys Lys Gly Ile Ile Ala Ser Lys
 65                  70                  75                  80

AAT GTG TTA ACT ACC TCT GAG TTT TAT CTC TCT GAT TGC AAT GTA ACA     288
Asn Val Leu Thr Thr Ser Glu Phe Tyr Leu Ser Asp Cys Asn Val Thr
                 85                  90                  95

AGC AGG CCT TGC AAG TAT AAA TTA AAG AAA TCA ACT AAT AAA TTT TGT     336
Ser Arg Pro Cys Lys Tyr Lys Leu Lys Lys Ser Thr Asn Lys Phe Cys
            100                 105                 110

GTA ACT TGT GAA AAT CAG GCA CCA GTT CAT TTT GTT GGA GTT GGA TCT     384
Val Thr Cys Glu Asn Gln Ala Pro Val His Phe Val Gly Val Gly Ser
        115                 120                 125

TGT GCC AAG AAA CTG AAC GAC GCT CAG GCG CCG AAG AGT GAT GAC ATC     432
Cys Ala Lys Lys Leu Asn Asp Ala Gln Ala Pro Lys Ser Asp Asp Ile
    130                 135                 140

AAG ATG ACC CAG TCT CCA TCT TCC ATG TAT GCA TCT CTA GGA GAG AGA     480
Lys Met Thr Gln Ser Pro Ser Ser Met Tyr Ala Ser Leu Gly Glu Arg
145                 150                 155                 160

GTC ACT TTC ACT TGC AAG GCG AGT CAG GAC ATT AAT AAC TAT TTA TGC     528
Val Thr Phe Thr Cys Lys Ala Ser Gln Asp Ile Asn Asn Tyr Leu Cys
                165                 170                 175

TGG TTC CAG CAG AAA CCA GGG AAA TCT CCT AAG ACC CTG ATC TAT CGT     576
Trp Phe Gln Gln Lys Pro Gly Lys Ser Pro Lys Thr Leu Ile Tyr Arg
            180                 185                 190

GCA AAC AGA CTG GTA GAT GGG GTC CCA TCA AGG TTC AGT GGC AGT GGA     624
Ala Asn Arg Leu Val Asp Gly Val Pro Ser Arg Phe Ser Gly Ser Gly
        195                 200                 205

TCT GGA CAA GAT TAT TCT CTC ACC ATT AGC AGC CTG GAG TAT GAA GAT     672
Ser Gly Gln Asp Tyr Ser Leu Thr Ile Ser Ser Leu Glu Tyr Glu Asp
    210                 215                 220

ATG GGA ATT TAT TAT TGT CTA CAG TAT GAT GAG TTT CCG TAC ACG TTC     720
Met Gly Ile Tyr Tyr Cys Leu Gln Tyr Asp Glu Phe Pro Tyr Thr Phe
225                 230                 235                 240

GGA GGG GGG ACC AAG CTG GAA ATA AAA GGA GGC GGT GGC TCG GGC GGT     768
Gly Gly Gly Thr Lys Leu Glu Ile Lys Gly Gly Gly Gly Ser Gly Gly
                245                 250                 255

GGC GGA TCG GGT GGC GGC GGC TCT GAG GTT CAG CTC CAG CAG TCT GGG     816
Gly Gly Ser Gly Gly Gly Gly Ser Glu Val Gln Leu Gln Gln Ser Gly
            260                 265                 270

ACT GTA CTG GCA AGG CCT GGG GCT TCA GTG AAG ATG TCC TGC AAG GCT     864
Thr Val Leu Ala Arg Pro Gly Ala Ser Val Lys Met Ser Cys Lys Ala
        275                 280                 285

TCT GGC TAC ACC TTT TCC AGC TAC TGG ATG CAC TGG ATA AAA CAG AGG     912
Ser Gly Tyr Thr Phe Ser Ser Tyr Trp Met His Trp Ile Lys Gln Arg
    290                 295                 300

CCT GGA CAG GGT CTG GAC TGG ATT GTG GCT ATT GAT CCT CGA AAT AGT     960
Pro Gly Gln Gly Leu Asp Trp Ile Val Ala Ile Asp Pro Arg Asn Ser
305                 310                 315                 320

GAT ACT ATT TAC AAC CCG CAA TTC AAA CAC AAG GCC AAA CTG ACT GCA    1008
Asp Thr Ile Tyr Asn Pro Gln Phe Lys His Lys Ala Lys Leu Thr Ala
                325                 330                 335

GTC ACC TCC ACC AGC ACT GCC TAC ATG GAA CTC AAC AGC CTG ACA AAT    1056
```

```
Val Thr Ser Thr Ser Thr Ala Tyr Met Glu Leu Asn Ser Leu Thr Asn
            340                 345                 350

GAG GAC TCT GCG GTC TAT TAC TGT ACC CCT CTT TAT TAC TTT GAC TCC     1104
Glu Asp Ser Ala Val Tyr Tyr Cys Thr Pro Leu Tyr Tyr Phe Asp Ser
            355                 360                 365

TGG GGC CAA GGC ACC ACT CTC ACA GTC TCC TCA                         1137
Trp Gly Gln Gly Thr Thr Leu Thr Val Ser Ser
            370                 375
```

(2) INFORMATION FOR SEQ ID NO:43:

(i) SEQUENCE CHARACTERISTICS:
        (A) LENGTH: 379 amino acids
        (B) TYPE: amino acid
        (D) TOPOLOGY: linear (ii) MOLECULE TYPE: protein (xi) SEQUENCE DESCRIPTION: SEQ ID NO:43:

```
Met Gly Leu Glu Lys Ser Leu Ile Leu Phe Pro Leu Phe Leu Leu
 1               5                  10                  15

Leu Gly Trp Val Gln Pro Ser Leu Gly Gln Asp Trp Leu Thr Phe Gln
            20                  25                  30

Lys Lys His Ile Thr Asn Thr Arg Asp Val Asp Cys Asp Asn Ile Met
            35                  40                  45

Ser Thr Asn Leu Phe His Cys Lys Asp Lys Asn Thr Phe Ile Tyr Ser
            50                  55                  60

Arg Pro Glu Pro Val Lys Ala Ile Cys Lys Gly Ile Ile Ala Ser Lys
 65                 70                  75                  80

Asn Val Leu Thr Thr Ser Glu Phe Tyr Leu Ser Asp Cys Asn Val Thr
                85                  90                  95

Ser Arg Pro Cys Lys Tyr Lys Leu Lys Lys Ser Thr Asn Lys Phe Cys
            100                 105                 110

Val Thr Cys Glu Asn Gln Ala Pro Val His Phe Val Gly Val Gly Ser
            115                 120                 125

Cys Ala Lys Lys Leu Asn Asp Ala Gln Ala Pro Lys Ser Asp Asp Ile
            130                 135                 140

Lys Met Thr Gln Ser Pro Ser Ser Met Tyr Ala Ser Leu Gly Glu Arg
145                 150                 155                 160

Val Thr Phe Thr Cys Lys Ala Ser Gln Asp Ile Asn Asn Tyr Leu Cys
            165                 170                 175

Trp Phe Gln Gln Lys Pro Gly Lys Ser Pro Lys Thr Leu Ile Tyr Arg
            180                 185                 190

Ala Asn Arg Leu Val Asp Gly Val Pro Ser Arg Phe Ser Gly Ser Gly
            195                 200                 205

Ser Gly Gln Asp Tyr Ser Leu Thr Ile Ser Ser Leu Glu Tyr Glu Asp
            210                 215                 220

Met Gly Ile Tyr Tyr Cys Leu Gln Tyr Asp Glu Phe Pro Tyr Thr Phe
225                 230                 235                 240

Gly Gly Gly Thr Lys Leu Glu Ile Lys Gly Gly Gly Ser Gly Gly
            245                 250                 255

Gly Gly Ser Gly Gly Gly Gly Ser Glu Val Gln Leu Gln Gln Ser Gly
            260                 265                 270

Thr Val Leu Ala Arg Pro Gly Ala Ser Val Lys Met Ser Cys Lys Ala
            275                 280                 285

Ser Gly Tyr Thr Phe Ser Ser Tyr Trp Met His Trp Ile Lys Gln Arg
            290                 295                 300
```

```
Pro Gly Gln Gly Leu Asp Trp Ile Val Ala Ile Asp Pro Arg Asn Ser
305                 310                 315                 320

Asp Thr Ile Tyr Asn Pro Gln Phe Lys His Lys Ala Lys Leu Thr Ala
            325                 330                 335

Val Thr Ser Thr Ser Thr Ala Tyr Met Glu Leu Asn Ser Leu Thr Asn
            340                 345                 350

Glu Asp Ser Ala Val Tyr Tyr Cys Thr Pro Leu Tyr Tyr Phe Asp Ser
            355                 360                 365

Trp Gly Gln Gly Thr Thr Leu Thr Val Ser Ser
370                 375
```

(2) INFORMATION FOR SEQ ID NO:44:

(i) SEQUENCE CHARACTERISTICS:
        (A) LENGTH: 1074 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..1074
        (D) OTHER INFORMATION: /note= "MetSerOncA87FBE6"

(xi) SEQUENCE DESCRIPTION: SEQ ID NO:44:

```
ATG TCA GAT TGG CTT ACA TTT CAG AAA AAA CAC ATC ACA AAC ACA AGG      48
Met Ser Asp Trp Leu Thr Phe Gln Lys Lys His Ile Thr Asn Thr Arg
 1               5                  10                  15

GAT GTT GAT TGT GAT AAT ATC ATG TCA ACA AAC TTG TTC CAC TGC AAG      96
Asp Val Asp Cys Asp Asn Ile Met Ser Thr Asn Leu Phe His Cys Lys
                20                  25                  30

GAC AAG AAC ACT TTT ATC TAT TCA CGT CCT GAG CCA GTG AAG GCC ATC     144
Asp Lys Asn Thr Phe Ile Tyr Ser Arg Pro Glu Pro Val Lys Ala Ile
            35                  40                  45

TGT AAA GGA ATT ATA GCC TCC AAA AAT GTG TTA ACT ACC TCT GAG TTT     192
Cys Lys Gly Ile Ile Ala Ser Lys Asn Val Leu Thr Thr Ser Glu Phe
 50                  55                  60

TAT CTC TCT GAT TGC AAT GTA ACA AGC AGG CCT TGC AAG TAT AAA TTA     240
Tyr Leu Ser Asp Cys Asn Val Thr Ser Arg Pro Cys Lys Tyr Lys Leu
 65                  70                  75                  80

AAG AAA TCA ACT AAT AAA TTT GCT GTA ACT TGT GAA AAT CAG GCA CCA     288
Lys Lys Ser Thr Asn Lys Phe Ala Val Thr Cys Glu Asn Gln Ala Pro
                85                  90                  95

GTT CAT TTT GTT GGA GTT GGA TCT TGT GCC AAG AAA CTG AAC GAC GCT     336
Val His Phe Val Gly Val Gly Ser Cys Ala Lys Lys Leu Asn Asp Ala
            100                 105                 110

CAG GCG CCG AAG AGT GAT GAC ATC AAG ATG ACC CAG TCT CCA TCT TCC     384
Gln Ala Pro Lys Ser Asp Asp Ile Lys Met Thr Gln Ser Pro Ser Ser
        115                 120                 125

ATG TAT GCA TCT CTA GGA GAG AGA GTC ACT TTC ACT TGC AAG GCG AGT     432
Met Tyr Ala Ser Leu Gly Glu Arg Val Thr Phe Thr Cys Lys Ala Ser
    130                 135                 140

CAG GAC ATT AAT AAC TAT TTA TGC TGG TTC CAG CAG AAA CCA GGG AAA     480
Gln Asp Ile Asn Asn Tyr Leu Cys Trp Phe Gln Gln Lys Pro Gly Lys
145                 150                 155                 160

TCT CCT AAG ACC CTG ATC TAT CGT GCA AAC AGA CTG GTA GAT GGG GTC     528
Ser Pro Lys Thr Leu Ile Tyr Arg Ala Asn Arg Leu Val Asp Gly Val
                165                 170                 175

CCA TCA AGG TTC AGT GGC AGT GGA TCT GGA CAA GAT TAT TCT CTC ACC     576
```

```
Pro Ser Arg Phe Ser Gly Ser Gly Ser Gly Gln Asp Tyr Ser Leu Thr
            180                 185                 190

ATT AGC AGC CTG GAG TAT GAA GAT ATG GGA ATT TAT TAT TGT CTA CAG        624
Ile Ser Ser Leu Glu Tyr Glu Asp Met Gly Ile Tyr Tyr Cys Leu Gln
            195                 200                 205

TAT GAT GAG TTT CCG TAC ACG TTC GGA GGG GGG ACC AAG CTG GAA ATA        672
Tyr Asp Glu Phe Pro Tyr Thr Phe Gly Gly Gly Thr Lys Leu Glu Ile
        210                 215                 220

AAA GGA GGC GGT GGC TCG GGC GGT GGC GGA TCG GGT GGC GGC GGC TCT        720
Lys Gly Gly Gly Gly Ser Gly Gly Gly Gly Ser Gly Gly Gly Gly Ser
225                 230                 235                 240

GAG GTT CAG CTC CAG CAG TCT GGG ACT GTA CTG GCA AGG CCT GGG GCT        768
Glu Val Gln Leu Gln Gln Ser Gly Thr Val Leu Ala Arg Pro Gly Ala
                245                 250                 255

TCA GTG AAG ATG TCC TGC AAG GCT TCT GGC TAC ACC TTT TCC AGC TAC        816
Ser Val Lys Met Ser Cys Lys Ala Ser Gly Tyr Thr Phe Ser Ser Tyr
            260                 265                 270

TGG ATG CAC TGG ATA AAA CAG AGG CCT GGA CAG GGT CTG GAC TGG ATT        864
Trp Met His Trp Ile Lys Gln Arg Pro Gly Gln Gly Leu Asp Trp Ile
            275                 280                 285

GTC GCT ATT GAT CCT CGA AAT AGT GAT ACT ATT TAC AAC CCG CAA TTC        912
Val Ala Ile Asp Pro Arg Asn Ser Asp Thr Ile Tyr Asn Pro Gln Phe
        290                 295                 300

AAA CAC AAG GCC AAA CTG ACT GCA GTC ACC TCC ACC AGC ACT GCC TAC        960
Lys His Lys Ala Lys Leu Thr Ala Val Thr Ser Thr Ser Thr Ala Tyr
305                 310                 315                 320

ATG GAA CTC AAC AGC CTG ACA AAT GAG GAC TCT GCG GTC TAT TAC TGT       1008
Met Glu Leu Asn Ser Leu Thr Asn Glu Asp Ser Ala Val Tyr Tyr Cys
                325                 330                 335

ACC CCT CTT TAT TAC TTT GAC TCC TGG GGC CAA GGC ACC ACT CTC ACA       1056
Thr Pro Leu Tyr Tyr Phe Asp Ser Trp Gly Gln Gly Thr Thr Leu Thr
            340                 345                 350

GTC TCC TCA CAT CAC CAT                                                1074
Val Ser Ser His His His
            355

(2) INFORMATION FOR SEQ ID NO:45:

(i) SEQUENCE CHARACTERISTICS:
        (A) LENGTH: 358 amino acids
        (B) TYPE: amino acid
        (D) TOPOLOGY: linear (ii) MOLECULE TYPE: protein (xi) SEQUENCE DESCRIPTION: SEQ ID NO:45:

Met Ser Asp Trp Leu Thr Phe Gln Lys Lys His Ile Thr Asn Thr Arg
 1               5                  10                  15

Asp Val Asp Cys Asp Asn Ile Met Ser Thr Asn Leu Phe His Cys Lys
                20                  25                  30

Asp Lys Asn Thr Phe Ile Tyr Ser Arg Pro Glu Pro Val Lys Ala Ile
            35                  40                  45

Cys Lys Gly Ile Ile Ala Ser Lys Asn Val Leu Thr Ser Glu Phe
        50                  55                  60

Tyr Leu Ser Asp Cys Asn Val Thr Ser Arg Pro Cys Lys Tyr Lys Leu
 65                 70                  75                  80

Lys Lys Ser Thr Asn Lys Phe Ala Val Thr Cys Glu Asn Gln Ala Pro
                85                  90                  95

Val His Phe Val Gly Val Gly Ser Cys Ala Lys Lys Leu Asn Asp Ala
            100                 105                 110
```

-continued

```
Gln Ala Pro Lys Ser Asp Asp Ile Lys Met Thr Gln Ser Pro Ser Ser
        115                 120                 125
Met Tyr Ala Ser Leu Gly Glu Arg Val Thr Phe Thr Cys Lys Ala Ser
130                 135                 140
Gln Asp Ile Asn Asn Tyr Leu Cys Trp Phe Gln Gln Lys Pro Gly Lys
145                 150                 155                 160
Ser Pro Lys Thr Leu Ile Tyr Arg Ala Asn Arg Leu Val Asp Gly Val
                165                 170                 175
Pro Ser Arg Phe Ser Gly Ser Gly Ser Gly Gln Asp Tyr Ser Leu Thr
            180                 185                 190
Ile Ser Ser Leu Glu Tyr Glu Asp Met Gly Ile Tyr Tyr Cys Leu Gln
        195                 200                 205
Tyr Asp Glu Phe Pro Tyr Thr Phe Gly Gly Gly Thr Lys Leu Glu Ile
210                 215                 220
Lys Gly Gly Gly Gly Ser Gly Gly Gly Ser Gly Gly Gly Gly Gly Ser
225                 230                 235                 240
Glu Val Gln Leu Gln Gln Ser Gly Thr Val Leu Ala Arg Pro Gly Ala
                245                 250                 255
Ser Val Lys Met Ser Cys Lys Ala Ser Gly Tyr Thr Phe Ser Ser Tyr
            260                 265                 270
Trp Met His Trp Ile Lys Gln Arg Pro Gly Gln Gly Leu Asp Trp Ile
        275                 280                 285
Val Ala Ile Asp Pro Arg Asn Ser Asp Thr Ile Tyr Asn Pro Gln Phe
290                 295                 300
Lys His Lys Ala Lys Leu Thr Ala Val Thr Ser Thr Ser Thr Ala Tyr
305                 310                 315                 320
Met Glu Leu Asn Ser Leu Thr Asn Glu Asp Ser Ala Val Tyr Tyr Cys
                325                 330                 335
Thr Pro Leu Tyr Tyr Phe Asp Ser Trp Gly Gln Gly Thr Thr Leu Thr
            340                 345                 350
Val Ser Ser His His His
        355
```

(2) INFORMATION FOR SEQ ID NO:46:

(i) SEQUENCE CHARACTERISTICS:
        (A) LENGTH: 1086 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..1083
        (D) OTHER INFORMATION: /note= "MetSerOncAngsFv"

(xi) SEQUENCE DESCRIPTION: SEQ ID NO:46:

```
ATG TCA GAT TGG CTT ACA TTT CAG AAA AAA CAC ATC ACA AAC ACA AGG      48
Met Ser Asp Trp Leu Thr Phe Gln Lys Lys His Ile Thr Asn Thr Arg
 1               5                  10                  15

GAT GTT GAT TGT GAT AAT ATC ATG TCA ACA AAC TTG TTC CAC TGC AAG      96
Asp Val Asp Cys Asp Asn Ile Met Ser Thr Asn Leu Phe His Cys Lys
                20                  25                  30

GAC AAG AAC ACT TTT ATC TAT TCA CGT CCT GAG CCA GTG AAG GCC ATC     144
Asp Lys Asn Thr Phe Ile Tyr Ser Arg Pro Glu Pro Val Lys Ala Ile
            35                  40                  45
```

```
TGT AAA GGA ATT ATA GCC TCC AAA AAT GTG TTA ACT ACC TCT GAG TTT        192
Cys Lys Gly Ile Ile Ala Ser Lys Asn Val Leu Thr Thr Ser Glu Phe
 50                  55                  60

TAT CTC TCT GAT TGC AAT GTA ACA AGC AGG CCT TGC AAG TAT AAA TTA        240
Tyr Leu Ser Asp Cys Asn Val Thr Ser Arg Pro Cys Lys Tyr Lys Leu
 65                  70                  75                  80

AAG AAA TCA ACT AAT AAA TTT GTT GTT GCT TGT GAA AAT GGC TTA CCT        288
Lys Lys Ser Thr Asn Lys Phe Val Val Ala Cys Glu Asn Gly Leu Pro
                 85                  90                  95

GTC CAC TTG GAT CAG TCA ATT TTC CGT CGT CCG GCC AAG AAA CTG AAC        336
Val His Leu Asp Gln Ser Ile Phe Arg Arg Pro Ala Lys Lys Leu Asn
        100                 105                 110

GAC GCT CAG GCG CCG AAG AGT GAT GAC ATC AAG ATG ACC CAG TCT CCA        384
Asp Ala Gln Ala Pro Lys Ser Asp Asp Ile Lys Met Thr Gln Ser Pro
            115                 120                 125

TCT TCC ATG TAT GCA TCT CTA GGA GAG AGA GTC ACT TTC ACT TGC AAG        432
Ser Ser Met Tyr Ala Ser Leu Gly Glu Arg Val Thr Phe Thr Cys Lys
130                 135                 140

GCG AGT CAG GAC ATT AAT AAC TAT TTA TGC TGG TTC CAG CAG AAA CCA        480
Ala Ser Gln Asp Ile Asn Asn Tyr Leu Cys Trp Phe Gln Gln Lys Pro
145                 150                 155                 160

GGG AAA TCT CCT AAG ACC CTG ATC TAT CGT GCA AAC AGA CTG GTA GAT        528
Gly Lys Ser Pro Lys Thr Leu Ile Tyr Arg Ala Asn Arg Leu Val Asp
                165                 170                 175

GGG GTC CCA TCA AGG TTC AGT GGC AGT GGA TCT GGA CAA GAT TAT TCT        576
Gly Val Pro Ser Arg Phe Ser Gly Ser Gly Ser Gly Gln Asp Tyr Ser
            180                 185                 190

CTC ACC ATT AGC AGC CTG GAG TAT GAA GAT ATG GGA ATT TAT TAT TGT        624
Leu Thr Ile Ser Ser Leu Glu Tyr Glu Asp Met Gly Ile Tyr Tyr Cys
                195                 200                 205

CTA CAG TAT GAT GAG TTT CCG TAC ACG TTC GGA GGG GGG ACC AAG CTG        672
Leu Gln Tyr Asp Glu Phe Pro Tyr Thr Phe Gly Gly Gly Thr Lys Leu
        210                 215                 220

GAA ATA AAA GGA GGC GGT GGC TCG GGC GGT GGC GGA TCG GGT GGC GGC        720
Glu Ile Lys Gly Gly Gly Gly Ser Gly Gly Gly Gly Ser Gly Gly Gly
225                 230                 235                 240

GGC TCT GAG GTT CAG CTC CAG CAG TCT GGG ACT GTA CTG GCA AGG CCT        768
Gly Ser Glu Val Gln Leu Gln Gln Ser Gly Thr Val Leu Ala Arg Pro
                245                 250                 255

GGG GCT TCA GTG AAG ATG TCC TGC AAG GCT TCT GGC TAC ACC TTT TCC        816
Gly Ala Ser Val Lys Met Ser Cys Lys Ala Ser Gly Tyr Thr Phe Ser
            260                 265                 270

AGC TAC TGG ATG CAC TGG ATA AAA CAG AGG CCT GGA CAG GGT CTG GAC        864
Ser Tyr Trp Met His Trp Ile Lys Gln Arg Pro Gly Gln Gly Leu Asp
                275                 280                 285

TGG ATT GTC GCT ATT GAT CCT CGA AAT AGT GAT ACT ATT TAC AAC CCG        912
Trp Ile Val Ala Ile Asp Pro Arg Asn Ser Asp Thr Ile Tyr Asn Pro
290                 295                 300

CAA TTC AAA CAC AAG GCC AAA CTG ACT GCA GTC ACC TCC ACC AGC ACT        960
Gln Phe Lys His Lys Ala Lys Leu Thr Ala Val Thr Ser Thr Ser Thr
305                 310                 315                 320

GCC TAC ATG GAA CTC AAC AGC CTG ACA AAT GAG GAC TCT GCG GTC TAT       1008
Ala Tyr Met Glu Leu Asn Ser Leu Thr Asn Glu Asp Ser Ala Val Tyr
                325                 330                 335

TAC TGT ACC CCT CTT TAT TAC TTT GAC TCC TGG GGC CAA GGC ACC ACT       1056
Tyr Cys Thr Pro Leu Tyr Tyr Phe Asp Ser Trp Gly Gln Gly Thr Thr
            340                 345                 350

CTC ACA GTC TCC TCA CAT CAC CAT TAGTAG                                 1086
Leu Thr Val Ser Ser His His His
                355                 360
```

(2) INFORMATION FOR SEQ ID NO:47:

(i) SEQUENCE CHARACTERISTICS:
        (A) LENGTH: 360 amino acids
        (B) TYPE: amino acid
        (D) TOPOLOGY: linear (ii) MOLECULE TYPE: protein (xi) SEQUENCE DESCRIPTION: SEQ ID NO:47:

```
Met Ser Asp Trp Leu Thr Phe Gln Lys Lys His Ile Thr Asn Thr Arg
 1               5                  10                  15

Asp Val Asp Cys Asp Asn Ile Met Ser Thr Asn Leu Phe His Cys Lys
                20                  25                  30

Asp Lys Asn Thr Phe Ile Tyr Ser Arg Pro Glu Pro Val Lys Ala Ile
            35                  40                  45

Cys Lys Gly Ile Ile Ala Ser Lys Asn Val Leu Thr Thr Ser Glu Phe
 50                  55                  60

Tyr Leu Ser Asp Cys Asn Val Thr Ser Arg Pro Cys Lys Tyr Lys Leu
 65                  70                  75                  80

Lys Lys Ser Thr Asn Lys Phe Val Val Ala Cys Glu Asn Gly Leu Pro
                85                  90                  95

Val His Leu Asp Gln Ser Ile Phe Arg Arg Pro Ala Lys Lys Leu Asn
                100                 105                 110

Asp Ala Gln Ala Pro Lys Ser Asp Asp Ile Lys Met Thr Gln Ser Pro
            115                 120                 125

Ser Ser Met Tyr Ala Ser Leu Gly Glu Arg Val Thr Phe Thr Cys Lys
130                 135                 140

Ala Ser Gln Asp Ile Asn Asn Tyr Leu Cys Trp Phe Gln Gln Lys Pro
145                 150                 155                 160

Gly Lys Ser Pro Lys Thr Leu Ile Tyr Arg Ala Asn Arg Leu Val Asp
                165                 170                 175

Gly Val Pro Ser Arg Phe Ser Gly Ser Gly Ser Gly Gln Asp Tyr Ser
                180                 185                 190

Leu Thr Ile Ser Ser Leu Glu Tyr Glu Asp Met Gly Ile Tyr Tyr Cys
            195                 200                 205

Leu Gln Tyr Asp Glu Phe Pro Tyr Thr Phe Gly Gly Gly Thr Lys Leu
210                 215                 220

Glu Ile Lys Gly Gly Gly Gly Ser Gly Gly Gly Gly Ser Gly Gly Gly
225                 230                 235                 240

Gly Ser Glu Val Gln Leu Gln Gln Ser Gly Thr Val Leu Ala Arg Pro
                245                 250                 255

Gly Ala Ser Val Lys Met Ser Cys Lys Ala Ser Gly Tyr Thr Phe Ser
                260                 265                 270

Ser Tyr Trp Met His Trp Ile Lys Gln Arg Pro Gly Gln Gly Leu Asp
            275                 280                 285

Trp Ile Val Ala Ile Asp Pro Arg Asn Ser Asp Thr Ile Tyr Asn Pro
290                 295                 300

Gln Phe Lys His Lys Ala Lys Leu Thr Ala Val Thr Ser Thr Ser Thr
305                 310                 315                 320

Ala Tyr Met Glu Leu Asn Ser Leu Thr Asn Glu Asp Ser Ala Val Tyr
                325                 330                 335

Tyr Cys Thr Pro Leu Tyr Tyr Phe Asp Ser Trp Gly Gln Gly Thr Thr
                340                 345                 350
```

```
Leu Thr Val Ser Ser His His His
        355                 360

(2) INFORMATION FOR SEQ ID NO:48:

(i) SEQUENCE CHARACTERISTICS:
        (A) LENGTH: 1065 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..1065
        (D) OTHER INFORMATION: /note= "sFvOncMetSer"

(xi) SEQUENCE DESCRIPTION: SEQ ID NO:48:

GAC ATC AAG ATG ACC CAG TCT CCA TCT TCC ATG TAT GCA TCT CTA GGA      48
Asp Ile Lys Met Thr Gln Ser Pro Ser Ser Met Tyr Ala Ser Leu Gly
 1               5                  10                  15

GAG AGA GTC ACT TTC ACT TGC AAG GCG AGT CAG GAC ATT AAT AAC TAT      96
Glu Arg Val Thr Phe Thr Cys Lys Ala Ser Gln Asp Ile Asn Asn Tyr
                20                  25                  30

TTA TGC TGG TTC CAG CAG AAA CCA GGG AAA TCT CCT AAG ACC CTG ATC     144
Leu Cys Trp Phe Gln Gln Lys Pro Gly Lys Ser Pro Lys Thr Leu Ile
            35                  40                  45

TAT CGT GCA AAC AGA CTG GTA GAT GGG GTC CCA TCA AGG TTC AGT GGC     192
Tyr Arg Ala Asn Arg Leu Val Asp Gly Val Pro Ser Arg Phe Ser Gly
        50                  55                  60

AGT GGA TCT GGA CAA GAT TAT TCT CTC ACC ATT AGC AGC CTG GAG TAT     240
Ser Gly Ser Gly Gln Asp Tyr Ser Leu Thr Ile Ser Ser Leu Glu Tyr
 65                  70                  75                  80

GAA GAT ATG GGA ATT TAT TAT TGT CTA CAG TAT GAT GAG TTT CCG TAC     288
Glu Asp Met Gly Ile Tyr Tyr Cys Leu Gln Tyr Asp Glu Phe Pro Tyr
                 85                  90                  95

ACG TTC GGA GGG GGG ACC AAG CTG GAA ATA AAA GGA GGC GGT GGC TCG     336
Thr Phe Gly Gly Gly Thr Lys Leu Glu Ile Lys Gly Gly Gly Gly Ser
                100                 105                 110

GGC GGT GGC GGA TCG GGT GGC GGC GGC TCT GAG GTT CAG CTC CAG CAG     384
Gly Gly Gly Gly Ser Gly Gly Gly Gly Ser Glu Val Gln Leu Gln Gln
            115                 120                 125

TCT GGG ACT GTA CTG GCA AGG CCT GGG GCT TCA GTG AAG ATG TCC TGC     432
Ser Gly Thr Val Leu Ala Arg Pro Gly Ala Ser Val Lys Met Ser Cys
        130                 135                 140

AAG GCT TCT GGC TAC ACC TTT TCC AGC TAC TGG ATG CAC TGG ATA AAA     480
Lys Ala Ser Gly Tyr Thr Phe Ser Ser Tyr Trp Met His Trp Ile Lys
145                 150                 155                 160

CAG AGG CCT GGA CAG GGT CTG GAC TGG ATT GTC GCT ATT GAT CCT CGA     528
Gln Arg Pro Gly Gln Gly Leu Asp Trp Ile Val Ala Ile Asp Pro Arg
                165                 170                 175

AAT AGT GAT ACT ATT TAC AAC CCG CAA TTC AAA CAC AAG GCC AAA CTG     576
Asn Ser Asp Thr Ile Tyr Asn Pro Gln Phe Lys His Lys Ala Lys Leu
            180                 185                 190

ACT GCA GTC ACC TCC ACC AGC ACT GCC TAC ATG GAA CTC AAC AGC CTG     624
Thr Ala Val Thr Ser Thr Ser Thr Ala Tyr Met Glu Leu Asn Ser Leu
        195                 200                 205

ACA AAT GAG GAC TCT GCG GTC TAT TAC TGT ACC CCT CTT TAT TAC TTT     672
Thr Asn Glu Asp Ser Ala Val Tyr Tyr Cys Thr Pro Leu Tyr Tyr Phe
    210                 215                 220

GAC TCC TGG GGC CAA GGC ACC ACT CTC ACA GTC TCC TCA GCC AAG AAA     720
Asp Ser Trp Gly Gln Gly Thr Thr Leu Thr Val Ser Ser Ala Lys Lys
```

```
225                 230                 235                 240
CTG AAC GAC GCT CAG GCG CCG AAG AGT GAT ATG TCA GAT TGG CTT ACA        768
Leu Asn Asp Ala Gln Ala Pro Lys Ser Asp Met Ser Asp Trp Leu Thr
                245                 250                 255

TTT CAG AAA AAA CAC ATC ACA AAC ACA AGG GAT GTT GAT TGT GAT AAT        816
Phe Gln Lys Lys His Ile Thr Asn Thr Arg Asp Val Asp Cys Asp Asn
            260                 265                 270

ATC ATG TCA ACA AAC TTG TTC CAC TGC AAG GAC AAG AAC ACT TTT ATC        864
Ile Met Ser Thr Asn Leu Phe His Cys Lys Asp Lys Asn Thr Phe Ile
        275                 280                 285

TAT TCA CGT CCT GAG CCA GTG AAG GCC ATC TGT AAA GGA ATT ATA GCC        912
Tyr Ser Arg Pro Glu Pro Val Lys Ala Ile Cys Lys Gly Ile Ile Ala
    290                 295                 300

TCC AAA AAT GTG TTA ACT ACC TCT GAG TTT TAT CTC TCT GAT TGC AAT        960
Ser Lys Asn Val Leu Thr Thr Ser Glu Phe Tyr Leu Ser Asp Cys Asn
305                 310                 315                 320

GTA ACA AGC AGG CCT TGC AAG TAT AAA TTA AAG AAA TCA ACT AAT AAA       1008
Val Thr Ser Arg Pro Cys Lys Tyr Lys Leu Lys Lys Ser Thr Asn Lys
                325                 330                 335

TTT TGT GTA ACT TGT GAA AAT CAG GCA CCA GTT CAT TTT GTT GGA GTT       1056
Phe Cys Val Thr Cys Glu Asn Gln Ala Pro Val His Phe Val Gly Val
            340                 345                 350

GGA TCT TGT                                                           1065
Gly Ser Cys
        355

(2) INFORMATION FOR SEQ ID NO:49:

(i) SEQUENCE CHARACTERISTICS:
        (A) LENGTH: 355 amino acids
        (B) TYPE: amino acid
        (D) TOPOLOGY: linear (ii) MOLECULE TYPE: protein (xi) SEQUENCE DESCRIPTION: SEQ ID NO:49:

Asp Ile Lys Met Thr Gln Ser Pro Ser Ser Met Tyr Ala Ser Leu Gly
 1               5                  10                  15

Glu Arg Val Thr Phe Thr Cys Lys Ala Ser Gln Asp Ile Asn Asn Tyr
            20                  25                  30

Leu Cys Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Glu Val Gln Leu Gln Gln
        115                 120                 125

Ser Gly Thr Val Leu Ala Arg Pro Gly Ala Ser Val Lys Met Ser Cys
    130                 135                 140

Lys Ala Ser Gly Tyr Thr Phe Ser Ser Tyr Trp Met His Trp Ile Lys
145                 150                 155                 160

Gln Arg Pro Gly Gln Gly Leu Asp Trp Ile Val Ala Ile Asp Pro Arg
                165                 170                 175
```

```
Asn Ser Asp Thr Ile Tyr Asn Pro Gln Phe Lys His Lys Ala Lys Leu
            180                 185                 190

Thr Ala Val Thr Ser Thr Ser Thr Ala Tyr Met Glu Leu Asn Ser Leu
            195                 200                 205

Thr Asn Glu Asp Ser Ala Val Tyr Tyr Cys Thr Pro Leu Tyr Tyr Phe
            210                 215                 220

Asp Ser Trp Gly Gln Gly Thr Thr Leu Thr Val Ser Ser Ala Lys Lys
225                 230                 235                 240

Leu Asn Asp Ala Gln Ala Pro Lys Ser Asp Met Ser Asp Trp Leu Thr
            245                 250                 255

Phe Gln Lys Lys His Ile Thr Asn Thr Arg Asp Val Asp Cys Asp Asn
            260                 265                 270

Ile Met Ser Thr Asn Leu Phe His Cys Lys Asp Lys Asn Thr Phe Ile
            275                 280                 285

Tyr Ser Arg Pro Glu Pro Val Lys Ala Ile Cys Lys Gly Ile Ile Ala
            290                 295                 300

Ser Lys Asn Val Leu Thr Thr Ser Glu Phe Tyr Leu Ser Asp Cys Asn
305                 310                 315                 320

Val Thr Ser Arg Pro Cys Lys Tyr Lys Leu Lys Lys Ser Thr Asn Lys
            325                 330                 335

Phe Cys Val Thr Cys Glu Asn Gln Ala Pro Val His Phe Val Gly Val
            340                 345                 350

Gly Ser Cys
       355

(2) INFORMATION FOR SEQ ID NO:50:

(i) SEQUENCE CHARACTERISTICS:
        (A) LENGTH: 1074 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..1074
        (D) OTHER INFORMATION: /note= "MetGluOncFBE6"

(xi) SEQUENCE DESCRIPTION: SEQ ID NO:50:

ATG GAG GAT TGG CTT ACA TTT CAG AAA AAA CAC ATC ACA AAC ACA AGG      48
Met Glu Asp Trp Leu Thr Phe Gln Lys Lys His Ile Thr Asn Thr Arg
  1               5                  10                  15

GAT GTT GAT TGT GAT AAT ATC ATG TCA ACA AAC TTG TTC CAC TGC AAG      96
Asp Val Asp Cys Asp Asn Ile Met Ser Thr Asn Leu Phe His Cys Lys
                 20                  25                  30

GAC AAG AAC ACT TTT ATC TAT TCA CGT CCT GAG CCA GTG AAG GCC ATC     144
Asp Lys Asn Thr Phe Ile Tyr Ser Arg Pro Glu Pro Val Lys Ala Ile
             35                  40                  45

TGT AAA GGA ATT ATA GCC TCC AAA AAT GTG TTA ACT ACC TCT GAG TTT     192
Cys Lys Gly Ile Ile Ala Ser Lys Asn Val Leu Thr Thr Ser Glu Phe
         50                  55                  60

TAT CTC TCT GAT TGC AAT GTA ACA AGC AGG CCT TGC AAG TAT AAA TTA     240
Tyr Leu Ser Asp Cys Asn Val Thr Ser Arg Pro Cys Lys Tyr Lys Leu
 65                  70                  75                  80

AAG AAA TCA ACT AAT AAA TTT TGT GTA ACT TGT GAA AAT CAG GCA CCA     288
Lys Lys Ser Thr Asn Lys Phe Cys Val Thr Cys Glu Asn Gln Ala Pro
                 85                  90                  95

GTT CAT TTT GTT GGA GTT GGA TCT TGT GCC AAG AAA CTG AAC GAC GCT     336
```

```
Val His Phe Val Gly Val Gly Ser Cys Ala Lys Lys Leu Asn Asp Ala
            100                 105                 110

CAG GCG CCG AAG AGT GAT GAC ATC AAG ATG ACC CAG TCT CCA TCT TCC        384
Gln Ala Pro Lys Ser Asp Asp Ile Lys Met Thr Gln Ser Pro Ser Ser
        115                 120                 125

ATG TAT GCA TCT CTA GGA GAG AGA GTC ACT TTC ACT TGC AAG GCG AGT        432
Met Tyr Ala Ser Leu Gly Glu Arg Val Thr Phe Thr Cys Lys Ala Ser
    130                 135                 140

CAG GAC ATT AAT AAC TAT TTA TGC TGG TTC CAG CAG AAA CCA GGG AAA        480
Gln Asp Ile Asn Asn Tyr Leu Cys Trp Phe Gln Gln Lys Pro Gly Lys
145                 150                 155                 160

TCT CCT AAG ACC CTG ATC TAT CGT GCA AAC AGA CTG GTA GAT GGG GTC        528
Ser Pro Lys Thr Leu Ile Tyr Arg Ala Asn Arg Leu Val Asp Gly Val
            165                 170                 175

CCA TCA AGG TTC AGT GGC AGT GGA TCT GGA CAA GAT TAT TCT CTC ACC        576
Pro Ser Arg Phe Ser Gly Ser Gly Ser Gly Gln Asp Tyr Ser Leu Thr
        180                 185                 190

ATT AGC AGC CTG GAG TAT GAA GAT ATG GGA ATT TAT TAT TGT CTA CAG        624
Ile Ser Ser Leu Glu Tyr Glu Asp Met Gly Ile Tyr Tyr Cys Leu Gln
    195                 200                 205

TAT GAT GAG TTT CCG TAC ACG TTC GGA GGG GGG ACC AAG CTG GAA ATA        672
Tyr Asp Glu Phe Pro Tyr Thr Phe Gly Gly Gly Thr Lys Leu Glu Ile
210                 215                 220

AAA GGA GGC GGT GGC TCG GGC GGT GGC GGA TCG GGT GGC GGC GGC TCT        720
Lys Gly Gly Gly Gly Ser Gly Gly Gly Gly Ser Gly Gly Gly Gly Ser
225                 230                 235                 240

GAG GTT CAG CTC CAG CAG TCT GGG ACT GTA CTG GCA AGG CCT GGG GCT        768
Glu Val Gln Leu Gln Gln Ser Gly Thr Val Leu Ala Arg Pro Gly Ala
            245                 250                 255

TCA GTG AAG ATG TCC TGC AAG GCT TCT GGC TAC ACC TTT TCC AGC TAC        816
Ser Val Lys Met Ser Cys Lys Ala Ser Gly Tyr Thr Phe Ser Ser Tyr
        260                 265                 270

TGG ATG CAC TGG ATA AAA CAG AGG CCT GGA CAG GGT CTG GAC TGG ATT        864
Trp Met His Trp Ile Lys Gln Arg Pro Gly Gln Gly Leu Asp Trp Ile
    275                 280                 285

GTC GCT ATT GAT CCT CGA AAT AGT GAT ACT ATT TAC AAC CCG CAA TTC        912
Val Ala Ile Asp Pro Arg Asn Ser Asp Thr Ile Tyr Asn Pro Gln Phe
290                 295                 300

AAA CAC AAG GCC AAA CTG ACT GCA GTC ACC TCC ACC AGC ACT GCC TAC        960
Lys His Lys Ala Lys Leu Thr Ala Val Thr Ser Thr Ser Thr Ala Tyr
305                 310                 315                 320

ATG GAA CTC AAC AGC CTG ACA AAT GAG GAC TCT GCG GTC TAT TAC TGT       1008
Met Glu Leu Asn Ser Leu Thr Asn Glu Asp Ser Ala Val Tyr Tyr Cys
            325                 330                 335

ACC CCT CTT TAT TAC TTT GAC TCC TGG GGC CAA GGC ACC ACT CTC ACA       1056
Thr Pro Leu Tyr Tyr Phe Asp Ser Trp Gly Gln Gly Thr Thr Leu Thr
        340                 345                 350

GTC TCC TCA CAT CAC CAT                                                1074
Val Ser Ser His His His
    355
```

(2) INFORMATION FOR SEQ ID NO:51:

(i) SEQUENCE CHARACTERISTICS:
        (A) LENGTH: 358 amino acids
        (B) TYPE: amino acid
        (D) TOPOLOGY: linear (ii) MOLECULE TYPE: protein (xi) SEQUENCE DESCRIPTION: SEQ ID NO:51:

```
Met Glu Asp Trp Leu Thr Phe Gln Lys Lys His Ile Thr Asn Thr Arg
 1               5                  10                 15

Asp Val Asp Cys Asp Asn Ile Met Ser Thr Asn Leu Phe His Cys Lys
                20                  25                 30

Asp Lys Asn Thr Phe Ile Tyr Ser Arg Pro Glu Pro Val Lys Ala Ile
            35                  40                 45

Cys Lys Gly Ile Ile Ala Ser Lys Asn Val Leu Thr Thr Ser Glu Phe
        50                  55                  60

Tyr Leu Ser Asp Cys Asn Val Thr Ser Arg Pro Cys Lys Tyr Lys Leu
 65                 70                  75                  80

Lys Lys Ser Thr Asn Lys Phe Cys Val Thr Cys Glu Asn Gln Ala Pro
                85                  90                  95

Val His Phe Val Gly Val Gly Ser Cys Ala Lys Lys Leu Asn Asp Ala
                100                 105                 110

Gln Ala Pro Lys Ser Asp Asp Ile Lys Met Thr Gln Ser Pro Ser Ser
            115                 120                 125

Met Tyr Ala Ser Leu Gly Glu Arg Val Thr Phe Thr Cys Lys Ala Ser
130                 135                 140

Gln Asp Ile Asn Asn Tyr Leu Cys Trp Phe Gln Gln Lys Pro Gly Lys
145                 150                 155                 160

Ser Pro Lys Thr Leu Ile Tyr Arg Ala Asn Arg Leu Val Asp Gly Val
                165                 170                 175

Pro Ser Arg Phe Ser Gly Ser Gly Ser Gly Gln Asp Tyr Ser Leu Thr
                180                 185                 190

Ile Ser Ser Leu Glu Tyr Glu Asp Met Gly Ile Tyr Tyr Cys Leu Gln
                195                 200                 205

Tyr Asp Glu Phe Pro Tyr Thr Phe Gly Gly Gly Thr Lys Leu Glu Ile
210                 215                 220

Lys Gly Gly Gly Gly Ser Gly Gly Gly Gly Ser Gly Gly Gly Gly Ser
225                 230                 235                 240

Glu Val Gln Leu Gln Gln Ser Gly Thr Val Leu Ala Arg Pro Gly Ala
                245                 250                 255

Ser Val Lys Met Ser Cys Lys Ala Ser Gly Tyr Thr Phe Ser Ser Tyr
                260                 265                 270

Trp Met His Trp Ile Lys Gln Arg Pro Gly Gln Gly Leu Asp Trp Ile
                275                 280                 285

Val Ala Ile Asp Pro Arg Asn Ser Asp Thr Ile Tyr Asn Pro Gln Phe
290                 295                 300

Lys His Lys Ala Lys Leu Thr Ala Val Thr Ser Thr Ser Thr Ala Tyr
305                 310                 315                 320

Met Glu Leu Asn Ser Leu Thr Asn Glu Asp Ser Ala Val Tyr Tyr Cys
                325                 330                 335

Thr Pro Leu Tyr Tyr Phe Asp Ser Trp Gly Gln Gly Thr Thr Leu Thr
                340                 345                 350

Val Ser Ser His His His
                355

(2) INFORMATION FOR SEQ ID NO:52:

(i) SEQUENCE CHARACTERISTICS:
        (A) LENGTH: 1095 base pairs
        (B) TYPE: nucleic acid
        (C) STRANDEDNESS: single
        (D) TOPOLOGY: linear (ii) MOLECULE TYPE: DNA
```

(ix) FEATURE:
    (A) NAME/KEY: CDS
    (B) LOCATION: 1..1095
    (D) OTHER INFORMATION: /note= "MetSerOncA87FBMOC31"

(xi) SEQUENCE DESCRIPTION: SEQ ID NO:52:

| | | | | | | | | | | | | | | | |
|---|---|---|---|---|---|---|---|---|---|---|---|---|---|---|---|
| ATG | TCA | GAT | TGG | CTT | ACA | TTT | CAG | AAA | AAA | CAC | ATC | ACA | AAC | ACA | AGG | 48 |
| Met | Ser | Asp | Trp | Leu | Thr | Phe | Gln | Lys | Lys | His | Ile | Thr | Asn | Thr | Arg | |
| 1 | | | | 5 | | | | | 10 | | | | | 15 | | |
| GAT | GTT | GAT | TGT | GAT | AAT | ATC | ATG | TCA | ACA | AAC | TTG | TTC | CAC | TGC | AAG | 96 |
| Asp | Val | Asp | Cys | Asp | Asn | Ile | Met | Ser | Thr | Asn | Leu | Phe | His | Cys | Lys | |
| | | | 20 | | | | | 25 | | | | | 30 | | | |
| GAC | AAG | AAC | ACT | TTT | ATC | TAT | TCA | CGT | CCT | GAG | CCA | GTG | AAG | GCC | ATC | 144 |
| Asp | Lys | Asn | Thr | Phe | Ile | Tyr | Ser | Arg | Pro | Glu | Pro | Val | Lys | Ala | Ile | |
| | | | | 35 | | | | | 40 | | | | | 45 | | |
| TGT | AAA | GGA | ATT | ATA | GCC | TCC | AAA | AAT | GTG | TTA | ACT | ACC | TCT | GAG | TTT | 192 |
| Cys | Lys | Gly | Ile | Ile | Ala | Ser | Lys | Asn | Val | Leu | Thr | Thr | Ser | Glu | Phe | |
| | | 50 | | | | | 55 | | | | | 60 | | | | |
| TAT | CTC | TCT | GAT | TGC | AAT | GTA | ACA | AGC | AGG | CCT | TGC | AAG | TAT | AAA | TTA | 240 |
| Tyr | Leu | Ser | Asp | Cys | Asn | Val | Thr | Ser | Arg | Pro | Cys | Lys | Tyr | Lys | Leu | |
| 65 | | | | | 70 | | | | | 75 | | | | | 80 | |
| AAG | AAA | TCA | ACT | AAT | AAA | TTT | GCT | GTA | ACT | TGT | GAA | AAT | CAG | GCA | CCA | 288 |
| Lys | Lys | Ser | Thr | Asn | Lys | Phe | Ala | Val | Thr | Cys | Glu | Asn | Gln | Ala | Pro | |
| | | | | 85 | | | | | 90 | | | | | 95 | | |
| GTT | CAT | TTT | GTT | GGA | GTT | GGA | TCT | TGT | GCC | AAG | AAA | CTG | AAC | GAC | GCT | 336 |
| Val | His | Phe | Val | Gly | Val | Gly | Ser | Cys | Ala | Lys | Lys | Leu | Asn | Asp | Ala | |
| | | | 100 | | | | | 105 | | | | | 110 | | | |
| CAG | GCG | CCG | AAG | AGT | GAT | CAG | GTG | AAG | CTG | CAG | CAG | TCA | GGA | CCT | GAG | 384 |
| Gln | Ala | Pro | Lys | Ser | Asp | Gln | Val | Lys | Leu | Gln | Gln | Ser | Gly | Pro | Glu | |
| | | | 115 | | | | | 120 | | | | | 125 | | | |
| CTG | AAG | AAG | CCT | GGA | GAG | ACA | GTC | AAG | ATC | TCC | TGC | AAG | GCT | TCT | GGG | 432 |
| Leu | Lys | Lys | Pro | Gly | Glu | Thr | Val | Lys | Ile | Ser | Cys | Lys | Ala | Ser | Gly | |
| | 130 | | | | | 135 | | | | | 140 | | | | | |
| TAC | ACC | TTC | ACA | AAC | TAT | GGA | ATG | AAC | TGG | GTG | AAG | CAG | GCT | CCA | GGA | 480 |
| Tyr | Thr | Phe | Thr | Asn | Tyr | Gly | Met | Asn | Trp | Val | Lys | Gln | Ala | Pro | Gly | |
| 145 | | | | | 150 | | | | | 155 | | | | | 160 | |
| AAG | GGT | TTA | AAG | TGG | ATG | GGC | TGG | ATA | AAC | ACC | TAC | ACT | GGA | GAG | TCA | 528 |
| Lys | Gly | Leu | Lys | Trp | Met | Gly | Trp | Ile | Asn | Thr | Tyr | Thr | Gly | Glu | Ser | |
| | | | | 165 | | | | | 170 | | | | | 175 | | |
| ACA | TAT | GCT | GAT | GAC | TTC | AAG | GGA | CGG | TTT | GCC | TTT | TCT | CTA | GAA | ACC | 576 |
| Thr | Tyr | Ala | Asp | Asp | Phe | Lys | Gly | Arg | Phe | Ala | Phe | Ser | Leu | Glu | Thr | |
| | | | 180 | | | | | 185 | | | | | 190 | | | |
| TCT | GCC | AGC | GCT | GCC | TAT | TTG | CAG | ATC | AAC | AAC | CTC | AAA | AAT | GAG | GAC | 624 |
| Ser | Ala | Ser | Ala | Ala | Tyr | Leu | Gln | Ile | Asn | Asn | Leu | Lys | Asn | Glu | Asp | |
| | | | 195 | | | | | 200 | | | | | 205 | | | |
| ACG | GCT | ACA | TAT | TTC | TGT | GCA | AGA | TTC | GCT | ATT | AAG | GGG | GAC | TAC | TGG | 672 |
| Thr | Ala | Thr | Tyr | Phe | Cys | Ala | Arg | Phe | Ala | Ile | Lys | Gly | Asp | Tyr | Trp | |
| | 210 | | | | | 215 | | | | | 220 | | | | | |
| GGC | CAA | GGG | ACC | ACG | GTC | ACC | GTC | TCC | TCA | GGT | GGA | GGC | GGT | TCA | GGC | 720 |
| Gly | Gln | Gly | Thr | Thr | Val | Thr | Val | Ser | Ser | Gly | Gly | Gly | Gly | Ser | Gly | |
| 225 | | | | | 230 | | | | | 235 | | | | | 240 | |
| GGA | GGT | GGC | TCT | GGC | GGT | GGC | GGA | TCG | GAC | ATT | GTG | CTA | ACC | CAG | TCT | 768 |
| Gly | Gly | Gly | Ser | Gly | Gly | Gly | Gly | Ser | Asp | Ile | Val | Leu | Thr | Gln | Ser | |
| | | | | 245 | | | | | 250 | | | | | 255 | | |
| CCA | TTC | TCC | AAT | CCA | GTC | ACT | CTT | GGA | ACA | TCA | GCT | TCC | ATC | TCC | TGC | 816 |
| Pro | Phe | Ser | Asn | Pro | Val | Thr | Leu | Gly | Thr | Ser | Ala | Ser | Ile | Ser | Cys | |
| | | | 260 | | | | | 265 | | | | | 270 | | | |
| AGG | TCT | ACT | AAG | AGT | CTC | CTA | CAT | AGT | AAT | GGC | ATC | ACT | TAT | TTG | TAT | 864 |
| Arg | Ser | Thr | Lys | Ser | Leu | Leu | His | Ser | Asn | Gly | Ile | Thr | Tyr | Leu | Tyr | |
| | | 275 | | | | | 280 | | | | | 285 | | | | |

```
TGG TAT CTG CAG AAG CCA GGC CAG TCT CCT CAG CTC CTG ATT TAT CAG       912
Trp Tyr Leu Gln Lys Pro Gly Gln Ser Pro Gln Leu Leu Ile Tyr Gln
    290                 295                 300

ATG TCC AAC CTT GCC TCA GGA GTC CCA GAC AGG TTC AGT AGC AGT GGG       960
Met Ser Asn Leu Ala Ser Gly Val Pro Asp Arg Phe Ser Ser Ser Gly
305                 310                 315                 320

TCA GGA ACT GAT TTC ACA CTG AGA ATC AGC AGA GTG GAG GCT GAG GAT      1008
Ser Gly Thr Asp Phe Thr Leu Arg Ile Ser Arg Val Glu Ala Glu Asp
                325                 330                 335

GTG GGT GTT TAT TAC TGT GCT CAA AAT CTA GAA ATT CCT CGG ACG TTC      1056
Val Gly Val Tyr Tyr Cys Ala Gln Asn Leu Glu Ile Pro Arg Thr Phe
340                 345                 350

GGT GGA GGC ACC AAG CTG GAA ATC AAA CGG GCG GCC GCA                  1095
Gly Gly Gly Thr Lys Leu Glu Ile Lys Arg Ala Ala Ala
                355                 360                 365
```

(2) INFORMATION FOR SEQ ID NO:53:

(i) SEQUENCE CHARACTERISTICS:
        (A) LENGTH: 365 amino acids
        (B) TYPE: amino acid
        (D) TOPOLOGY: linear (ii) MOLECULE TYPE: protein (xi) SEQUENCE DESCRIPTION: SEQ ID NO:53:

```
Met Ser Asp Trp Leu Thr Phe Gln Lys Lys His Ile Thr Asn Thr Arg
1               5                   10                  15

Asp Val Asp Cys Asp Asn Ile Met Ser Thr Asn Leu Phe His Cys Lys
                20                  25                  30

Asp Lys Asn Thr Phe Ile Tyr Ser Arg Pro Glu Pro Val Lys Ala Ile
                35                  40                  45

Cys Lys Gly Ile Ile Ala Ser Lys Asn Val Leu Thr Thr Ser Glu Phe
        50                  55                  60

Tyr Leu Ser Asp Cys Asn Val Thr Ser Arg Pro Cys Lys Tyr Lys Leu
65                  70                  75                  80

Lys Lys Ser Thr Asn Lys Phe Ala Val Thr Cys Glu Asn Gln Ala Pro
                85                  90                  95

Val His Phe Val Gly Val Gly Ser Cys Ala Lys Lys Leu Asn Asp Ala
                100                 105                 110

Gln Ala Pro Lys Ser Asp Gln Val Lys Leu Gln Gln Ser Gly Pro Glu
            115                 120                 125

Leu Lys Lys Pro Gly Glu Thr Val Lys Ile Ser Cys Lys Ala Ser Gly
130                 135                 140

Tyr Thr Phe Thr Asn Tyr Gly Met Asn Trp Val Lys Gln Ala Pro Gly
145                 150                 155                 160

Lys Gly Leu Lys Trp Met Gly Trp Ile Asn Thr Tyr Thr Gly Glu Ser
                165                 170                 175

Thr Tyr Ala Asp Asp Phe Lys Gly Arg Phe Ala Phe Ser Leu Glu Thr
                180                 185                 190

Ser Ala Ser Ala Ala Tyr Leu Gln Ile Asn Asn Leu Lys Asn Glu Asp
            195                 200                 205

Thr Ala Thr Tyr Phe Cys Ala Arg Phe Ala Ile Lys Gly Asp Tyr Trp
        210                 215                 220

Gly Gln Gly Thr Thr Val Thr Val Ser Ser Gly Gly Gly Gly Ser Gly
225                 230                 235                 240

Gly Gly Gly Ser Gly Gly Gly Gly Ser Asp Ile Val Leu Thr Gln Ser
```

```
                    245                 250                 255
        Pro Phe Ser Asn Pro Val Thr Leu Gly Thr Ser Ala Ser Ile Ser Cys
                        260                 265                 270

Arg Ser Thr Lys Ser Leu Leu His Ser Asn Gly Ile Thr Tyr Leu Tyr
                        275                 280                 285

Trp Tyr Leu Gln Lys Pro Gly Gln Ser Pro Gln Leu Leu Ile Tyr Gln
                        290                 295                 300

Met Ser Asn Leu Ala Ser Gly Val Pro Asp Arg Phe Ser Ser Ser Gly
        305                 310                 315                 320

Ser Gly Thr Asp Phe Thr Leu Arg Ile Ser Arg Val Glu Ala Glu Asp
                                325                 330                 335

Val Gly Val Tyr Tyr Cys Ala Gln Asn Leu Glu Ile Pro Arg Thr Phe
                        340                 345                 350

Gly Gly Gly Thr Lys Leu Glu Ile Lys Arg Ala Ala Ala
                        355                 360                 365

(2) INFORMATION FOR SEQ ID NO:54:

(i) SEQUENCE CHARACTERISTICS:
        (A) LENGTH: 1098 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..1098
        (D) OTHER INFORMATION: /note= "MOC31FBMetSerOnc"

(xi) SEQUENCE DESCRIPTION: SEQ ID NO:54:

GGT CAG GTG AAG CTG CAG CAG TCA GGA CCT GAG CTG AAG AAG CCT GGA        48
Gly Gln Val Lys Leu Gln Gln Ser Gly Pro Glu Leu Lys Lys Pro Gly
  1               5                  10                  15

GAG ACA GTC AAG ATC TCC TGC AAG GCT TCT GGG TAC ACC TTC ACA AAC        96
Glu Thr Val Lys Ile Ser Cys Lys Ala Ser Gly Tyr Thr Phe Thr Asn
                 20                  25                  30

TAT GGA ATG AAC TGG GTG AAG CAG GCT CCA GGA AAG GGT TTA AAG TGG       144
Tyr Gly Met Asn Trp Val Lys Gln Ala Pro Gly Lys Gly Leu Lys Trp
             35                  40                  45

ATG GGC TGG ATA AAC ACC TAC ACT GGA GAG TCA ACA TAT GCT GAT GAC       192
Met Gly Trp Ile Asn Thr Tyr Thr Gly Glu Ser Thr Tyr Ala Asp Asp
 50                  55                  60

TTC AAG GGA CGG TTT GCC TTT TCT CTA GAA ACC TCT GCC AGC GCT GCC       240
Phe Lys Gly Arg Phe Ala Phe Ser Leu Glu Thr Ser Ala Ser Ala Ala
 65                  70                  75                  80

TAT TTG CAG ATC AAC AAC CTC AAA AAT GAG GAC ACG GCT ACA TAT TTC       288
Tyr Leu Gln Ile Asn Asn Leu Lys Asn Glu Asp Thr Ala Thr Tyr Phe
                 85                  90                  95

TGT GCA AGA TTC GCT ATT AAG GGG GAC TAC TGG GGC CAA GGG ACC ACG       336
Cys Ala Arg Phe Ala Ile Lys Gly Asp Tyr Trp Gly Gln Gly Thr Thr
            100                 105                 110

GTC ACC GTC TCC TCA GGT GGA GGC GGT TCA GGC GGA GGT GGC TCT GGC       384
Val Thr Val Ser Ser Gly Gly Gly Gly Ser Gly Gly Gly Gly Ser Gly
        115                 120                 125

GGT GGC GGA TCG GAC ATT GTG CTA ACC CAG TCT CCA TTC TCC AAT CCA       432
Gly Gly Gly Ser Asp Ile Val Leu Thr Gln Ser Pro Phe Ser Asn Pro
    130                 135                 140

GTC ACT CTT GGA ACA TCA GCT TCC ATC TCC TGC AGG TCT ACT AAG AGT       480
Val Thr Leu Gly Thr Ser Ala Ser Ile Ser Cys Arg Ser Thr Lys Ser
```

```
145                 150                 155                 160
CTC CTA CAT AGT AAT GGC ATC ACT TAT TTG TAT TGG TAT CTG CAG AAG     528
Leu Leu His Ser Asn Gly Ile Thr Tyr Leu Tyr Trp Tyr Leu Gln Lys
                165                 170                 175

CCA GGC CAG TCT CCT CAG CTC CTG ATT TAT CAG ATG TCC AAC CTT GCC     576
Pro Gly Gln Ser Pro Gln Leu Leu Ile Tyr Gln Met Ser Asn Leu Ala
                180                 185                 190

TCA GGA GTC CCA GAC AGG TTC AGT AGC AGT GGG TCA GGA ACT GAT TTC     624
Ser Gly Val Pro Asp Arg Phe Ser Ser Ser Gly Ser Gly Thr Asp Phe
                195                 200                 205

ACA CTG AGA ATC AGC AGA GTG GAG GCT GAG GAT GTG GGT GTT TAT TAC     672
Thr Leu Arg Ile Ser Arg Val Glu Ala Glu Asp Val Gly Val Tyr Tyr
        210                 215                 220

TGT GCT CAA AAT CTA GAA ATT CCT CGG ACG TTC GGT GGA GGC ACC AAG     720
Cys Ala Gln Asn Leu Glu Ile Pro Arg Thr Phe Gly Gly Gly Thr Lys
225                 230                 235                 240

CTG GAA ATC AAA CGG GCG GCC GCA GCC AAG AAA CTG AAC GAC GCT CAG     768
Leu Glu Ile Lys Arg Ala Ala Ala Ala Lys Lys Leu Asn Asp Ala Gln
                245                 250                 255

GCG CCG AAG AGT GAT ATG TCA GAT TGG CTT ACA TTT CAG AAA AAA CAC     816
Ala Pro Lys Ser Asp Met Ser Asp Trp Leu Thr Phe Gln Lys Lys His
                260                 265                 270

ATC ACA AAC ACA AGG GAT GTT GAT TGT GAT AAT ATC ATG TCA ACA AAC     864
Ile Thr Asn Thr Arg Asp Val Asp Cys Asp Asn Ile Met Ser Thr Asn
                275                 280                 285

TTG TTC CAC TGC AAG GAC AAG AAC ACT TTT ATC TAT TCA CGT CCT GAG     912
Leu Phe His Cys Lys Asp Lys Asn Thr Phe Ile Tyr Ser Arg Pro Glu
        290                 295                 300

CCA GTG AAG GCC ATC TGT AAA GGA ATT ATA GCC TCC AAA AAT GTG TTA     960
Pro Val Lys Ala Ile Cys Lys Gly Ile Ile Ala Ser Lys Asn Val Leu
305                 310                 315                 320

ACT ACC TCT GAG TTT TAT CTC TCT GAT TGC AAT GTA ACA AGC AGG CCT    1008
Thr Thr Ser Glu Phe Tyr Leu Ser Asp Cys Asn Val Thr Ser Arg Pro
                325                 330                 335

TGC AAG TAT AAA TTA AAG AAA TCA ACT AAT AAA TTT TGT GTA ACT TGT    1056
Cys Lys Tyr Lys Leu Lys Lys Ser Thr Asn Lys Phe Cys Val Thr Cys
                340                 345                 350

GAA AAT CAG GCA CCA GTT CAT TTT GTT GGA GTT GGA TCT TGT                1098
Glu Asn Gln Ala Pro Val His Phe Val Gly Val Gly Ser Cys
                355                 360                 365

(2) INFORMATION FOR SEQ ID NO:55:

(i) SEQUENCE CHARACTERISTICS:
        (A) LENGTH: 366 amino acids
        (B) TYPE: amino acid
        (D) TOPOLOGY: linear (ii) MOLECULE TYPE: protein (xi) SEQUENCE DESCRIPTION: SEQ ID NO:55:

Gly Gln Val Lys Leu Gln Gln Ser Gly Pro Glu Leu Lys Lys Pro Gly
1               5                   10                  15

Glu Thr Val Lys Ile Ser Cys Lys Ala Ser Gly Tyr Thr Phe Thr Asn
            20                  25                  30

Tyr Gly Met Asn Trp Val Lys Gln Ala Pro Gly Lys Gly Leu Lys Trp
        35                  40                  45

Met Gly Trp Ile Asn Thr Tyr Thr Gly Glu Ser Thr Tyr Ala Asp Asp
    50                  55                  60

Phe Lys Gly Arg Phe Ala Phe Ser Leu Glu Thr Ser Ala Ser Ala Ala
```

```
                65                  70                  75                  80
        Tyr Leu Gln Ile Asn Asn Leu Lys Asn Glu Asp Thr Ala Thr Tyr Phe
                            85                  90                  95

Cys Ala Arg Phe Ala Ile Lys Gly Asp Tyr Trp Gly Gln Gly Thr Thr
                        100                 105                 110

Val Thr Val Ser Ser Gly Gly Gly Gly Ser Gly Gly Gly Gly Ser Gly
                        115                 120                 125

Gly Gly Gly Ser Asp Ile Val Leu Thr Gln Ser Pro Phe Ser Asn Pro
                130                 135                 140

Val Thr Leu Gly Thr Ser Ala Ser Ile Ser Cys Arg Ser Thr Lys Ser
        145                 150                 155                 160

Leu Leu His Ser Asn Gly Ile Thr Tyr Leu Tyr Trp Tyr Leu Gln Lys
                        165                 170                 175

Pro Gly Gln Ser Pro Gln Leu Leu Ile Tyr Gln Met Ser Asn Leu Ala
                    180                 185                 190

Ser Gly Val Pro Asp Arg Phe Ser Ser Gly Ser Gly Thr Asp Phe
                195                 200                 205

Thr Leu Arg Ile Ser Arg Val Glu Ala Glu Asp Val Gly Val Tyr Tyr
                    210                 215                 220

Cys Ala Gln Asn Leu Glu Ile Pro Arg Thr Phe Gly Gly Gly Thr Lys
        225                 230                 235                 240

Leu Glu Ile Lys Arg Ala Ala Ala Lys Lys Leu Asn Asp Ala Gln
                        245                 250                 255

Ala Pro Lys Ser Asp Met Ser Asp Trp Leu Thr Phe Gln Lys Lys His
                    260                 265                 270

Ile Thr Asn Thr Arg Asp Val Asp Cys Asp Asn Ile Met Ser Thr Asn
                        275                 280                 285

Leu Phe His Cys Lys Asp Lys Asn Thr Phe Ile Tyr Ser Arg Pro Glu
                    290                 295                 300

Pro Val Lys Ala Ile Cys Lys Gly Ile Ile Ala Ser Lys Asn Val Leu
        305                 310                 315                 320

Thr Thr Ser Glu Phe Tyr Leu Ser Asp Cys Asn Val Thr Ser Arg Pro
                            325                 330                 335

Cys Lys Tyr Lys Leu Lys Lys Ser Thr Asn Lys Phe Cys Val Thr Cys
                        340                 345                 350

Glu Asn Gln Ala Pro Val His Phe Val Gly Val Gly Ser Cys
                        355                 360                 365

(2) INFORMATION FOR SEQ ID NO:56:

(i) SEQUENCE CHARACTERISTICS:
        (A) LENGTH: 1065 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..1065
        (D) OTHER INFORMATION: /note= "MetSerOncFBMOC161"

(xi) SEQUENCE DESCRIPTION: SEQ ID NO:56:

ATG TCA GAT TGG CTT ACA TTT CAG AAA AAA CAC ATC ACA AAC ACA AGG          48
Met Ser Asp Trp Leu Thr Phe Gln Lys Lys His Ile Thr Asn Thr Arg
  1               5                  10                  15

GAT GTT GAT TGT GAT AAT ATC ATG TCA ACA AAC TTG TTC CAC TGC AAG          96
```

-continued

```
Asp Val Asp Cys Asp Asn Ile Met Ser Thr Asn Leu Phe His Cys Lys
             20                  25                  30

GAC AAG AAC ACT TTT ATC TAT TCA CGT CCT GAG CCA GTG AAG GCC ATC      144
Asp Lys Asn Thr Phe Ile Tyr Ser Arg Pro Glu Pro Val Lys Ala Ile
         35                  40                  45

TGT AAA GGA ATT ATA GCC TCC AAA AAT GTG TTA ACC ACC TCT GAG TTT      192
Cys Lys Gly Ile Ile Ala Ser Lys Asn Val Leu Thr Thr Ser Glu Phe
     50                  55                  60

TAT CTC TCT GAT TGC AAT GTA ACA AGC AGG CCT TGC AAG TAT AAA TTA      240
Tyr Leu Ser Asp Cys Asn Val Thr Ser Arg Pro Cys Lys Tyr Lys Leu
 65                  70                  75                  80

AAG AAA TCA ACT AAT AAA TTT TGT GTA ACT TGT GAA AAT CAG GCA CCA      288
Lys Lys Ser Thr Asn Lys Phe Cys Val Thr Cys Glu Asn Gln Ala Pro
                 85                  90                  95

GTT CAT TTT GTT GGA GTT GGA TCT TGT GCC AAG AAA CTG AAC GAC GCT      336
Val His Phe Val Gly Val Gly Ser Cys Ala Lys Lys Leu Asn Asp Ala
             100                 105                 110

CAG GCG CCG AAG AGT GAT CAG GTC CAA CTG CAG CAG TCA GGA ACT GAG      384
Gln Ala Pro Lys Ser Asp Gln Val Gln Leu Gln Gln Ser Gly Thr Glu
         115                 120                 125

CTG ATA AGG CCT GGG ACT TCA GTG AAG ATA TCC TGT AAG GCT TCT GGA      432
Leu Ile Arg Pro Gly Thr Ser Val Lys Ile Ser Cys Lys Ala Ser Gly
    130                 135                 140

TAC GCC TTC ACT GAC TAC TGG CTA GGT TGG GTA AAA CAC AGG CCT GGA      480
Tyr Ala Phe Thr Asp Tyr Trp Leu Gly Trp Val Lys His Arg Pro Gly
145                 150                 155                 160

CAT GGA CTT GAG TGG ATT GGA GAT ATT TAC CCT GGA AGT GAT AAT ACT      528
His Gly Leu Glu Trp Ile Gly Asp Ile Tyr Pro Gly Ser Asp Asn Thr
                165                 170                 175

TAC TAC AAT GAG AAA TTC AAG GGC AAA GCC ACA CTG ACT ACA GAC AAA      576
Tyr Tyr Asn Glu Lys Phe Lys Gly Lys Ala Thr Leu Thr Thr Asp Lys
            180                 185                 190

TCC TCG AGC ACA GCC TAT ATG CAG CTC AGT AGC CTG ACA TCT GAG GAC      624
Ser Ser Ser Thr Ala Tyr Met Gln Leu Ser Ser Leu Thr Ser Glu Asp
        195                 200                 205

TCT GCT GTC TAT TTC TGT GCA AGG GGC CTT AAA GGA GAC TAC TGG GGC      672
Ser Ala Val Tyr Phe Cys Ala Arg Gly Leu Lys Gly Asp Tyr Trp Gly
    210                 215                 220

CAA GGG ACC ACC GTC ACC GTC TCC TCA GGT GGA GGC GGT TCA GGC GGA      720
Gln Gly Thr Thr Val Thr Val Ser Ser Gly Gly Gly Gly Ser Gly Gly
225                 230                 235                 240

GGT GGC TCT GGC GGT GGC GGA TCG GAC ATC CAG ATG ACC CAG TCT CCA      768
Gly Gly Ser Gly Gly Gly Gly Ser Asp Ile Gln Met Thr Gln Ser Pro
                245                 250                 255

TCC TCA CTG TCT GCA TCT CTG GGA GGC AAA GTC ACC ATC ACT TGC AAG      816
Ser Ser Leu Ser Ala Ser Leu Gly Gly Lys Val Thr Ile Thr Cys Lys
            260                 265                 270

GCA AGC CAA GAC ATT AAG AAG TCT ATA GCT TGG TAC CAA CAC AAG CCT      864
Ala Ser Gln Asp Ile Lys Lys Ser Ile Ala Trp Tyr Gln His Lys Pro
        275                 280                 285

GGA AAA GGT CCT AGG CTG CTC ATT CAT TAC ACA TCT ACA TTA CAG CCA      912
Gly Lys Gly Pro Arg Leu Leu Ile His Tyr Thr Ser Thr Leu Gln Pro
    290                 295                 300

GGC ATC CCA TCA AGG TTC AGT GGA AGT GGG TCT GGT GAA GAA TAT TCC      960
Gly Ile Pro Ser Arg Phe Ser Gly Ser Gly Ser Gly Glu Glu Tyr Ser
305                 310                 315                 320

TTC AGC ATC AGC AAC CTG GAG CCT GAA GAT ATT GCA ACT TAT TAT TGT      1008
Phe Ser Ile Ser Asn Leu Glu Pro Glu Asp Ile Ala Thr Tyr Tyr Cys
                325                 330                 335
```

```
CAA CAG TAT GAT AAT CTT CGG ACG TTC GGT GGA GGC ACC AAG CTG GAG        1056
Gln Gln Tyr Asp Asn Leu Arg Thr Phe Gly Gly Gly Thr Lys Leu Glu
        340                 345                 350

CTG AAA CGG                                                            1065
Leu Lys Arg
        355
```

(2) INFORMATION FOR SEQ ID NO:57:

(i) SEQUENCE CHARACTERISTICS:
       (A) LENGTH: 355 amino acids
       (B) TYPE: amino acid
       (D) TOPOLOGY: linear (ii) MOLECULE TYPE: protein (xi) SEQUENCE DESCRIPTION: SEQ ID NO:57:

```
Met Ser Asp Trp Leu Thr Phe Gln Lys Lys His Ile Thr Asn Thr Arg
 1               5                  10                  15

Asp Val Asp Cys Asp Asn Ile Met Ser Thr Asn Leu Phe His Cys Lys
             20                  25                  30

Asp Lys Asn Thr Phe Ile Tyr Ser Arg Pro Glu Pro Val Lys Ala Ile
         35                  40                  45

Cys Lys Gly Ile Ile Ala Ser Lys Asn Val Leu Thr Thr Ser Glu Phe
     50                  55                  60

Tyr Leu Ser Asp Cys Asn Val Thr Ser Arg Pro Cys Lys Tyr Lys Leu
 65                  70                  75                  80

Lys Lys Ser Thr Asn Lys Phe Cys Val Thr Cys Glu Asn Gln Ala Pro
                 85                  90                  95

Val His Phe Val Gly Val Gly Ser Cys Ala Lys Lys Leu Asn Asp Ala
                100                 105                 110

Gln Ala Pro Lys Ser Asp Gln Val Gln Leu Gln Gln Ser Gly Thr Glu
             115                 120                 125

Leu Ile Arg Pro Gly Thr Ser Val Lys Ile Ser Cys Lys Ala Ser Gly
130                 135                 140

Tyr Ala Phe Thr Asp Tyr Trp Leu Gly Trp Val Lys His Arg Pro Gly
145                 150                 155                 160

His Gly Leu Glu Trp Ile Gly Asp Ile Tyr Pro Gly Ser Asp Asn Thr
                165                 170                 175

Tyr Tyr Asn Glu Lys Phe Lys Gly Lys Ala Thr Leu Thr Thr Asp Lys
            180                 185                 190

Ser Ser Ser Thr Ala Tyr Met Gln Leu Ser Ser Leu Thr Ser Glu Asp
        195                 200                 205

Ser Ala Val Tyr Phe Cys Ala Arg Gly Leu Lys Gly Asp Tyr Trp Gly
    210                 215                 220

Gln Gly Thr Thr Val Thr Val Ser Ser Gly Gly Gly Ser Gly Gly
225                 230                 235                 240

Gly Gly Ser Gly Gly Gly Ser Asp Ile Gln Met Thr Gln Ser Pro
                245                 250                 255

Ser Ser Leu Ser Ala Ser Leu Gly Gly Lys Val Thr Ile Thr Cys Lys
                260                 265                 270

Ala Ser Gln Asp Ile Lys Lys Ser Ile Ala Trp Tyr Gln His Lys Pro
            275                 280                 285

Gly Lys Gly Pro Arg Leu Leu Ile His Tyr Thr Ser Thr Leu Gln Pro
        290                 295                 300

Gly Ile Pro Ser Arg Phe Ser Gly Ser Gly Ser Gly Glu Glu Tyr Ser
305                 310                 315                 320
```

```
Phe Ser Ile Ser Asn Leu Glu Pro Glu Asp Ile Ala Thr Tyr Tyr Cys
            325                 330                 335

Gln Gln Tyr Asp Asn Leu Arg Thr Phe Gly Gly Gly Thr Lys Leu Glu
            340                 345                 350

Leu Lys Arg
        355

(2) INFORMATION FOR SEQ ID NO:58:

(i) SEQUENCE CHARACTERISTICS:
        (A) LENGTH: 753 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..753
        (D) OTHER INFORMATION: /note= "IL2FBMetSerOnc"

(xi) SEQUENCE DESCRIPTION: SEQ ID NO:58:

GCA CCT ACT TCA ACT TCT ACA AAG AAA ACA CAG CTA CAA CTG GAG CAT       48
Ala Pro Thr Ser Thr Ser Thr Lys Lys Thr Gln Leu Gln Leu Glu His
 1               5                  10                  15

TTA CTG CTG GAT TTA CAG ATG ATT TTG AAT GGA ATT AAT AAT TAC AAG       96
Leu Leu Leu Asp Leu Gln Met Ile Leu Asn Gly Ile Asn Asn Tyr Lys
                20                  25                  30

AAT CCC AAA CTC ACC AGG ATG CTC ACA TTT AAG TTT TAC ATG CCC AAG      144
Asn Pro Lys Leu Thr Arg Met Leu Thr Phe Lys Phe Tyr Met Pro Lys
             35                  40                  45

AAG GCC ACA GAA CTG AAA CAT CTT CAG TGT CTA GAA GAA GAA CTC AAA      192
Lys Ala Thr Glu Leu Lys His Leu Gln Cys Leu Glu Glu Glu Leu Lys
         50                  55                  60

CCT CTG GAG GAA GTG CTA AAT TTA GCT CAA AGC AAA AAC TTT CAC TTA      240
Pro Leu Glu Glu Val Leu Asn Leu Ala Gln Ser Lys Asn Phe His Leu
 65                  70                  75                  80

AGA CCC AGG GAC TTA ATC AGC AAT ATC AAC GTA ATA GTT CTG GAA CTA      288
Arg Pro Arg Asp Leu Ile Ser Asn Ile Asn Val Ile Val Leu Glu Leu
                85                  90                  95

AAG GGA TCT GAA ACA ACA TTC ATG TGT GAA TAT GCT GAT GAG ACA GCA      336
Lys Gly Ser Glu Thr Thr Phe Met Cys Glu Tyr Ala Asp Glu Thr Ala
            100                 105                 110

ACC ATT GTA GAA TTT CTG AAC AGA TGG ATT ACC TTT TGT CAA AGC ATC      384
Thr Ile Val Glu Phe Leu Asn Arg Trp Ile Thr Phe Cys Gln Ser Ile
        115                 120                 125

ATC TCA ACA CTG ACT GCC AAG AAA CTG AAC GAC GCT CAG GCG CCG AAG      432
Ile Ser Thr Leu Thr Ala Lys Lys Leu Asn Asp Ala Gln Ala Pro Lys
    130                 135                 140

AGT GAT ATG TCA GAT TGG CTT ACA TTT CAG AAA AAA CAC ATC ACA AAC      480
Ser Asp Met Ser Asp Trp Leu Thr Phe Gln Lys Lys His Ile Thr Asn
145                 150                 155                 160

ACA AGG GAT GTT GAT TGT GAT AAT ATC ATG TCA ACA AAC TTG TTC CAC      528
Thr Arg Asp Val Asp Cys Asp Asn Ile Met Ser Thr Asn Leu Phe His
                165                 170                 175

TGC AAG GAC AAG AAC ACT TTT ATC TAT TCA CGT CCT GAG CCA GTG AAG      576
Cys Lys Asp Lys Asn Thr Phe Ile Tyr Ser Arg Pro Glu Pro Val Lys
            180                 185                 190

GCC ATC TGT AAA GGA ATT ATA GCC TCC AAA AAT GTG TTA ACT ACC TCT      624
Ala Ile Cys Lys Gly Ile Ile Ala Ser Lys Asn Val Leu Thr Thr Ser
        195                 200                 205
```

```
GAG TTT TAT CTC TCT GAT TGC AAT GTA ACA AGC AGG CCT TGC AAG TAT      672
Glu Phe Tyr Leu Ser Asp Cys Asn Val Thr Ser Arg Pro Cys Lys Tyr
    210                 215                 220

AAA TTA AAG AAA TCA ACT AAT AAA TTT TGT GTA ACT TGT GAA AAT CAG      720
Lys Leu Lys Lys Ser Thr Asn Lys Phe Cys Val Thr Cys Glu Asn Gln
225                 230                 235                 240

GCA CCA GTT CAT TTT GTT GGA GTT GGA TCT TGT                          753
Ala Pro Val His Phe Val Gly Val Gly Ser Cys
            245                 250

(2) INFORMATION FOR SEQ ID NO:59:

(i) SEQUENCE CHARACTERISTICS:
        (A) LENGTH: 251 amino acids
        (B) TYPE: amino acid
        (D) TOPOLOGY: linear (ii) MOLECULE TYPE: protein (xi) SEQUENCE DESCRIPTION: SEQ ID NO:59:

Ala Pro Thr Ser Thr Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                    100                 105                 110

Thr Ile Val Glu Phe Leu Asn Arg Trp Ile Thr Phe Cys Gln Ser Ile
            115                 120                 125

Ile Ser Thr Leu Thr Ala Lys Lys Leu Asn Asp Ala Gln Ala Pro Lys
130                 135                 140

Ser Asp Met Ser Asp Trp Leu Thr Phe Gln Lys Lys His Ile Thr Asn
145                 150                 155                 160

Thr Arg Asp Val Asp Cys Asp Asn Ile Met Ser Thr Asn Leu Phe His
                165                 170                 175

Cys Lys Asp Lys Asn Thr Phe Ile Tyr Ser Arg Pro Glu Pro Val Lys
            180                 185                 190

Ala Ile Cys Lys Gly Ile Ile Ala Ser Lys Asn Val Leu Thr Thr Ser
        195                 200                 205

Glu Phe Tyr Leu Ser Asp Cys Asn Val Thr Ser Arg Pro Cys Lys Tyr
    210                 215                 220

Lys Leu Lys Lys Ser Thr Asn Lys Phe Cys Val Thr Cys Glu Asn Gln
225                 230                 235                 240

Ala Pro Val His Phe Val Gly Val Gly Ser Cys
            245                 250

(2) INFORMATION FOR SEQ ID NO:60:

(i) SEQUENCE CHARACTERISTICS:
        (A) LENGTH: 768 base pairs
        (B) TYPE: nucleic acid
```

(C) STRANDEDNESS: single
        (D) TOPOLOGY: linear (ii) MOLECULE TYPE: DNA (ix) FEATURE:
        (A) NAME/KEY: CDS
        (B) LOCATION: 1..765
        (D) OTHER INFORMATION: /note= "MetSerOncFBIL2"

(xi) SEQUENCE DESCRIPTION: SEQ ID NO:60:

```
ATG TCA GAT TGG CTT ACA TTT CAG AAA AAA CAC ATC ACA AAC ACA AGG        48
Met Ser Asp Trp Leu Thr Phe Gln Lys Lys His Ile Thr Asn Thr Arg
 1               5                  10                  15

GAT GTT GAT TGT GAT AAT ATC ATG TCA ACA AAC TTG TTC CAC TGC AAG        96
Asp Val Asp Cys Asp Asn Ile Met Ser Thr Asn Leu Phe His Cys Lys
                20                  25                  30

GAC AAG AAC ACT TTT ATC TAT TCA CGT CCT GAG CCA GTG AAG GCC ATC       144
Asp Lys Asn Thr Phe Ile Tyr Ser Arg Pro Glu Pro Val Lys Ala Ile
            35                  40                  45

TGT AAA GGA ATT ATA GCC TCC AAA AAT GTG TTA ACT ACC TCT GAG TTT       192
Cys Lys Gly Ile Ile Ala Ser Lys Asn Val Leu Thr Thr Ser Glu Phe
 50                  55                  60

TAT CTC TCT GAT TGC AAT GTA ACA AGC AGG CCT TGC AAG TAT AAA TTA       240
Tyr Leu Ser Asp Cys Asn Val Thr Ser Arg Pro Cys Lys Tyr Lys Leu
 65                  70                  75                  80

AAG AAA TCA ACT AAT AAA TTT TGT GTA ACT TGT GAA AAT CAG GCA CCA       288
Lys Lys Ser Thr Asn Lys Phe Cys Val Thr Cys Glu Asn Gln Ala Pro
                85                  90                  95

GTT CAT TTT GTT GGA GTT GGA TCT TGT GCC AAG AAA CTG AAC GAC GCT       336
Val His Phe Val Gly Val Gly Ser Cys Ala Lys Lys Leu Asn Asp Ala
            100                 105                 110

CAG GCG CCG AAG AGT GAT GCA CCT ACT TCA ACT TCT ACA AAG AAA ACA       384
Gln Ala Pro Lys Ser Asp Ala Pro Thr Ser Thr Ser Thr Lys Lys Thr
        115                 120                 125

CAG CTA CAA CTG GAG CAT TTA CTG CTG GAT TTA CAG ATG ATT TTG AAT       432
Gln Leu Gln Leu Glu His Leu Leu Leu Asp Leu Gln Met Ile Leu Asn
130                 135                 140

GGA ATT AAT AAT TAC AAG AAT CCC AAA CTC ACC AGG ATG CTC ACA TTT       480
Gly Ile Asn Asn Tyr Lys Asn Pro Lys Leu Thr Arg Met Leu Thr Phe
145                 150                 155                 160

AAG TTT TAC ATG CCC AAG AAG GCC ACA GAA CTG AAA CAT CTT CAG TGT       528
Lys Phe Tyr Met Pro Lys Lys Ala Thr Glu Leu Lys His Leu Gln Cys
                165                 170                 175

CTA GAA GAA GAA CTC AAA CCT CTG GAG GAA GTG CTA AAT TTA GCT CAA       576
Leu Glu Glu Glu Leu Lys Pro Leu Glu Glu Val Leu Asn Leu Ala Gln
            180                 185                 190

AGC AAA AAC TTT CAC TTA AGA CCC AGG GAC TTA ATC AGC AAT ATC AAC       624
Ser Lys Asn Phe His Leu Arg Pro Arg Asp Leu Ile Ser Asn Ile Asn
        195                 200                 205

GTA ATA GTT CTG GAA CTA AAG GGA TCT GAA ACA ACA TTC ATG TGT GAA       672
Val Ile Val Leu Glu Leu Lys Gly Ser Glu Thr Thr Phe Met Cys Glu
    210                 215                 220

TAT GCT GAT GAG ACA GCA ACC ATT GTA GAA TTT CTG AAC AGA TGG ATT       720
Tyr Ala Asp Glu Thr Ala Thr Ile Val Glu Phe Leu Asn Arg Trp Ile
225                 230                 235                 240

ACC TTT TGT CAA AGC ATC ATC TCA ACA CTG ACT CAT CAC CAT              762
Thr Phe Cys Gln Ser Ile Ile Ser Thr Leu Thr His His His
                245                 250

TAATAG                                                                 768
```

(2) INFORMATION FOR SEQ ID NO:61:

(i) SEQUENCE CHARACTERISTICS:
        (A) LENGTH: 254 amino acids
        (B) TYPE: amino acid
        (D) TOPOLOGY: linear (ii) MOLECULE TYPE: protein (xi) SEQUENCE DESCRIPTION: SEQ ID NO:61:

```
Met Ser Asp Trp Leu Thr Phe Gln Lys Lys His Ile Thr Asn Thr Arg
 1               5                  10                  15

Asp Val Asp Cys Asp Asn Ile Met Ser Thr Asn Leu Phe His Cys Lys
                20                  25                  30

Asp Lys Asn Thr Phe Ile Tyr Ser Arg Pro Glu Pro Val Lys Ala Ile
            35                  40                  45

Cys Lys Gly Ile Ile Ala Ser Lys Asn Val Leu Thr Thr Ser Glu Phe
        50                  55                  60

Tyr Leu Ser Asp Cys Asn Val Thr Ser Arg Pro Cys Lys Tyr Lys Leu
 65                 70                  75                  80

Lys Lys Ser Thr Asn Lys Phe Cys Val Thr Cys Glu Asn Gln Ala Pro
                85                  90                  95

Val His Phe Val Gly Val Gly Ser Cys Ala Lys Lys Leu Asn Asp Ala
                100                 105                 110

Gln Ala Pro Lys Ser Asp Ala Pro Thr Ser Thr Ser Thr Lys Lys Thr
            115                 120                 125

Gln Leu Gln Leu Glu His Leu Leu Asp Leu Gln Met Ile Leu Asn
130                 135                 140

Gly Ile Asn Asn Tyr Lys Asn Pro Lys Leu Thr Arg Met Leu Thr Phe
145                 150                 155                 160

Lys Phe Tyr Met Pro Lys Lys Ala Thr Glu Leu Lys His Leu Gln Cys
                165                 170                 175

Leu Glu Glu Glu Leu Lys Pro Leu Glu Glu Val Leu Asn Leu Ala Gln
            180                 185                 190

Ser Lys Asn Phe His Leu Arg Pro Arg Asp Leu Ile Ser Asn Ile Asn
        195                 200                 205

Val Ile Val Leu Glu Leu Lys Gly Ser Glu Thr Thr Phe Met Cys Glu
210                 215                 220

Tyr Ala Asp Glu Thr Ala Thr Ile Val Glu Phe Leu Asn Arg Trp Ile
225                 230                 235                 240

Thr Phe Cys Gln Ser Ile Ile Ser Thr Leu Thr His His His
                245                 250
```

(2) INFORMATION FOR SEQ ID NO:62:

(i) SEQUENCE CHARACTERISTICS:
        (A) LENGTH: 387 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..387
        (D) OTHER INFORMATION: /note= "SigPepOnc"

(xi) SEQUENCE DESCRIPTION: SEQ ID NO:62:

```
ATG GGT CTG GAA AAA TCT CTG ATC CTG TTC CCG CTG TTC TTC CTG CTG        48
Met Gly Leu Glu Lys Ser Leu Ile Leu Phe Pro Leu Phe Phe Leu Leu
```

```
            1                 5                    10                   15
         CTG GGT TGG GTT CAG CCG TCT CTG GGT CAG GAT TGG CTT ACA TTT CAG        96
         Leu Gly Trp Val Gln Pro Ser Leu Gly Gln Asp Trp Leu Thr Phe Gln
                             20                  25                  30

AAA AAA CAC ATC ACA AAC ACA AGG GAT GTT GAT TGT GAT AAT ATC ATG       144
         Lys Lys His Ile Thr Asn Thr Arg Asp Val Asp Cys Asp Asn Ile Met
                     35                  40                  45

TCA ACA AAC TTG TTC CAC TGC AAG GAC AAG AAC ACT TTT ATC TAT TCA       192
         Ser Thr Asn Leu Phe His Cys Lys Asp Lys Asn Thr Phe Ile Tyr Ser
             50                  55                  60

CGT CCT GAG CCA GTG AAG GCC ATC TGT AAA GGA ATT ATA GCC TCC AAA       240
         Arg Pro Glu Pro Val Lys Ala Ile Cys Lys Gly Ile Ile Ala Ser Lys
         65                  70                  75                  80

AAT GTG TTA ACT ACC TCT GAG TTT TAT CTC TCT GAT TGC AAT GTA ACA       288
         Asn Val Leu Thr Thr Ser Glu Phe Tyr Leu Ser Asp Cys Asn Val Thr
                             85                  90                  95

AGC AGG CCT TGC AAG TAT AAA TTA AAG AAA TCA ACT AAT AAA TTT TGT       336
         Ser Arg Pro Cys Lys Tyr Lys Leu Lys Lys Ser Thr Asn Lys Phe Cys
                     100                 105                 110

GTA ACT TGT GAA AAT CAG GCA CCA GTT CAT TTT GTT GGA GTT GGA TCT       384
         Val Thr Cys Glu Asn Gln Ala Pro Val His Phe Val Gly Val Gly Ser
             115                 120                 125

TGT                                                                  387
         Cys (2) INFORMATION FOR SEQ ID NO:63:

(i) SEQUENCE CHARACTERISTICS:
             (A) LENGTH: 129 amino acids
             (B) TYPE: amino acid
             (D) TOPOLOGY: linear (ii) MOLECULE TYPE: protein (xi) SEQUENCE DESCRIPTION: SEQ ID NO:63:

Met Gly Leu Glu Lys Ser Leu Ile Leu Phe Pro Leu Phe Phe Leu Leu
     1               5                   10                  15

Leu Gly Trp Val Gln Pro Ser Leu Gly Gln Asp Trp Leu Thr Phe Gln
                    20                  25                  30

Lys Lys His Ile Thr Asn Thr Arg Asp Val Asp Cys Asp Asn Ile Met
                35                  40                  45

Ser Thr Asn Leu Phe His Cys Lys Asp Lys Asn Thr Phe Ile Tyr Ser
        50                  55                  60

Arg Pro Glu Pro Val Lys Ala Ile Cys Lys Gly Ile Ile Ala Ser Lys
    65                  70                  75                  80

Asn Val Leu Thr Thr Ser Glu Phe Tyr Leu Ser Asp Cys Asn Val Thr
                    85                  90                  95

Ser Arg Pro Cys Lys Tyr Lys Leu Lys Lys Ser Thr Asn Lys Phe Cys
                100                 105                 110

Val Thr Cys Glu Asn Gln Ala Pro Val His Phe Val Gly Val Gly Ser
        115                 120                 125

Cys (2) INFORMATION FOR SEQ ID NO:64:

(i) SEQUENCE CHARACTERISTICS:
             (A) LENGTH: 355 amino acids
             (B) TYPE: amino acid
             (C) STRANDEDNESS:
             (D) TOPOLOGY: linear
```

(ii) MOLECULE TYPE: protein (ix) FEATURE:
    (A) NAME/KEY: Protein
    (B) LOCATION: 1..355
    (D) OTHER INFORMATION: /note= "E6FB[Met-(-1)]SerrOnc"

(xi) SEQUENCE DESCRIPTION: SEQ ID NO:64:

```
Asp Ile Lys Met Thr Gln Ser Pro Ser Ser Met Tyr Ala Ser Leu Gly
  1               5                  10                  15

Glu Arg Val Thr Phe Thr Cys Lys Ala Ser Gln Asp Ile Asn Asn Tyr
                 20                  25                  30

Leu Cys Trp Phe Gln Gln Lys Pro Gly Lys Ser Pro Lys Thr Leu Ile
             35                  40                  45

Tyr Arg Ala Asn Arg Leu Val Asp Gly Val Pro Ser Arg Phe Ser Gly
 50                  55                  60

Ser Gly Ser Gly Gln Asp Tyr Ser Leu Thr Ile Ser Ser Leu Glu Tyr
 65                  70                  75                  80

Glu Asp Met Gly Ile Tyr Tyr Cys Leu Gln Tyr Asp Glu Phe Pro Tyr
                 85                  90                  95

Thr Phe Gly Gly Gly Thr Lys Leu Glu Ile Lys Gly Gly Gly Gly Ser
                100                 105                 110

Gly Gly Gly Gly Ser Gly Gly Gly Ser Glu Val Gln Leu Gln Gln
            115                 120                 125

Ser Gly Thr Val Leu Ala Arg Pro Gly Ala Ser Val Lys Met Ser Cys
130                 135                 140

Lys Ala Ser Gly Tyr Thr Phe Ser Ser Tyr Trp Met His Trp Ile Lys
145                 150                 155                 160

Gln Arg Pro Gly Gln Gly Leu Asp Trp Ile Val Ala Ile Asp Pro Arg
                165                 170                 175

Asn Ser Asp Thr Ile Tyr Asn Pro Gln Phe Lys His Lys Ala Lys Leu
                180                 185                 190

Thr Ala Val Thr Ser Thr Ser Thr Ala Tyr Met Glu Leu Asn Ser Leu
            195                 200                 205

Thr Asn Glu Asp Ser Ala Val Tyr Tyr Cys Thr Pro Leu Tyr Tyr Phe
210                 215                 220

Asp Ser Trp Gly Gln Gly Thr Thr Leu Thr Val Ser Ser Ala Lys Lys
225                 230                 235                 240

Leu Asn Asp Ala Gln Ala Pro Lys Ser Asp Met Ser Asp Trp Leu Thr
                245                 250                 255

Phe Gln Lys Lys His Ile Thr Asn Thr Arg Asp Val Asp Cys Asp Asn
                260                 265                 270

Ile Met Ser Thr Asn Leu Phe His Cys Lys Asp Lys Asn Thr Phe Ile
            275                 280                 285

Tyr Ser Arg Pro Glu Pro Val Lys Ala Ile Cys Lys Gly Ile Ile Ala
290                 295                 300

Ser Lys Asn Val Leu Thr Thr Ser Glu Phe Tyr Leu Ser Asp Cys Asn
305                 310                 315                 320

Val Thr Ser Arg Pro Cys Lys Tyr Lys Leu Lys Lys Ser Thr Asn Lys
                325                 330                 335

Phe Cys Val Thr Cys Glu Asn Gln Ala Pro Val His Phe Val Gly Val
            340                 345                 350

Gly Ser Cys
355
```